US008529943B2

(12) United States Patent
Kliger et al.

(10) Patent No.: US 8,529,943 B2
(45) Date of Patent: Sep. 10, 2013

(54) ANGIOPOIETIN DERIVED PEPTIDES

(75) Inventors: Yossef Kliger, Rishon Le Zion (IL); Itamar Borukhov, Ramat Hasharon (IL); Ofer Levy, D.N Shimshon (IL); Zohar Tiran, Oranit (IL); Assaf Wool, Kiryat Ono (IL); Ehud Schreiber, Ramat Gan (IL); Anat Amir, D.N. Negev (IL); Zurit Levine, Herzliya (IL); Amir Toporik, Pardess Channa (IL)

(73) Assignee: Compugen Ltd., Tel-Aviv (IL)

( * ) Notice: Subject to any disclaimer, the term of this patent is extended or adjusted under 35 U.S.C. 154(b) by 50 days.

(21) Appl. No.: 13/054,914

(22) PCT Filed: Jul. 20, 2009

(86) PCT No.: PCT/IL2009/000709
§ 371 (c)(1),
(2), (4) Date: Apr. 14, 2011

(87) PCT Pub. No.: WO2010/010551
PCT Pub. Date: Jan. 28, 2010

(65) Prior Publication Data
US 2011/0206760 A1 Aug. 25, 2011

Related U.S. Application Data

(60) Provisional application No. 61/129,806, filed on Jul. 21, 2008.

(51) Int. Cl.
*C07K 14/515* (2006.01)
*C07K 14/00* (2006.01)
*C07K 7/06* (2006.01)
*C07K 7/08* (2006.01)
*C07K 16/46* (2006.01)
*A61K 38/16* (2006.01)
*A61K 38/08* (2006.01)
*A61K 38/10* (2006.01)

(52) U.S. Cl.
CPC .................................. *C07K 14/515* (2013.01)
USPC ........... 424/450; 530/324; 530/327; 530/326; 530/350; 530/387.3

(58) Field of Classification Search
None
See application file for complete search history.

(56) References Cited

U.S. PATENT DOCUMENTS

| 4,966,848 | A | * | 10/1990 | Smith et al. | 435/193 |
| 5,223,421 | A | * | 6/1993 | Smith et al. | 435/193 |
| 5,595,756 | A | * | 1/1997 | Bally et al. | 424/450 |
| 5,837,218 | A | * | 11/1998 | Peers et al. | 424/1.69 |

FOREIGN PATENT DOCUMENTS

| WO | WO 2004076650 | * | 9/2004 |
| WO | WO 2005/013890 | | 2/2005 |
| WO | WO 2010/010551 | | 1/2010 |

OTHER PUBLICATIONS

Auerbach et al (Cancer and Metastasis Reviews, 2000, 19: 167-172).*
Gura T (Science, 1997, 278(5340): 1041-1042.*
Jain RK (Scientific American, Jul. 1994,58-65).*
Sporn et at, "Chemoprevention of Cancer," Carcinogenesis, vol. 21 (2000), 525-530.*
Cancer Drug Design and Discovery Neidle, Stephen, ed. (Elsevier/Academic Press, 2008) p. 431.*
http://cancerweb.ncl.ac.uk/omd/about.html, Accessed Jul. 7, 2005.*
p. 1 from NINDS Multiple Sclerosis Information Page, Accessed Oct. 28, 2009.*
Siriam S, Steiner I, "Experimental Allergic Encephalomyelitis: A Misleading Model of Multiple Sclerosis," Ann. Neurol., 2005, 58: 939-945.*
Steinman L, Zamvil SS, "How to Successfully Apply Animal Studies in Experimental Allergic Encephalomyelitis to Research on Multiple Sclerosis," Ann. Neurol., 2006, 60: 12-21.*
Lo et al (High level expression and secretion of Fc-X fusion proteins in mammalian cells, Protein Engineering 11:6, 495-500, 1998).*
Communication Relating to the Results of the Partial International Search Dated Jan. 12, 2010 From the International Searching Authority Re. Application No. PCT/IL2009/000709.
International Preliminary Report on Patentability Dated Jan. 25, 2011 From the International Bureau of WIPO Re. Application No. PCT/IL2009/000709.
International Search Report and the Written Opinion Dated Mar. 29, 2010 From the International Searching Authority Re. Application No. PCT/IL2009/000709.
Ono et al. "Protein Region Important for Regulation of Lipid Metabolism in Angiopoietin-Like 3 (ANGPTL3). ANGPTL3 Is Cleaved and Activated In Vivo", The Journal of Biological Chemistry, XP002558624, 278(43): 41804-41809, Oct. 24, 2003.
Yuichi et al. "Angiopoietin-Like Proteins: Potential New Targets for Metabolic Syndrome Therapy", Trends in Molecular Medicine, XP005104728, 11(10): 473-479, Oct. 2005.
Communication Pursuant to Article 94(3) EPC Dated Jul. 18, 2012 From the European Patent Office Re. Application No. 09787476.2.
Communication Pursuant to Article 94(3) EPC Dated Jun. 3, 2013 From the European Patent Office Re. Application No. 09787476.2.
Patent Examination Report Dated Apr. 12, 2013 From the Australian Government, IP Australia Re. Application No. 2009275135.
Examination Report Dated May 15, 2013 From the Government of India, Patent Office, Intellectual Property Building Re. Application No. 319/MUMNP/2011.

* cited by examiner

*Primary Examiner* — Tsang Cecilia
*Assistant Examiner* — Mindy Newman

(57) ABSTRACT

Provided are angiopoietin-derived peptides or homologs or derivatives thereof, pharmaceutical composition including them, a use thereof for therapy and for the manufacture of a medicament, a method of treating a wide range of conditions, disorders and diseases therewith, nucleotide sequences encoding them, antibodies directed to epitopes thereof and fusion proteins including them.

17 Claims, 9 Drawing Sheets

Figure 2C

ANGIOPOIETIN DERIVED PEPTIDES

This is a National Phase Application filed under 35 U.S.C. 371 as a national stage of PCT/IL2009/000709, filed on Jul. 20, 2009, an application claiming the benefit under 35 USC 119(e) of U.S. Provisional Application No. 61/129,806, filed on Jul. 21, 2008, the content of each of which is hereby incorporated by reference in its entirety.

The Sequence Listing submitted in text format (.txt) on Apr. 14, 2011, named "SequenceListing.txt", (created on Thursday, Feb. 24, 2011, 79.5 KB), is incorporated herein by reference.

FIELD OF THE INVENTION

This invention relates to the field of angiogenesis related pathology.

BACKGROUND OF THE INVENTION

Angiogenesis, the process of new blood-vessel growth, plays an essential role in many physiological and pathological processes. It is a multi-step process including endothelial cell activation, proliferation, migration, penetration of extracellular matrix, reorganization of cells into tubules, formation of a lumen, and anastomosis. Typically, angiogenesis is tightly regulated by pro- and anti-angiogenic factors and is crucial for development, reproduction and repair. Vasculogenesis and angiogenesis are down-regulated in the healthy adult and are—except for the organs of the female reproductive system—almost exclusively associated with pathology when angiogenesis is induced by microenvironmental factors (e.g. hypoxia or inflammation). Pathological processes associated with, or induced by, angiogenesis include diseases as diverse as cancer, and inflammatory disorders such as rheumatoid or rheumatic inflammatory disease, especially arthritis (including rheumatoid arthritis), or other chronic inflammatory disorders, such as chronic asthma, arterial or post-transplantational atherosclerosis, psoriasis, asthma, infections, obesity, diabetes, endometriosis, ocular neovascularisation, such as retinopathies (including diabetic retinopathy), macular degeneration, thrombosis, hemangioblastoma, and hemangioma (Folkman J., 2007 *Nat Rev Drug Discov* 6(4):273; Fiedler U. and Augustin H. G. 2006 *TRENDS Immun* 27(12):552; Li L., et al, 2005 *Pediatr Endocrinol Rev.* 2(3):399) Although a variety of factors can modulate endothelial cell (EC) responses in vitro, and blood vessel growth in vivo, only vascular endothelial growth factor (VEGF) family members and the angiopoietins are believed to act almost exclusively on vascular ECs. (Yancopoulos G., et al, 2000 *Nature* 407:242).

The formation of functional vasculature is a complex process requiring spatial and temporal coordination of multiple angiogenic factors, receptors, intracellular signaling pathways and regulatory factors. Without being bound by theory, vascular endothelial growth factors (VEGFs) and angiopoietins (Angs) play complementary roles in this process. The Ang family comprises the ligands Ang1, Ang2, Ang3, and Ang4. Their cognate Tie2/Tek receptor and a closely related orphan receptor, Tie1, are almost exclusively expressed by endothelial cells and hematopoietic stem cells. Tie1 and Tie2 share a similar overall structure consisting of an extracellular domain and an intracellular tyrosine kinase domain. (Shim W. S. N., et al, 2007 *Mol Cancer Res* 5(7):655; Fiedler U. and Augustin H. G., 2006 *TRENDS Immun* 27(12):552).

The Angs contain an amino-terminal angiopoietin specific domain, a coiled-coil domain, a linker peptide and a carboxy-terminal fibrinogen homology domain. The fibrinogen homology domain is responsible for receptor binding, the coiled-coil domain is required for dimerization of angiopoietin monomers, and the short amino-terminal region forms ring-like structures that cluster dimers into variable sized multimers necessary for Tie2 activation. (Eklund L. and Olsen B. R, 2006 *Exp Cell Res* 312:630)

Ang1 is known to form trimers and multimers to homodimerize and induce tyrosine phosphorylation of the Tie2 receptor for intracellular signaling. Dimeric form of Ang1 has been found to inactivate Tie2 receptor, and some isoforms of Ang1 have been reported to negatively regulate Tie2 activation (Shim W. S. N., et al, 2007 *Mol Cancer Res* 5(7):655). Ang1 binding to the extracellular domain of Tie2 results in receptor dimerization, allowing activation of the kinase domain and autophosphorylation of specific tyrosine residues, acting as docking sites for a number of effectors that couple the activated receptors to the cytoplasmic signaling pathways. Ang1-stimulated Tie2 activation mediates remodeling and stabilization of cell-cell and cell-matrix interactions and plays a role in the recruitment of peri-endothelial mesenchymal cells to the vessels. In addition, Ang1 has anti-permeability and anti-inflammatory functions, and is also critically important in the formation of vascular networks during developmental angiogenesis (Eklund L. and Olsen B. R, 2006 *Exp Cell Res* 312:630; Shim W. S. N., et al, 2007 *Mol Cancer Res* 5(7):655).

Ang2 forms dimers to bind to Tie2, but does not induce autophosphorylation. In contrast to Ang1, it is almost exclusively expressed by endothelial cells. Ang2 mRNA is almost undetectable in the quiescent vasculature, however, it is induced dramatically at sites of endothelial cell activation and vascular remodeling. Ang2 expression is induced by various cytokines, including VEGF and fibroblast growth factor (FGF-2), and by microenvironmental factors. Ang2 is upregulated together with VEGF-A at sites of angiogenic sprouting, whereas reduced VEGF-A expression relative to Ang2 is associated with vascular regression. (Eklund L. and Olsen B. R, 2006 *Exp Cell Res* 312:630; Shim W. S. N., et al, 2007 *Mol Cancer Res* 5(7):655).

Ang1-mediated Tie2 signaling functions as the default pathway to control vascular quiescence. Ang1 exerts a protective effect on the endothelium and limits its ability to be activated by exogenous cytokines, thus controls vascular homeostasis and endothelial activation. Proper vascular homeostasis is tightly controlled by balanced Tie2 signaling. Ang2 expression is tightly controlled as well. The release of Ang2 results in rapid destabilization of the endothelium. Moreover, Ang2 triggers an inflammatory response by activating the endothelium and inducing permeability. (Fiedler U and Augustin H. G., 2006 *TRENDS Immun* 27(12):552).

Ang3 and Ang4 are not well studied but are believed to be interspecies orthologues between mouse and human, respectively (Valenzuela D M, et al, 1999 *Proc Natl Acad Sci USA* 96:1904-9). The function of Ang3 and Ang4 in angiogenesis is controversial compared with the more established members of the family. Ang3 has been reported to act as antagonist that interfers with Ang1 activation of Tie2 and Akt in tumor growth. However, Ang3 was found to strongly activate mouse Tie2, but not its human counterpart, whereas Ang4 did not display species selectivity in Tie2 activation (Shim W. S. N., et al, 2007 *Mol Cancer Res* 50:655).

Angiogenic inhibitors are being vigorously pursued. Currently, several angiogenic inhibitors including bevacizumab (Avastin), thalidomide (Thalomid), lenalidomide (Revlimid), ranibizumab (Lucentis), sutinib (Sutent), sorafenib (Nexavar), and pegaptanib (Macugen) are in clinical use. Several angiogenic inhibitors including bevasiranib, AGN-211745, TG-100801, volociximab, ATG-003, relimid, RTP-801i-14, aflibercept, apremilast, INGN-241, angiostatin, endostatin are in clinical trials and many others are in development. The anti-angiogenic compounds developed include monoclonal antibodies or antibody fragments (e.g. bevacizumab, ranibizumab, and volociximab), aptamers (e.g. pegaptanib and E-10030), small-molecules (e.g. thalidomide, ATG-003, TG-100801, pazopanib, vandetanib, lenalidomide, and cediranib), gene therapy (e.g. angistat, advexin, and INGN-241), recombinant proteins (e.g. aflibercept, ABT-828, and replistatin), small interfering RNA (siRNA, e.g. AGN-211745 and bevasiranib), and peptides (e.g. ABT-510, angiostatin, endostatin).

However, as in all technologies in all times, there is an ongoing need for new improved compounds having anti-angiogenic activity.

SUMMARY OF THE INVENTION

In at least some embodiments, the subject invention now provides novel peptides corresponding to segments of Ang1, Ang2, and Ang4, homologs thereof, orthologs thereof, derivatives thereof, antibodies directed thereto, and fusion proteins comprising them, all of which have a therapeutic value for a wide range of conditions, disorders and diseases.

According to some embodiments of the present invention the conditions, disorders and diseases are conditions, disorders and diseases where treatment or prevention of undesired angiogenesis can be of therapeutic value. Such conditions, disorders and diseases include, but are not limited to cancer, respiratory diseases, metabolic disorders, fibrotic and connective tissue related conditions, urogenital disorders, ocular diseases, vascular anomalies, cardiovascular diseases and their complications, inflammatory conditions associated with an infection, inflammatory disorders, chronic inflammatory diseases, autoimmune diseases, bone disease or bone-related disorder and pain. Other diseases associated with undesired angiogenesis will be apparent to those skilled in the art.

In at least some embodiments, the subject invention thus provides a peptide consisting essentially of an amino acid sequence LKEEKENLQGLVTRQTYIIQELEKQLNRAT (CGEN-H2 [SEQ ID NO: 1]) or a homolog or a derivative thereof.

In at least some embodiments, the subject invention further provides a peptide consisting essentially of an amino acid sequence TNNSVLQKQQL (CGEN-H3 [SEQ ID NO: 2]) or a homolog or a derivative thereof.

In at least some embodiments, the subject invention further provides a peptide consisting essentially of an amino acid sequence LMDTVHNLVNL (CGEN-A8 [SEQ ID NO: 3]) or a homolog or a derivative thereof.

In at least some embodiments, the subject invention further provides a peptide consisting essentially of an amino acid sequence NEILKIHEKNSLLEHKILEMEGKHK (CGEN-H7 [SEQ ID NO: 4]) or a homolog or a derivative thereof.

In at least some embodiments, the subject invention further provides a peptide consisting essentially of an amino acid sequence QLQVLVSKQNSIIEEL (CGEN-G4 [SEQ ID NO: 5]) or a homolog or a derivative thereof.

In at least some embodiments, the subject invention further provides a peptide consisting essentially of an amino acid sequence DLMETVNNLLTMMSTSNSAKD (CGEN-G6 [SEQ ID NO: 6]) or a homolog or a derivative thereof.

In at least some embodiments, the subject invention further provides a peptide consisting essentially of an amino acid sequence QEELASILSKKAKLLNTLSRQSAALTNIERGLRGVR (CGEN-F9 [SEQ ID NO: 7]) or a homolog or a derivative thereof.

In at least some embodiments, the subject invention further provides a peptide consisting essentially of an amino acid sequence QHSLRQLLVLLRHLVQERANASA (CGEN-F12 [SEQ ID NO: 8]) or a homolog or a derivative thereof.

In at least some embodiments, the subject invention further provides a peptide consisting essentially of an amino acid sequence TDMEAQLLNQTSRMDAQM (CGEN-C6 [SEQ ID NO: 9]) or a homolog or a derivative thereof.

In at least some embodiments, the subject invention further provides a peptide consisting essentially of an amino acid sequence ETFLSTNKLENQ (CGEN-A11 [SEQ ID NO: 10]) or a homolog or a derivative thereof.

In at least some embodiments, the subject invention further provides a peptide consisting essentially of an amino acid sequence TQQVKQLEQALQNNTQWLKKLERAIKTIL (CGEN-G2 [SEQ ID NO: 11]) or a homolog or a derivative thereof.

In at least some embodiments, the subject invention further provides a homolog of a CGEN-H2 peptide consisting essentially of an amino acid sequence EGKHKEELDTLKEEKENLQGLVTRQTYIIQELEKQLNRATTNNSVLQKQQ [SEQ ID NO: 12] or a derivative thereof.

In at least some embodiments, the subject invention further provides a homolog of a CGEN-H3 peptide consisting essentially of an amino acid sequence QELEKQLNRATTNNSVLQKQQLELMDTVHNLV [SEQ ID NO: 13] or a derivative thereof.

In at least some embodiments, the subject invention further provides a homolog of a CGEN-A8 peptide consisting essentially of an amino acid sequence NSVLQKQQLELMDTVHNLVNLCTKEGVLLKG [SEQ ID NO: 14] or a derivative thereof.

In at least some embodiments, the subject invention further provides a homolog of a CGEN-H7 peptide consisting essentially of an amino acid sequence KLEKQLLQQTNEILKIHEKNSLLEHKILEMEGKHKEELDTLKEEK [SEQ ID NO: 15] or a derivative thereof.

In at least some embodiments, the subject invention further provides a homolog of a CGEN-G4 peptide consisting essentially of an amino acid sequence QLQSIKEEKDQLQVLVSKQNSIIEELEKKIVTATVN [SEQ ID NO: 16] or a derivative thereof.

In at least some embodiments, the subject invention further provides a homolog of a CGEN-G6 peptide consisting essentially of an amino acid sequence NNSVLQKQQHDLMETVNNLLTMMSTSNSAKDPTVAKEEQIS [SEQ ID NO: 17] or a derivative thereof.

In at least some embodiments, the subject invention further provides a homolog of a CGEN-F9 peptide consisting essentially of an amino acid sequence KRLQALETKQQEELASILSKKAKLLNTLSRQSAALTNIERGLRGVRHNSSLLQDQ Q [SEQ ID NO: 18] or a derivative thereof.

In at least some embodiments, the subject invention further provides a homolog of a CGEN-F12 peptide consisting essentially of an amino acid sequence RHNSSLLQDQQHSLRQLLVLLRHLVQERANASAPAFIMAGEQV [SEQ ID NO: 19] or a derivative thereof.

In at least some embodiments, the subject invention further provides a homolog of a CGEN-C6 peptide consisting essentially of an amino acid sequence NQTTAQIRKLTDMEAQLLNQTSRMDAQMPETFLSTNKL [SEQ ID NO: 20] or a derivative thereof.

In at least some embodiments, the subject invention further provides a homolog of a CGEN-A11 peptide consisting essentially of an amino acid sequence QTSRMDAQMPETFLSTNKLENQLLLQRQKLQQ [SEQ ID NO: 21] or a derivative thereof.

In at least some embodiments, the subject invention further provides a homolog of a CGEN-G2 peptide consisting essentially of an amino acid sequence ANPLHLGKLPTQQVKQLEQALQNNTQWLKKLERAIKTILRSKLEQVQQQ [SEQ ID NO: 22] or a derivative thereof.

In at least some embodiments, the subject invention further provides a peptide consisting essentially of an amino acid sequence corresponding to a homolog of a peptide according to at least some embodiments of the present invention, consisting essentially of an amino acid sequence as set forth in any one of SEQ ID NOs: 63-186.

In at least some embodiments, the subject invention further provides a peptide consisting essentially of an amino acid sequence corresponding to a partner helix of a peptide of at least some embodiments of the present invention.

In at least some embodiments, the subject invention further provides a partner helix peptide consisting essentially of an amino acid sequence as set forth in any one of SEQ ID NOs: 48-62.

In at least some embodiments, the subject invention also provides an antibody that selectively binds to an epitope in a peptide as set forth in any one of SEQ ID NOs: 1-22, 48-186.

In at least some embodiments, the subject invention further provides a conjugate or fusion protein comprising a peptide as set forth in any one of SEQ ID NOs: 1-22, 48-186.

In at least some embodiments, the subject invention further provides a pharmaceutical composition comprising a peptide or a homolog thereof or a derivative thereof, an antibody of the invention or a fusion protein of the invention and a pharmaceutically acceptable carrier. In at least some embodiments, the subject invention further envisages a peptide of the invention or a homolog or a derivative thereof, an antibody or a fusion protein for use in therapy and further envisages a use of a peptide as described herein or a homolog or a derivative thereof, and/or an antibody or a fusion protein for the manufacture of a medicament.

In at least some embodiments, the subject invention further provides a method of treating cancer comprising administering a pharmaceutically effective amount of one or more of a peptide as described herein or a homolog thereof or a derivative thereof, an antibody or a fusion protein as described herein, and a pharmaceutically acceptable carrier, to a subject in need thereof.

In at least some embodiments, the subject invention further provides a method of treating respiratory disease comprising administering a pharmaceutically effective amount of a peptide according to at least some embodiments of the present invention or a homolog thereof or a derivative thereof, an antibody according to at least some embodiments of the present invention, or a fusion protein according to at least some embodiments of the present invention and a pharmaceutically acceptable carrier to a subject in need thereof.

In at least some embodiments, the subject invention further provides a method of treating a metabolic disorder comprising administering a pharmaceutically effective amount of a peptide according to at least some embodiments of the present invention or a homolog thereof or a derivative thereof, an antibody according to at least some embodiments of the present invention, or a fusion protein according to at least some embodiments of the present invention and a pharmaceutically acceptable carrier to a subject in need thereof.

In at least some embodiments, the subject invention further provides a method of treating a fibrotic or connective tissue related condition comprising administering a pharmaceutically effective amount of a peptide according to at least some embodiments of the present invention or a homolog thereof or a derivative thereof, an antibody according to at least some embodiments of the present invention, or a fusion protein according to at least some embodiments of the present invention and a pharmaceutically acceptable carrier to a subject in need thereof.

In at least some embodiments, the subject invention further provides a method of treating a urogenital related disorder comprising administering a pharmaceutically effective amount of a peptide according to at least some embodiments of the present invention or a homolog thereof or a derivative thereof, an antibody according to at least some embodiments of the present invention, or a fusion protein according to at least some embodiments of the present invention and a pharmaceutically acceptable carrier to a subject in need thereof.

In at least some embodiments, the subject invention further provides a method of treating an ocular disease comprising administering a pharmaceutically effective amount of a peptide according to at least some embodiments of the present invention or a homolog thereof or a derivative thereof, an antibody according to at least some embodiments of the present invention, or a fusion protein according to at least some embodiments of the present invention and a pharmaceutically acceptable carrier to a subject in need thereof.

In at least some embodiments, the subject invention further provides a method of treating a vascular anomaly comprising administering a pharmaceutically effective amount of a peptide according to at least some embodiments of the present invention or a homolog thereof or a derivative thereof, an antibody according to at least some embodiments of the present invention, or a fusion protein according to at least some embodiments of the present invention and a pharmaceutically acceptable carrier to a subject in need thereof.

In at least some embodiments, the subject invention further provides a method of treating a cardiovascular disease comprising administering a pharmaceutically effective amount of a peptide according to at least some embodiments of the present invention or a homolog thereof or a derivative thereof, an antibody according to at least some embodiments of the present invention, or a fusion protein according to at least some embodiments of the present invention and a pharmaceutically acceptable carrier to a subject in need thereof.

In at least some embodiments, the subject invention further provides a method of treating an inflammatory condition associated with an infection or an inflammatory disorder comprising administering a pharmaceutically effective amount of a peptide according to at least some embodiments of the present invention or a homolog thereof or a derivative thereof, an antibody according to at least some embodiments of the present invention, or a fusion protein according to at least some embodiments of the present invention and a pharmaceutically acceptable carrier to a subject in need thereof.

In at least some embodiments, the subject invention further provides a method of treating a chronic inflammatory or autoimmune disease comprising administering a pharmaceutically effective amount of a peptide according to at least some embodiments of the present invention or a homolog thereof or a derivative thereof, an antibody according to at least some embodiments of the present invention, or a fusion protein according to at least some embodiments of the present invention and a pharmaceutically acceptable carrier to a subject in need thereof.

In at least some embodiments, the subject invention further provides a method of treating a bone disease or bone-related disorder comprising administering a pharmaceutically effective amount of a peptide according to at least some embodiments of the present invention or a homolog thereof or a derivative thereof, an antibody according to at least some embodiments of the present invention, or a fusion protein according to at least some embodiments of the present invention and a pharmaceutically acceptable carrier to a subject in need thereof.

In at least some embodiments, the subject invention further provides a method of treating and managing pain comprising administering a pharmaceutically effective amount of a peptide according to at least some embodiments of the present invention or a homolog thereof or a derivative thereof, an antibody according to at least some embodiments of the present invention, or a fusion protein according to at least some embodiments of the present invention and a pharmaceutically acceptable carrier to a subject in need thereof.

In at least some embodiments, the subject invention also provides nucleotide sequences encoding a peptide according to at least some embodiments of the present invention or a homolog thereof.

All amino acid sequences and/or nucleic acid sequences shown herein as embodiments of the present invention relate to their isolated form.

The terms "polypeptide," "peptide" and "protein" are used interchangeably herein to refer to a polymer of amino acid residues. The terms encompass any peptide (including cyclic peptides) or protein comprising two or more amino acids joined to each other by peptide bonds or modified peptide bonds. "Polypeptide" refers to both short chains, commonly referred to as peptides, oligopeptides or oligomers, and to longer chains, generally referred to as proteins.

"Polypeptides" include amino acid sequences modified either by natural processes, or by chemical modification techniques which are well known in the art. Modifications may occur anywhere in a polypeptide, including the peptide backbone, the amino acid side-chains, and the amino or carboxyl termini. Polypeptides can be modified, e.g., by the addition of carbohydrate residues to form glycoproteins. The terms "polypeptide," "peptide" and "protein" include glycoproteins, as well as non-glycoproteins.

The terms "conjugate" and "fusion protein" and any lingual derivatives thereof are interchangeably used herein.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 2: shows a multiple alignment of examples of homologous sequences of peptides according to at least some embodiments of the present invention, derived from various organisms. Rectangles show the comparison blocks for peptides of the invention with amino acid residue numbering according to the human sequence.

FIG. 2C shows a multiple alignment comparison of the sequence of CGEN-F9 (SEQ ID NO: 7), CGEN-F12 (SEQ ID NO: 8), CGEN-C6 (SEQ ID NO: 9), CGEN-A11 (SEQ ID NO: 10), CGEN-G2 (SEQ ID NO: 11) corresponding to amino acid residues 210-245, 255-277, 150-167, 169-180, 84-112 respectively of the angiopoietin 4 protein sequence (SEQ ID NO: 47), and homologous sequences derived from Macaca mulatta (gi|109092550), Bos Taurus (gi|115497116), Mus musculus (gi|6753006), Rattus norvegicus (gi|157820699), Canis lupus familiaris (gi|73992066).

FIG. 3 demonstrates identification of helix-helix interactions using a unique computerized method. FIG. 3A presents the residue-residue contact map, corresponding to the two anti-parallel helices taken from BAG-1.

FIG. 7 demonstrates the effect of CGEN-A11 (SEQ ID NO: 10) on in vivo angiogenesis in rat model of oxygen-induced retinopathy (OIR).

DETAILED DESCRIPTION OF THE INVENTION

Figure 1:
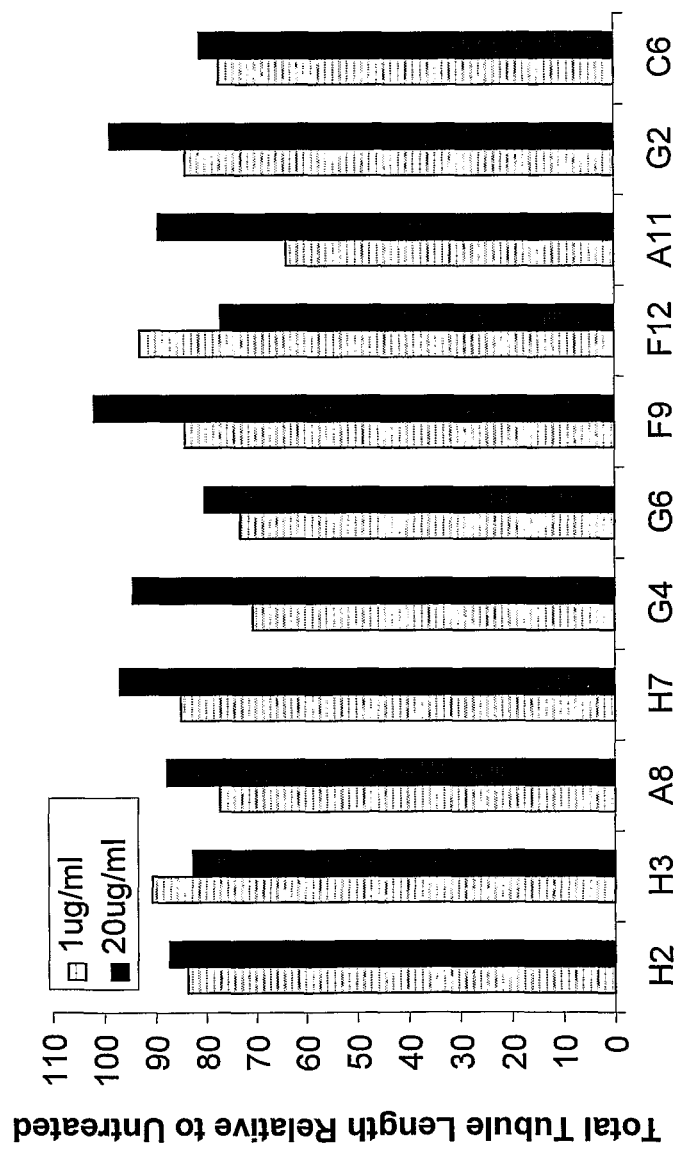
FIG. 1 demonstrates the effect of 1 and 20 µg/mL of CGEN-H2 (SEQ ID NO: 1), CGEN-H3 (SEQ ID NO: 2), CGEN-A8 (SEQ ID NO: 3), CGEN-H7 (SEQ ID NO: 4), CGEN-G4 (SEQ ID NO: 5), CGEN-G6 (SEQ ID NO: 6), CGEN-F9 (SEQ ID NO: 7), CGEN-F12 (SEQ ID NO: 8), CGEN-C6 (SEQ ID NO: 9), CGEN-A11 (SEQ ID NO: 10), and CGEN-G2 (SEQ ID NO: 11) on in vitro angiogenesis using AngioKit (TCS Cellworks, UK) compared to untreated (UT).

In at least some embodiments, the subject invention provides a peptide consisting essentially of an amino acid sequence LKEEKENLQGLVTRQTYIIQELEKQLNRAT (CGEN-H2 [SEQ ID NO: 1]) or a homolog or a derivative thereof. CGEN-H2 corresponds to amino acid residues 212-241 of the angiopoietin 1 protein sequence (GenBank Accession number: gi|20532340, SEQ ID NO: 45).

In at least some embodiments, the subject invention further provides a peptide consisting essentially of an amino acid sequence TNNSVLQKQQL (CGEN-H3 [SEQ ID NO: 2]) or a homolog or a derivative thereof. CGEN-H3 corresponds to amino acid residues 242-252 of the angiopoietin 1 protein sequence (GenBank Accession number: gi|20532340, SEQ ID NO: 45).

In at least some embodiments, the subject invention further provides a peptide consisting essentially of an amino acid sequence LMDTVHNLVNL (CGEN-A8 [SEQ ID NO: 3]) or a homolog or a derivative thereof. CGEN-A8 corresponds to amino acid residues 254-264 of the angiopoietin 1 protein sequence (GenBank Accession number: gi|20532340, SEQ ID NO: 45).

In at least some embodiments, the subject invention further provides a peptide consisting essentially of an amino acid sequence NEILKIHEKNSLLEHKILEMEGKHK (CGEN-H7 [SEQ ID NO: 4]) or a homolog or a derivative thereof. CGEN-H7 corresponds to amino acid residues 182-206 of the angiopoietin 1 protein sequence (GenBank Accession number: gi|20532340, SEQ ID NO: 45).

In at least some embodiments, the subject invention further provides a peptide consisting essentially of an amino acid sequence QLQVLVSKQNSIIEEL (CGEN-G4 [SEQ ID NO: 5]) or a homolog or a derivative thereof. CGEN-G4 corresponds to amino acid residues 215-230 of the angiopoietin 2 protein sequence (GenBank Accession number: gi|4557315, SEQ ID NO: 46).

In at least some embodiments, the subject invention further provides a peptide consisting essentially of an amino acid sequence DLMETVNNLLTMMSTSNSAKD (CGEN-G6 [SEQ ID NO: 6]) or a homolog or a derivative thereof. CGEN-G6 corresponds to amino acid residues 250-270 of the angiopoietin 2 protein sequence (GenBank Accession number: gi|4557315, SEQ ID NO: 46).

In at least some embodiments, the subject invention further provides a peptide consisting essentially of an amino acid sequence QEELASILSKKAKLLNTLSRQSAALTNIERGLRGVR (CGEN-F9 [SEQ ID NO: 7]) or a homolog or a derivative thereof. CGEN-F9 corresponds to amino acid residues 210-245 of the angiopoietin 4 protein sequence (GenBank Accession number: gi|7705276, SEQ ID NO: 47).

In at least some embodiments, the subject invention further provides a peptide consisting essentially of an amino acid sequence QHSLRQLLVLLRHLVQERANASA (CGEN-F12 [SEQ ID NO: 8]) or a homolog or a derivative thereof. CGEN-F12 corresponds to amino acid residues 255-277 of the angiopoietin 4 protein sequence (GenBank Accession number: gi|7705276, SEQ ID NO: 47).

In at least some embodiments, the subject invention further provides a peptide consisting essentially of an amino acid sequence TDMEAQLLNQTSRMDAQM (CGEN-C6 [SEQ ID NO: 9]) or a homolog or a derivative thereof. CGEN-C6 corresponds to amino acid residues 150-167 of the angiopoietin 4 protein sequence (GenBank Accession number: gi|7705276, SEQ ID NO: 47).

In at least some embodiments, the subject invention further provides a peptide consisting essentially of an amino acid sequence ETFLSTNKLENQ (CGEN-A11 [SEQ ID NO: 10]) or a homolog or a derivative thereof. CGEN-A11 corresponds to amino acid residues 169-180 of the angiopoietin 4 protein sequence (GenBank Accession number: gi|7705276, SEQ ID NO: 47).

In at least some embodiments, the subject invention further provides a peptide consisting essentially of an amino acid sequence TQQVKQLEQALQNNTQWLKKLERAIKTIL (CGEN-G2 [SEQ ID NO: 11]) or a homolog or a derivative thereof. CGEN-G2 corresponds to amino acid residues 84-112 of the angiopoietin 4 protein sequence (GenBank Accession number: gi|7705276, SEQ ID NO: 47).

Homologs, Orthologs, Derivatives and Other Modifications or Changes

Without wishing to be limited in any way, according to at least some embodiments of the present invention there is provided one or more homologs, orthologs, derivatives and other modifications or changes to peptide sequences as described herein. Some non-limiting, illustrative examples are provided below.

The term "homolog" relating to a peptide according to at least some embodiments of the present invention as used herein should be understood to encompass a peptide which has substantially the same amino acid sequence and substantially the same biological activity as CGEN-H2, CGEN-H3, CGEN-A8, CGEN-H7, CGEN-G4, CGEN-G6, CGEN-F9, CGEN-F12, CGEN-C6, CGEN-A11, or CGEN-G2, respectively. Thus, a homolog may differ from the CGEN-H2, CGEN-H3, CGEN-A8, CGEN-H7, CGEN-G4, CGEN-G6, CGEN-F9, CGEN-F12, CGEN-C6, CGEN-A11, or CGEN-G2 peptides by the addition, deletion or substitution of one or more amino acid residues or combinations thereof, provided that the resulting peptide retains the biological activity of CGEN-H2, CGEN-H3, CGEN-A8, CGEN-H7, CGEN-G4, CGEN-G6, CGEN-F9, CGEN-F12, CGEN-C6, CGEN-A11, or CGEN-G2, respectively. Persons skilled in the art can readily determine which amino acid residues may be added, deleted or substituted (including with which amino acids such substitutions may be made) using established well known procedures. Examples of homologs of CGEN-H2, CGEN-H3, CGEN-A8, CGEN-H7, CGEN-G4, CGEN-G6, CGEN-F9, CGEN-F12, CGEN-C6, CGEN-A11, or CGEN-G2 are deletion homologs containing less than all the amino acid residues of CGEN-H2, CGEN-H3, CGEN-A8, CGEN-H7, CGEN-G4, CGEN-G6, CGEN-F9, CGEN-F12, CGEN-C6, CGEN-A11, or CGEN-G2, substitution homologs wherein one or more amino acid residues specified are replaced by other amino acid residues (e.g. amino acid with similar properties or by D-amino acids, or by non-natural amino acids) and addition homologs wherein one or more amino acid residues are added to a terminal or medial portion of CGEN-H2, CGEN-H3, CGEN-A8, CGEN-H7, CGEN-G4, CGEN-G6, CGEN-F9, CGEN-F12, CGEN-C6, CGEN-A11, or CGEN-G2 respectively, all of which share the biological activity of CGEN-H2, CGEN-H3, CGEN-A8, CGEN-H7, CGEN-G4, CGEN-G6, CGEN-F9, CGEN-F12, CGEN-C6, CGEN-A11, or CGEN-G2, respectively.

A substituted or inserted amino acid residue may or may not be encoded by the genetic code. A homolog of a polypeptide may be naturally occurring such as an allelic homolog, or may be a homolog that is not known to occur naturally. Non-naturally occurring homologs of polypeptides may be prepared by mutagenesis techniques or by direct synthesis.

Generally, the homolog differs from the reference polypeptide by conservative amino acid substitutions.

A "conservative amino acid substitution" may involve a substitution of a native amino acid residue with a normative residue such that there is little or no effect on the polarity or charge of the amino acid residue at that position. Desired amino acid substitutions (whether conservative or non-conservative) can be determined by those skilled in the art. For example, amino acid substitutions can be used to identify important residues of the peptide sequence, or to increase or decrease the affinity of the peptide.

Naturally occurring residues may be divided into classes based on common side chain properties: An "acidic residue" refers to amino acid residues in D- or L-form having sidechains comprising acidic groups; "amide residue" refers to amino acids in D- or L-form having sidechains comprising amide derivatives of acidic groups; "aromatic residue" refers to amino acid residues in D- or L-form having sidechains comprising aromatic groups; "basic residue" refers to amino acid residues in D- or L-form having sidechains comprising basic groups; "hydrophilic residue" refers to amino acid residues in D- or L-form having sidechains comprising polar groups; "nonfunctional residue" refers to amino acid residues in D- or L-form having sidechains that lack acidic, basic, or aromatic groups; "neutral polar residue" refers to amino acid residues in D- or L-form having sidechains that lack basic, acidic, or polar groups; "polar hydrophobic residue" refers to amino acid residues in D- or L-form having sidechains comprising polar groups; "hydrophobic residue" refers to amino acid residues in D- or L-form having sidechains that lack basic or acidic groups.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. In making such changes, according to certain embodiments, the hydropathic index of amino acids may be considered. Each amino acid has been assigned a hydropathic index on the basis of its hydrophobicity and charge characteristics. It is known that certain amino acids may be substituted for other amino acids having a similar hydropathic index or score and still retain substantially the same biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments. In certain embodiments, the greatest local average hydrophilicity of a protein, as governed by the hydrophilicity of its adjacent amino acids, correlates with its immunogenicity and antigenicity, i.e., with a biological property of the protein.

In making changes based upon similar hydrophilicity values, the substitution of amino acids whose hydrophilicity values are within ±2 is included, in certain embodiments, those that are within ±1 are included, and in certain embodiments, those within ±0.5 are included.

One may also identify epitopes from primary amino acid sequences on the basis of hydrophilicity. These regions are also referred to as "epitopic core regions." Examples of conservative substitutions include the substitution of one nonpolar (hydrophobic) amino acid residue such as isoleucine, valine, leucine norleucine, alanine, or methionine for another, the substitution of one polar (hydrophilic) amino acid residue for another such as between arginine and lysine, between glutamine and asparagine, between glycine and serine, the substitution of one basic amino acid residue such as lysine, arginine or histidine for another, or the substitution of one acidic residue, such as aspartic acid or glutamic acid for another. The phrase "conservative amino acid substitution" also includes the use of a chemically derivatized residue in place of a non-derivatized residue, provided that such polypeptide displays substantially the same biological activity.

In other examples, a peptide homolog sequence, modified from the original peptide amino acid sequence includes at least one amino acid residue inserted or substituted therein, relative to the amino acid sequence of the original peptide sequence of interest, in which the inserted or substituted amino acid residue has a side chain comprising a nucleophilic or electrophilic reactive functional group by which the peptide is conjugated to a linker or half-life extending moiety. Examples of such a nucleophilic or electrophilic reactive functional group include, but are not limited to, a thiol, a primary amine, a seleno, a hydrazide, an aldehyde, a carboxylic acid, a ketone, an aminooxy, a masked (protected) aldehyde, or a masked (protected) keto functional group.

Examples of amino acid residues having a side chain comprising a nucleophilic reactive functional group include, but are not limited to, a lysine residue, a diaminopropionic acid residue, a diaminobutyric acid residue, an ornithine residue, a cysteine, a homocysteine, a glutamic acid residue, an aspartic acid residue, or a selenocysteine residue. For example, the original peptide amino acid sequence (or "primary sequence") can be modified at one, two, three, four, five or more amino acid residue positions, by having a residue substituted therein different from the primary sequence or omitted.

In certain embodiments of the present invention, amino acid substitutions encompass, non-canonical amino acid residues, which include naturally rare (in peptides or proteins) amino acid residues or unnatural amino acid residues (See, e.g., Link et al., *Non-canonical amino acids in protein engineering, Current Opinion in Biotechnology*, 14(6):603-609 (2003)). The term "non-canonical amino acid residue" refers to amino acid residues in D- or L-form that are not among the 20 canonical amino acids generally incorporated into naturally occurring proteins, for example, homoamino acids, cyclic amino acids and amino acids with derivatized side chains. Examples include (in the L-form or D-form; abbreviated as in parentheses): citrulline (Cit), homocitrulline (hCit), -methylcitrulline (NMeCit), -methylhomocitrulline (-MeHoCit), ornithine (Orn), -Methylornithine (-MeOrn or NMeOm), sarcosine (Sar), homolysine (hLys or hK), homoarginine (hArg or hR), homoglutamine (hQ), -methylarginine (NMeR), -methylleucine (-MeL or NMeL), N-methylhomolysine (NMeHoK), -methylglutamine (NMeQ), norleucine (Nle), norvaline (Nva), 1,2,3,4-tetrahydroisoquinoline (Tic), Octahydroindole-2-carboxylic acid (Oic), 3-{1-naphthyl)alanine (1-NaI), 3-(2-naphthyl)alanine (2-NaI), 1,2,3,4-tetrahydroisoquinoline (Tic), 2-indanylglycine (IgI), para-iodophenylalanine (pI-Phe), para-aminophenylalanine (4AmP or 4-Amino-Phe), 4-guanidino phenylalanine (Guf), 5 glycyllysine (abbreviated herein "K(-glycyl)"

or "K(glycyl)" or "K(gly)"), nitrophenylalanine (nitrophe), aminophenylalanine (aminophe or Amino-Phe), benzylphenylalanine (benzylphe), -carboxyglutamic acid (-carboxyglu), hydroxyproline (hydroxypro), p-carboxyl-phenylalanine (Cpa),;-aminoadipic acid (Aad), -methyl valine (NMeVal),;-methyl leucine (NMeLeu),;-methylnorleucine (NMeNle), cyclopentylglycine (Cpg), cyclohexylglycine (Chg), acetylarginine 0 (acetylarg), ;-diaminopropionoic acid (Dpr),;-diaminobutyric acid (Dab), diaminopropionic acid (Dap), cyclohexylalanine (Cha), 4-methyl-phenylalanine (MePhe),;-diphenyl-alanine (BiPhA), aminobutyric acid (Abu), 4-phenyl-phenylalanine (or biphenylalanine; 4Bip), ;-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxyzine, allo-hydroxylysine, isodesmosine, allo-isoleucine, N-methylglycine, N-methylisoleucine, N-methylvaline, 4-hydroxyproline (Hyp), -carboxyglutamate,;-N,N,N-trimethyllysine,;-N-acetyllysine, O-phosphoserine, N-acetylserine, N-formylmethionine, 3-methylhistidine, 5-hydroxylysine, -methylarginine, 4-Amino-O-Phthalic Acid (4APA), and other similar amino acids, and derivatized forms of any of these.

Among useful peptide homolog sequences (but without wishing to be limited in any way) are homolog sequences that introduce amino acid residues that can form an intramolecular covalent bridge (e.g., a disulfide bridge) or non-covalent interactions (e.g. hydrophobic, ionic, stacking) which may enhance the stability of the structure of the unconjugated or conjugated (e.g., PEGylated) peptide homolog molecule.

In one embodiment, a homolog of a CGEN-H2 peptide according to at least some embodiments of the present invention is EGKHKEELDTLKEEKENLQGLVTRQTYIIQELEKQLNRATTNNSVLQKQQ [SEQ ID NO: 12] which corresponds to amino acid residues 202-251 of angiopoietin 1 protein sequence (GenBank Accession number: gi|20532340) or a derivative thereof.

In another embodiment, a homolog of a CGEN-H3 peptide according to at least some embodiments of the present invention is QELEKQLNRATTNNSVLQKQQLELMDTVHNLV [SEQ ID NO: 13] which corresponds to amino acid residues 231-262 of angiopoietin 1 protein sequence (GenBank Accession number: gi|20532340) or a derivative thereof.

In another embodiment, a homolog of a CGEN-A8 peptide according to at least some embodiments of the present invention is NSVLQKQQLELMDTVHNLVNLCTKEGVLLKG [SEQ ID NO: 14] which corresponds to amino acid residues 244-274 of angiopoietin 1 protein sequence (GenBank Accession number: gi|20532340) or a derivative thereof.

In another embodiment, a homolog of a CGEN-H7 peptide according to at least some embodiments of the present invention is KLEKQLLQQTNEILKIHEKNSLLEHKILEMEGKHKEELDTLKEEK [SEQ ID NO: 15] which corresponds to amino acid residues 172-216 of angiopoietin 1 protein sequence (GenBank Accession number: gi|20532340) or a derivative thereof.

In another embodiment, a homolog of a CGEN-G4 peptide according to at least some embodiments of the present invention is QLQSIKEEKDQLQVLVSKQNSIIEELEKKIVTATVN [SEQ ID NO: 16] which corresponds to amino acid residues 205-240 of angiopoietin 2 protein sequence (GenBank Accession number: gi|4557315) or a derivative thereof.

In another embodiment, a homolog of a CGEN-G6 peptide according to at least some embodiments of the present invention is NNSVLQKQQHDLMETVNNLLTMMSTSN-SAKDPTVAKEEQIS [SEQ ID NO: 17] which corresponds to amino acid residues 240-280 of angiopoietin 2 protein sequence (GenBank Accession number: gi|4557315) or a derivative thereof.

In another embodiment, a homolog of a CGEN-F9 peptide according to at least some embodiments of the present invention is KRLQALETKQQEELASILSKKAK-LLNTLSRQSAALTNIERGLRGVRHNSSLLQDQ Q [SEQ ID NO: 18] which corresponds to amino acid residues 200-255 of angiopoietin 4 protein sequence (GenBank Accession number: gi|7705276) or a derivative thereof.

In another embodiment, a homolog of a CGEN-F12 peptide according to at least some embodiments of the present invention is RHNSSLLQDQQHSLRQLLVLL-RHLVQERANASAPAFIMAGEQV [SEQ ID NO: 19] which corresponds to amino acid residues 245-287 of angiopoietin 4 protein sequence (GenBank Accession number: gi|7705276) or a derivative thereof.

In another embodiment, a homolog of a CGEN-C6 peptide according to at least some embodiments of the present invention is NQTTAQIRKLTDMEAQLLNQTSRMDAQM-PETFLSTNKL [SEQ ID NO: 20] which corresponds to amino acid residues 140-177 of angiopoietin 4 protein sequence (GenBank Accession number: gi|7705276) or a derivative thereof.

In another embodiment, a homolog of a CGEN-A11 peptide according to at least some embodiments of the present invention is QTSRMDAQMPETFLSTNKLEN-QLLLQRQKLQQ [SEQ ID NO: 21] which corresponds to amino acid residues 159-170 of angiopoietin 4 protein sequence (GenBank Accession number: gi|7705276) or a derivative thereof.

In another embodiment, a homolog of a CGEN-G2 peptide according to at least some embodiments of the present invention is ANPLHLGKLPTQQVKQLEQALQNNTQWLKK-LERAIKTILRSKLEQVQQQ [SEQ ID NO: 22] which corresponds to amino acid residues 74-122 of angiopoietin 4 protein sequence (GenBank Accession number: gi|7705276) or a derivative thereof.

The term "homolog" relating to a peptide according to at least some embodiments of the present invention as used herein should also be understood to encompass an ortholog. The term "ortholog" should be understood to encompass a peptide derived from a non-human origin which has substantially the same amino acid sequence and substantially the same biological activity as CGEN-H2, CGEN-H3, CGEN-A8, CGEN-H7, CGEN-G4, CGEN-G6, CGEN-F9, CGEN-F12, CGEN-C6, CGEN-A11 or CGEN-G2, respectively.

In at least some embodiments, the subject invention thus provides an isolated peptide being an ortholog of CGEN-H2 [SEQ ID NO: 1], consisting essentially of an amino acid sequence as depicted in any one of SEQ ID NOs: 165-172, or a derivative thereof.

In at least some embodiments, the subject invention further provides an isolated peptide being an ortholog of CGEN CGEN-H3 [SEQ ID NO: 2], consisting essentially of an amino acid sequence as depicted in any one of SEQ ID NOs: 161-164, or a derivative thereof.

In at least some embodiments, the subject invention further provides an isolated peptide being an ortholog of CGEN-A8 [SEQ ID NO: 3], consisting essentially of an amino acid sequence as depicted in any one of SEQ ID NOs: 137-140, or a derivative thereof.

In at least some embodiments, the subject invention further provides an isolated peptide being an ortholog of CGEN-H7

[SEQ ID NO: 4], consisting essentially of an amino acid sequence as depicted in any one of SEQ ID NOs: 149-154, or a derivative thereof.

In at least some embodiments, the subject invention further provides an isolated peptide being an ortholog of CGEN-G4 [SEQ ID NO: 5], consisting essentially of an amino acid sequence as depicted in any one of SEQ ID NOs: 73-76, or a derivative thereof.

In at least some embodiments, the subject invention further provides an isolated peptide being an ortholog of CGEN-G6 [SEQ ID NO: 6]), consisting essentially of an amino acid sequence as depicted in any one of SEQ ID NOs: 63-72, or a derivative thereof.

In at least some embodiments, the subject invention further provides an isolated peptide being an ortholog of CGEN-F9 [SEQ ID NO: 7], consisting essentially of an amino acid sequence as depicted in any one of SEQ ID NOs: 98-102, or a derivative thereof.

In at least some embodiments, the subject invention further provides an isolated peptide being an ortholog of CGEN-F12 [SEQ ID NO: 8], consisting essentially of an amino acid sequence as depicted in any one of SEQ ID NOs: 106-110, or a derivative thereof.

In at least some embodiments, the subject invention further provides an isolated peptide being an ortholog of CGEN-C6 [SEQ ID NO: 9], consisting essentially of an amino acid sequence as depicted in any one of SEQ ID NOs: 116-118, or a derivative thereof.

In at least some embodiments, the subject invention further provides an isolated peptide being an ortholog of CGEN-A11 [SEQ ID NO: 10], consisting essentially of an amino acid sequence as depicted in any one of SEQ ID NOs: 134-136, or a derivative thereof.

In at least some embodiments, the subject invention further provides an isolated peptide being an ortholog of CGEN-G2 [SEQ ID NO: 11], consisting essentially of an amino acid sequence as depicted in any one of SEQ ID NOs: 124-128, or a derivative thereof.

In at least some embodiments, the subject invention further provides an isolated peptide being an ortholog of the CGEN-H2-related sequence shown in SEQ ID NO: 12, consisting essentially of an amino acid sequence as depicted in any one of SEQ ID NOs: 141-148, or a derivative thereof.

In at least some embodiments, the subject invention further provides an isolated peptide being an ortholog of the CGEN-H3-related sequence shown in SEQ ID NO: 13, consisting essentially of an amino acid sequence as depicted in any one of SEQ ID NOs: 173-179, or a derivative thereof.

In at least some embodiments, the subject invention further provides an isolated peptide being an ortholog of the CGEN-A8-related sequence shown in SEQ ID NO: 14, consisting essentially of an amino acid sequence as depicted in any one of SEQ ID NOs: 155-160, or a derivative thereof.

In at least some embodiments, the subject invention further provides an isolated peptide being an ortholog of the CGEN-H7-related sequence shown in SEQ ID NO: 15, consisting essentially of an amino acid sequence as depicted in any one of SEQ ID NOs: 180-186, or a derivative thereof.

In at least some embodiments, the subject invention further provides an isolated peptide being an ortholog of the CGEN-G4-related sequence shown in SEQ ID NO: 16, consisting essentially of an amino acid sequence as depicted in any one of SEQ ID NOs: 86-92, or a derivative thereof.

In at least some embodiments, the subject invention further provides an isolated peptide being an ortholog of the CGEN-G6-related sequence shown in SEQ ID NO: 17, consisting essentially of an amino acid sequence as depicted in any one of SEQ ID NOs: 77-85, or a derivative thereof.

In at least some embodiments, the subject invention further provides an isolated peptide being an ortholog of the CGEN-F9-related sequence shown in SEQ ID NO: 18, consisting essentially of an amino acid sequence as depicted in any one of SEQ ID NOs: 119-123, or a derivative thereof.

In at least some embodiments, the subject invention further provides an isolated peptide being an ortholog of the CGEN-F12-related sequence shown in SEQ ID NO: 19, consisting essentially of an amino acid sequence as depicted in any one of SEQ ID NOs: 129-133, or a derivative thereof.

In at least some embodiments, the subject invention further provides an isolated peptide being an ortholog of the CGEN-C6-related sequence shown in SEQ ID NO: 20, consisting essentially of an amino acid sequence as depicted in any one of SEQ ID NOs: 93-97, or a derivative thereof.

In at least some embodiments, the subject invention further provides an isolated peptide being an ortholog of the CGEN-A11-related sequence shown in SEQ ID NO: 21, consisting essentially of an amino acid sequence as depicted in any one of SEQ ID NOs:103-105, or a derivative thereof.

In at least some embodiments, the subject invention further provides an isolated peptide being an ortholog of the CGEN-G2-related sequence shown in SEQ ID NO: 22, consisting essentially of an amino acid sequence as depicted in any one of SEQ ID NOs: 111-115, or a derivative thereof.

The term "partner helix (peptide)" as used herein should be understood to encompass a peptide corresponding to an alpha helix within the parent angiopoietin 1, angiopoietin 2 and/or angiopoietin 4 protein (SEQ ID NOs: 45, 46, 47, respectively), which physically interacts with a peptide according to at least some embodiments of the present invention.

In at least some embodiments, the subject invention thus further provides a peptide consisting essentially of an amino acid sequence corresponding to a partner helix of a peptide according to at least some embodiments of the present invention or a homolog or a derivative thereof.

In at least some embodiments, the subject invention provides a peptide consisting essentially of an amino acid sequence corresponding to a partner helix of a peptide having an amino acid sequence as depicted in SEQ ID NO: 1.

In at least some embodiments, the subject invention further provides an isolated peptide consisting essentially of an amino acid sequence ATMLEIGTSLLSQTAEQTRKLTD-VETQVLNQTSRLE (SEQ ID NO:48), corresponding to a partner helix of CGEN-H2 (SEQ ID NO: 1). This peptide SEQ ID NO:48 corresponds to amino acid residues 125-160 of the angiopoietin 1 protein sequence (SEQ ID NO: 45).

In at least some embodiments, the subject invention further provides an isolated peptide consisting essentially of an amino acid sequence LTDVETQVLNQTSRLE (SEQ ID NO:49), corresponding to a partner helix of CGEN-H2 (SEQ ID NO: 1). This peptide SEQ ID NO:49 corresponds to amino acid residues 145-160 of the angiopoietin 1 protein sequence (GenBank Accession number: gi|20532340, SEQ ID NO: 45).

In at least some embodiments, the subject invention provides a peptide consisting essentially of an amino acid sequence corresponding to a partner helix of a peptide having an amino acid sequence as depicted in SEQ ID NO: 2.

In at least some embodiments, the subject invention further provides an isolated peptide consisting essentially of an amino acid sequence ATMLEIGTSLLSQTAEQTRKLTD-VETQVLNQTSRLE (SEQ ID NO:48), corresponding to a partner helix of CGEN-H3 (SEQ ID NO: 2). This peptide SEQ ID NO:48 corresponds to amino acid residues 125-160 of the angiopoietin 1 protein sequence (GenBank Accession number: gi|20532340, SEQ ID NO: 45).

In at least some embodiments, the subject invention further provides an isolated peptide consisting essentially of an amino acid sequence LTDVETQVLNQTSRLE (SEQ ID NO:49), corresponding to a partner helix of CGEN-H3 (SEQ ID NO: 2). This peptide SEQ ID NO:49 corresponds to amino acid residues 145-160 of the angiopoietin 1 protein sequence (GenBank Accession number: gi|20532340, SEQ ID NO: 45).

In at least some embodiments, the subject invention provides a peptide consisting essentially of an amino acid sequence corresponding to a partner helix of a peptide having an amino acid sequence as depicted in SEQ ID NO: 3.

In at least some embodiments, the subject invention further provides an isolated peptide consisting essentially of an amino acid sequence TMLEIGTSLLSQTAEQTRKLTDVETQVLNQTSR (SEQ ID NO:50), corresponding to a partner helix of CGEN-A8 (SEQ ID NO: 3). This peptide SEQ ID NO:50 corresponds to amino acid residues 126-158 of the angiopoietin 1 protein sequence (GenBank Accession number: gi|20532340, SEQ ID NO: 45).

In at least some embodiments, the subject invention further provides an isolated peptide consisting essentially of an amino acid sequence LTDVETQVLNQTSRLE (SEQ ID NO:49), corresponding to a partner helix of CGEN-A8 (SEQ ID NO: 3). This peptide SEQ ID NO:49 corresponds to amino acid residues 145-160 of the angiopoietin 1 protein sequence (GenBank Accession number: gi|20532340, SEQ ID NO: 45).

In at least some embodiments, the subject invention provides a peptide consisting essentially of an amino acid sequence corresponding to a partner helix of a peptide having an amino acid sequence as depicted in SEQ ID NO: 4.

In at least some embodiments, the subject invention further provides an isolated peptide consisting essentially of an amino acid sequence LTDVETQVLNQTSRLEIQLLENSLSTYKLEKQLLQQ (SEQ ID NO:51), corresponding to a partner helix of CGEN-H7 (SEQ ID NO: 4). This peptide SEQ ID NO:51 corresponds to amino acid residues 145-180 of the angiopoietin 1 protein sequence (GenBank Accession number: gi|20532340, SEQ ID NO: 45).

In at least some embodiments, the subject invention provides a peptide consisting essentially of an amino acid sequence corresponding to a partner helix of a peptide having an amino acid sequence as depicted in SEQ ID NO: 5.

In at least some embodiments, the subject invention further provides an isolated peptide consisting essentially of an amino acid sequence QTAVMIEIGTNLLNQTAEQTRKLTDVEAQVLNQTTR (SEQ ID NO:52), corresponding to a partner helix of CGEN-G4 (SEQ ID NO: 5). This peptide SEQ ID NO:52 corresponds to amino acid residues 120-155 of the angiopoietin 2 protein sequence (GenBank Accession number: gi|4557315, SEQ ID NO: 46).

In at least some embodiments, the subject invention further provides an isolated peptide consisting essentially of an amino acid sequence RKLTDVEAQVLNQTTRLELQLLEHSLSTNKLEKQIL (SEQ ID NO:53), corresponding to a partner helix of CGEN-G4 (SEQ ID NO: 5). This peptide SEQ ID NO:53 corresponds to amino acid residues 140-175 of the angiopoietin 2 protein sequence (GenBank Accession number: gi|4557315, SEQ ID NO: 46).

In at least some embodiments, the subject invention further provides an isolated peptide to consisting essentially of an amino acid sequence RKLTDVEAQVLNQTTRLELQL (SEQ ID NO:54), corresponding to a partner helix of CGEN-G4 (SEQ ID NO: 5). This peptide SEQ ID NO:54 corresponds to amino acid residues 140-160 of the angiopoietin 2 protein sequence (GenBank Accession number: gi|4557315, SEQ ID NO: 46).

In at least some embodiments, the subject invention further provides an isolated peptide consisting essentially of an amino acid sequence VEAQVLNQTTRLELQLLEHSLSTNKLEKQILDQTSEINKLQ (SEQ ID NO:55), corresponding to a partner helix of CGEN-G4 (SEQ ID NO: 5). This peptide SEQ ID NO:55 corresponds to amino acid residues 145-185 of the angiopoietin 2 protein sequence (GenBank Accession number: gi|4557315, SEQ ID NO: 46).

In at least some embodiments, the subject invention further provides an isolated peptide consisting essentially of an amino acid sequence TAEQTRKLTDVEAQVLNQTTRLELQL (SEQ ID NO:56), corresponding to a partner helix of CGEN-G4 (SEQ ID NO: 5). This peptide SEQ ID NO:56 corresponds to amino acid residues 135-160 of the angiopoietin 2 protein sequence (GenBank Accession number: gi|4557315, SEQ ID NO: 46).

In at least some embodiments, the subject invention provides a peptide consisting essentially of an amino acid sequence corresponding to a partner helix of a peptide having an amino acid sequence as depicted in SEQ ID NO: 6.

In at least some embodiments, the subject invention further provides an isolated peptide consisting essentially of an amino acid sequence FLEKKVLAMEDKHIIQLQSIKEEKDQLQVLVSKQNSIIEELEKKIVTATVN (SEQ ID NO:57), corresponding to a partner helix of CGEN-G6 (SEQ ID NO: 6). This peptide SEQ ID NO:57 corresponds to amino acid residues 190-240 of the angiopoietin 2 protein sequence (GenBank Accession number: gi|4557315, SEQ ID NO: 46).

In at least some embodiments, the subject invention provides a peptide consisting essentially of an amino acid sequence corresponding to a partner helix of a peptide having an amino acid sequence as depicted in SEQ ID NO: 7.

In at least some embodiments, the subject invention further provides an isolated peptide consisting essentially of an amino acid sequence QLLVLLRHLVQERANASAPAFIMAGEQVFQDCAEIQRSGAS (SEQ ID NO:58), corresponding to a partner helix of CGEN-F9 (SEQ ID NO: 7). This peptide SEQ ID NO:58 corresponds to amino acid residues 260-300 of the angiopoietin 4 protein sequence (GenBank Accession number: gi|7705276, SEQ ID NO: 47).

In at least some embodiments, the subject invention further provides an isolated peptide consisting essentially of an amino acid sequence QLLVLLRHLVQERANA (SEQ ID NO:59), corresponding to a partner helix of CGEN-F9 (SEQ ID NO: 7). This peptide SEQ ID NO:59 corresponds to amino acid residues 260-275 of the angiopoietin 4 protein sequence (GenBank Accession number: gi|7705276, SEQ ID NO: 47).

In at least some embodiments, the subject invention provides a peptide consisting essentially of an amino acid sequence corresponding to a partner helix of a peptide having an amino acid sequence as depicted in SEQ ID NO: 8.

In at least some embodiments, the subject invention further provides an isolated peptide consisting essentially of an amino acid sequence NQTAPMLELGTSLLNQTTAQIRKLTDMEAQLLNQTSRMD (SEQ ID NO:60), corresponding to a partner helix of CGEN-F12 (SEQ ID NO: 8). This peptide SEQ ID NO:60 corresponds to amino acid residues 126-164 of the angiopoietin 4 protein sequence (GenBank Accession number: gi|7705276, SEQ ID NO: 47).

In at least some embodiments, the subject invention provides a peptide consisting essentially of an amino acid sequence corresponding to a partner helix of a peptide having an amino acid sequence as depicted in SEQ ID NO: 9.

In at least some embodiments, the subject invention further provides an isolated peptide consisting essentially of an amino acid sequence QLLVLLRHLVQERANASAPAFIM-AGEQVFQDCAEIQRSGASAS (SEQ ID NO:61), corresponding to a partner helix of CGEN-C6 (SEQ ID NO: 9). This peptide SEQ ID NO:61 corresponds to amino acid residues 260-302 of the angiopoietin 4 protein sequence (GenBank Accession number: gi17705276, SEQ ID NO: 47).

In at least some embodiments, the subject invention further provides an isolated peptide consisting essentially of an amino acid sequence SNTLQRESLAN-PLHLGKLPTQQVKQLEQALQN (SEQ ID NO:62), corresponding to a partner helix of CGEN-C6 (SEQ ID NO: 9). This peptide SEQ ID NO:62 corresponds to amino acid residues 65-96 of the angiopoietin 4 protein sequence (GenBank Accession number: gi17705276, SEQ ID NO: 47).

In at least some embodiments, the subject invention provides a peptide consisting essentially of an amino acid sequence corresponding to a partner helix of a peptide having an amino acid sequence as depicted in SEQ ID NO: 10.

In at least some embodiments, the subject invention further provides an isolated peptide consisting essentially of an amino acid sequence QLLVLLRHLVQERANASAPAFIM-AGEQVFQDCAEIQRSGASAS (SEQ ID NO:61), corresponding to a partner helix of CGEN-A11 (SEQ ID NO: 10). This peptide SEQ ID NO:61 corresponds to amino acid residues 260-302 of the angiopoietin 4 protein sequence (GenBank Accession number: gi17705276, SEQ ID NO: 47).

In at least some embodiments, the subject invention further provides an isolated peptide consisting essentially of an amino acid sequence SNTLQRESLAN-PLHLGKLPTQQVKQLEQALQN (SEQ ID NO:62), corresponding to a partner helix of CGEN-A11 (SEQ ID NO: 10). This peptide SEQ ID NO:62 corresponds to amino acid residues 65-96 of the angiopoietin 4 protein sequence (GenBank Accession number: gi17705276, SEQ ID NO: 47).

In at least some embodiments, the subject invention further provides an antibody that selectively binds to an epitope within a peptide according to at least some embodiments of the present invention. In one embodiment, said epitope is located in a peptide according to at least some embodiments of the present invention as depicted in any one of SEQ ID NOs: 1-11. In another embodiment, said epitope is located in a peptide according to at least some embodiments of the present invention as depicted in any one of SEQ ID NOs: 12-22. In another embodiment, said epitope is located in a peptide according to at least some embodiments of the present invention, as depicted in any one of SEQ ID NOs: 63-186. In yet another embodiment, said epitope is located in a peptide according to at least some embodiments of the present invention as depicted in any one of SEQ ID NOs: 48-62.

In at least some embodiments, the subject invention further provides an antibody that selectively binds to an epitope in a helix-helix structure derived from the interaction of a peptide according to at least some embodiments of the present invention with a corresponding partner helix.

In at least some embodiments, the subject invention further provides a conjugate or fusion protein comprising a peptide according to at least some embodiments of the present invention as set forth in any one of SEQ ID NOs: 1-22, 48-186.

A peptide according to at least some embodiments of the present invention may contain amino acids other than the 20 gene-encoded amino acids. When amino acids are not designated as either D- or L-amino acids, the amino acid is either an L-amino acid or could be either a D- or L-amino acid, unless the context requires a particular isomer.

The notations used herein for the polypeptide amino acid residues are those abbreviations commonly used in the art. The less common abbreviations Abu, Cpa, Nle, Pal, Tle, Dip, 4-Fpa, and Nal stand for 2-amino-butyric acid, p-chlorophenylalanine, norleucine, 3-pyridyl-2-alanine, tert-leucine, 2,2-diphenylalanine, 4-fluoro-phenylalanine, and 3-(2-naphthyl)-alanine or 3-(1-naphthyl)-alanine, respectively.

One example of a non-naturally occurring amino acid is an omega-amino acid, e.g., beta-alanine (beta-Ala), or 3 aminopropionic (3-aP). Other examples are non-naturally occurring amino acids, e.g., sarcosine (Sar), β-alanine (β-Ala), 2,3 diaminopropionic (2,3-diaP) or alpha-aminisobutyric acid (Aib); omega-acid is beta-alanine (beta-Ala), or 3 aminopropionic (3-aP); a hydrophobic non-naturally occurring amino acid, such as t-butylalanine (t BuA), t butylglycine (t BuG), N methylisoleucine (N Mae), norleucine (Nle), methylvaline (Mvl), cyclohexylalanine (Cha), phenylglycine (Phg), NaI, β2-thienylalanine (Thi), 2 naphthylalanine (2 Nal), or 1,2,3,4-tetrahydroisoquinoline-3 carboxylic acid (Tic); a basic amino acid, such as ornithine (Orn) or homoarginine (Har); and a neutral/polar non-naturally occurring amino acid is citrulline (Cit), Acetyl Lys, or methionine sulfoxide (MSO).

Non-natural amino acids are known to those skilled in the art of chemical synthesis and peptide chemistry. Non-limiting examples of non-natural amino acids (each one in L- or D-configuration) are azidoalanine, azidohomoalanine, 2-amino-5-hexynoic acid, norleucine, azidonorleucine, L-a-aminobutyric acid, 3-(1-naphthyl)-alanine, 3-(2-naphthyl)-alanine, p-ethynyl-phenylalanine, m-ethynyl-phenylalanine, p-ethynyl-phenylalanine, p-bromophenylalanine, p-idiophenylalanine, p-azidophenylalanine, 3-(6-chloroindolyl) alanin and those listed in Table 1 below.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methybutyrate | Mgabu | L-N-methylarginine | Nmarg |
| aminocyclopropane-carboxylate | Cpro | L-N-methylasparagine | Nmasn |
| | | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
| | | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |

TABLE 1-continued

| Non-conventional amino acid | Code | Non-conventional amino acid | Code |
|---|---|---|---|
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylserine | Dnmser |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |

TABLE 1-continued

| Non-conventional amino acid | Code | Non-conventional amino acid | Code |
|---|---|---|---|
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine N-(N-(2,2-diphenylethyl) carbamylmethyl-glycine | Mval Nnbhm Nnbhm | L-N-methylhomophenylalanine N-(N-(3,3-diphenylpropyl) carbamylmethyl(1)glycine | Nmhphe Nnbhe |
| 1-carboxy-1-(2,2-diphenyl ethylamino)cyclopropane | Nmbc | | |

Peptides within the invention can be produced using methods known in the art, e.g., by purifying the peptide sequence from a naturally occurring protein or peptide. Purification can be performed along with a cleavage or degradation (either enzymatic or non-enzymatic) to produce the desired peptide using methods known in the art.

Alternatively, peptides can be biochemically synthesized using, e.g., solid phase synthesis, partial solid phase synthesis methods, fragment condensation, classical solution synthesis. These methods are e.g. used when the peptide is relatively short (i.e., 10 kDa) and/or when it cannot be produced by recombinant techniques (i.e., not encoded by a nucleic acid sequence).

Solid phase polypeptide synthesis procedures are well known in the art and further described by John Morrow Stewart and Janis Dillaha Young, *Solid Phase Peptide Syntheses* (2nd Ed, Pierce Chemical Company, 1984).

Synthetic polypeptides can be purified by preparative high performance liquid chromatography [Creighton T. (1983) *Proteins, structures and molecular principles*. WH Freeman and Co. N.Y.] and the composition of which can be confirmed via amino acid sequencing.

Polypeptides or peptides can alternatively be synthesized using recombinant techniques such as those described by Bitter et al., (1987) *Methods in Enzymol.* 153:516-544, Studier et al. (1990) *Methods in Enzymol.* 185:60-89, Brisson et al. (1984) *Nature* 310:511-514, Takamatsu et al. (1987) *EMBO J.* 6:307-311, Coruzzi et al. (1984) *EMBO J.* 3:1671-1680 and Brogli et al., (1984) *Science* 224:838-843, Gurley et al. (1986) *Mol. Cell. Biol.* 6:559-565 and Weissbach & Weissbach, 1988, *Methods for Plant Molecular Biology*, Academic Press, NY, Section VIII, pp 421-463.

Thus, a peptide according to at least some embodiments of the present invention may be prepared synthetically (e.g. on a solid support by solid phase peptide synthesis or in solution) or by recombinant means (in bacteria, yeast, fungi, insect, vertebrate or mammalian cells) by methods well known to those skilled in the art.

In one embodiment, a peptide according to at least some embodiments of the present invention may be synthesized such that one or more of the bonds which link the amino acid residues of the peptide, are non-peptide bonds.

In another embodiment, a peptide according to at least some embodiments of the present invention may be synthesized with additional chemical groups, such that, for example, the stability, bioavailability, and/or inhibitory activity of the peptide is modified. For example, an acetyl group may be placed at the amino termini of a peptide according to at least some embodiments of the present invention. Additionally or alternatively, an amido group may be added to the carboxy termini of a peptide according to at least some embodiments of the present invention.

In yet another embodiment, a peptide according to at least some embodiments of the present invention may be synthesized with an altered steric configuration. For example, the D-isomer of one or more of the amino acid residues of a peptide according to at least some embodiments of the present invention may be used, rather than the usual L-isomer.

In yet a further embodiment, at least one of the amino acid residues of a peptide according to at least some embodiments of the present invention may be substituted by any one of the well known non-naturally occurring amino acid residues, selected from, but not limited to azidoalanine, azidohomoalanine, 2-amino-5-hexynoic acid, norleucine, azidonorleucine, L-a-aminobutyric acid, 3-(1-naphthyl)-alanine, 3-(2-naphthyl)-alanine, p-ethynyl-phenylalanine, m-ethynyl-phenylalanine, p-ethynyl-phenylalanine, p-bromophenylalanine, p-idiophenylalanine, p-azidophenylalanine, 3-(6-chloroindolyl) alanin and those from Table 1 herein.

In another embodiment, a peptide according to at least some embodiments of the present invention may have a non-peptide macromolecular carrier group covalently attached to its amino and/or carboxy terminus. Non-limiting examples of such macromolecular carrier groups are proteins, lipid-fatty acid conjugates, polyethylene glycol, and carbohydrates.

The term "derivative" relating to a peptide according to at least some embodiments of the present invention or a homolog thereof should be understood to encompass a peptide which has substantially the same amino acid sequence and substantially the same biological activity as CGEN-H2, CGEN-H3, CGEN-A8, CGEN-H7, CGEN-G4, CGEN-G6, CGEN-F9, CGEN-F12, CGEN-C6, CGEN-A11, or CGEN-G2. Thus, a derivative may differ from the CGEN-H2, CGEN-H3, CGEN-A8, CGEN-H7, CGEN-G4, CGEN-G6, CGEN-F9, CGEN-F12, CGEN-C6, CGEN-A11, or CGEN-G2 peptide by a modification such as, but not limited to, glycosylation, amidation, acetylation, alkylation, alkenylation, alkynylation, phosphorylation (typically at a serine, threonine, or tyrosine residue), sulphorization, hydroxylation, hydrogenation, cyclization, pegylation, coupling to a biotin moiety, or inclusion of a disulfide bond to another peptide, polypeptide or amino acid. The peptide may be provided in a cyclic form, e.g., as a cyclic peptide or as a lactam. Alternatively, or in addition, the peptide may be provided as a branched peptide.

The peptide may be modified (when linear) at its amino terminus or carboxy terminus. Examples of amino terminal modifications include, e.g., N-glycated, N-alkylated, N-acetylated or N-acylated amino acid. A terminal modification can include a pegylation. An example of a carboxy terminal modification is a c-terminal amidated amino acid. The peptides may be cross-linked or have a cross-linking site (for example, the peptide has a cysteinyl residue and thus forms cross-linked dimers in culture or in vivo. One or more peptidyl bonds may be replaced by a non-peptidyl linkage; the N-terminus or the C-terminus may be replaced, and individual amino acid moieties may be modified through treatment with agents capable of reacting with selected side chains or terminal residues, and so forth. Either the C-terminus or the N-terminus of the sequences, or both, can be linked to a carboxylic acid functional groups or an amine functional group, respectively.

If a peptide according to the present invention is a linear molecule, it is possible to place various functional groups at various points on the linear molecule which are susceptible to or suitable for chemical modification. Functional groups can be added to the termini of linear forms of a peptide. In some embodiments, the functional groups improve the activity of a peptide with regard to one or more characteristics, including but not limited to, improvement in stability, penetration (through cellular membranes and/or tissue barriers), tissue localization, efficacy, decreased clearance, decreased toxicity, improved selectivity, improved resistance to expulsion by cellular pumps, and the like.

Non-limiting examples of suitable functional groups are described in Green and Wuts, "*Protecting Groups in Organic Synthesis*", John Wiley and Sons, Chapters 5 and 7, 1991, the teachings of which are incorporated herein by reference. Preferred protecting groups are those that facilitate transport of a peptide (i.e. the active ingredient) attached thereto into a cell, for example, by reducing the hydrophilicity and increasing the lipophilicity of the active ingredient, these being an example for "a moiety for transport across cellular membranes".

These moieties can optionally and preferably be cleaved in vivo, either by hydrolysis or enzymatically, inside the cell. (Ditter et al., *J. Pharm. Sci.* 57:783 (1968); Ditter et al., *J. Pharm. Sci.* 57:828 (1968); Ditter et al., *J. Pharm. Sci.* 58:557 (1969); King et al., *Biochemistry* 26:2294 (1987); Lindberg et al., *Drug Metabolism and Disposition* 17:311 (1989); and Tunek et al., *Biochem. Pharm.* 37:3867 (1988), Anderson et al., *Arch. Biochem. Biophys.* 239:538 (1985) and Singhal et al., *FASEB J.* 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester, more preferably as a benzyl ester.

Non-limiting, illustrative examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include but are not limited to acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—, Adamantan, naphtalen, myristoleyl, toluen, biphenyl, cinnamoyl, nitrobenzoy, toluoyl, furoyl, benzoyl, cyclohexane, norbornane, or Z-caproic. In order to facilitate the N-acylation, one to four glycine residues can be present at the N-terminus of the molecule.

The carboxyl group at the C-terminus of a peptide can be protected, for example, by a group including but not limited to an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are optionally independently an aliphatic, substituted aliphatic, benzyl, substituted benzyl, aryl or a substituted aryl group. In addition, taken together with the nitrogen atom, R$_2$ and R$_3$ can optionally form a C4 to C8 heterocyclic ring with from about 0-2 additional heteroatoms such as nitrogen, oxygen or sulfur. Non-limiting suitable examples of suitable heterocyclic rings include piperidinyl, pyrrolidinyl, morpholino, thiomorpholino or piperazinyl. Examples of C-terminal protecting groups include but are not limited to —NH$_2$, —NHCH$_3$, —N(CH$_3$)$_2$, —NH(ethyl), —N(ethyl)$_2$, —N(methyl) (ethyl), —NH(benzyl), —N(C1-C4 alkyl)(benzyl), —NH(phenyl), —N(C1-C4 alkyl) (phenyl), —OCH$_3$, —O-(ethyl), —O-(n-propyl), —O-(n-butyl), —O-(iso-propyl), —O-(sec-butyl), —O-(t-butyl), —O-benzyl and —O-phenyl.

A "peptidomimetic organic moiety" can optionally be substituted for amino acid residues in a peptide of this invention both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally and preferably have steric, electronic or configurational properties similar to the replaced amino acid and such peptidomimetics are used to replace amino acids in the essential positions, and are considered conservative substitutions.

Such modifications can be, for example, for the purpose of enhanced potency, selectivity, and/or proteolytic stability, or the like. Those skilled in the art are aware of techniques for designing peptide derivatives with such enhanced properties, such as alanine scanning, rational design based on alignment mediated mutagenesis using known peptide sequences and/or molecular modeling.

Peptidomimetics may optionally be used to inhibit degradation of the peptides by enzymatic or other degradative processes. The peptidomimetics can optionally and preferably be produced by organic synthetic techniques. Non-limiting examples of suitable peptidomimetics include D amino acids of the corresponding L amino acids, tetrazol (Zabrocki et al., *J. Am. Chem. Soc.* 110:5875-5880 (1988)); isosteres of amide bonds (Jones et al., *Tetrahedron Lett.* 29: 3853-3856 (1988)); LL-3-amino-2-propenidone-6-carboxylic acid (LL-Acp) (Kemp et al., *J. Org. Chem.* 50:5834-5838 (1985)). Similar derivatives are shown in Kemp et al., *Tetrahedron Lett.* 29:5081-5082 (1988) as well as Kemp et al., *Tetrahedron Lett.* 29:5057-5060 (1988), Kemp et al., *Tetrahedron Lett.* 29:4935-4938 (1988) and Kemp et al., *J. Org. Chem.* 54:109-115 (1987). Other suitable but exemplary peptidomimetics are shown in Nagai and Sato, *Tetrahedron Lett.* 26:647-650 (1985); Di Maio et al., *J. Chem. Soc. Perkin Trans.,* 1687 (1985); Kahn et al., *Tetrahedron Lett.* 30:2317

(1989); Olson et al., *J. Am. Chem. Soc.* 112:323-333 (1990); Garvey et al., *J. Org. Chem.* 56:436 (1990). Further suitable exemplary peptidomimetics include hydroxy-1,2,3,4-tetrahydroisoquinoline-3-carboxylate (Miyake et al., *J. Takeda Res. Labs* 43:53-76 (1989)); 1,2,3,4-tetrahydro-isoquinoline-3-carboxylate (Kazmierski et al., *J. Am. Chem. Soc.* 133: 2275-2283 (1991)); histidine isoquinolone carboxylic acid (HIC) (Zechel et al., *Int. J. Pep. Protein Res.* 43 (1991)); (2S, 3S)-methyl-phenylalanine, (2S, 3R)-methyl-phenylalanine, (2R, 3S)-methyl-phenylalanine and (2R, 3R)-methyl-phenylalanine (Kazmierski and Hruby, *Tetrahedron Lett.* (1991)).

Exemplary, illustrative but non-limiting non-natural amino acids include beta-amino acids (beta3 and beta2), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA) for example.

In the present invention any part of a peptide may optionally be chemically modified, i.e. changed by addition of functional groups. For example the side amino acid residues appearing in the native sequence may optionally be modified, although as described below alternatively other part(s) of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Gang and Jeanloz, *Advances in Carbohydrate Chemistry and Biochemistry, Vol.* 43, Academic Press (1985); Kunz, *Ang. Chem. Int. Ed. English* 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., *Peptides: Chemistry, Structure and Biology*, Rivier and Marshal, eds., *ESCOM Publ.*, Leiden, 1078-1079 (1990)).

As used herein the term "chemical modification", when referring to a peptide according to the present invention, refers to a peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Other types of modifications optionally include the addition of a cycloalkane moiety to a biological molecule, such as a protein, as described in PCT Application No. WO 2006/050262, hereby incorporated by reference as if fully set forth herein. These moieties are designed for use with biomolecules and may optionally be used to impart various properties to proteins.

Furthermore, optionally any point on a protein may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

Covalent modifications of the peptides of the present invention are included within the scope of this invention. Other types of covalent modifications of the peptides are introduced into the molecule by reacting targeted amino acid residues with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125 I or 131 I to prepare labeled peptides for use in radioimmunoassay.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl)carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking to a water-insoluble support matrix or surface for use in the method for purifying anti-CHF antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco, pp. 79-86 [1983]), acetylation of the N-terminal amine, and amidation of any C-terminal carboxyl group.

Peptides according to at least some embodiments of the present invention may be modified to have an altered glycosylation pattern (i.e., altered from the original or native glycosylation pattern). As used herein, "altered" means having one or more carbohydrate moieties deleted, and/or having at least one glycosylation site added to the original protein.

Glycosylation of proteins is typically either N-linked or O-linked. N-linked glycosylation refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to a peptide according to at least some embodiments of the present invention is conveniently accomplished by altering the amino acid sequence of the peptide such that it contains one or more of the above-described tripeptide sequences (for N-linked glycosylation sites). The alteration may also be made by the addition of, or substitution by, one or more serine or threonine residues in the sequence of the original protein (for O-linked glycosylation sites). The amino acid sequence of the petide may also be altered by introducing changes at the DNA level.

Another means of increasing the number of carbohydrate moieties on proteins is by chemical or enzymatic coupling of glycosides to the amino acid residues of the protein. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, *CRC Grit. Rev. Biochem.*, 22: 259-306 (1981).

Removal of any carbohydrate moieties present on a peptide according to at least some embodiments of the present invention may be accomplished chemically or enzymatically. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Chemical deglycosylation is described by Hakimuddin et al., *Arch. Biochem. Biophys.*, 259: 52 (1987); and Edge et al., *Anal. Biochem.*, 118: 131 (1981). Enzymatic cleavage of carbohydrate moieties on proteins can be achieved by the use of a variety of endo- and exo-glycosidases as described by Thotakura et al., *Meth. Enzymol.*, 138: 350 (1987).

Peptide portions can also be chemically derivatized at one or more amino acid residues. Peptides that contain derivatized amino acid residues can be synthesized by known organic chemistry techniques. "Chemical derivative" or "chemically derivatized" in the context of a peptide refers to a subject peptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivative of the twenty canonical amino acids, whether in L- or D-form. For example, 4-hydroxyproline may be substituted for proline; 5-hydroxylysine maybe substituted for lysine; 3-methylhistidine may be substituted for histidine; homoserine may be substituted for serine; and ornithine may be substituted for lysine.

Useful derivatizations include, in some embodiments, those in which the amino terminal of the peptide is chemically blocked so that conjugation with a vehicle will be prevented from taking place at an N-terminal free amino group. There may also be other beneficial effects of such a modification, for example a reduction in the peptide's susceptibility to enzymatic proteolysis. The N-terminus of the peptide can be acylated or modified to a substituted amine, or derivatized with another functional group, such as an aromatic or aryl moiety (e.g., an indole acid, benzyl (BzI or Bn), dibenzyl (DiBzI or Bn), benzoyl, or benzyloxycarbonyl (Cbz or Z)), /-dimethylglycine or creatine. For example, an acyl moiety, such as, but not limited to, a formyl, 5 acetyl (Ac), propanoyl, butanyl, heptanyl, hexanoyl, octanoyl, or nonanoyl, can be covalently linked to the N-terminal end of a peptide, which can prevent undesired side reactions during conjugation of a vehicle to a peptide. Alternatively, a fatty acid (e.g. butyric, caproic, caprylic, capric, lauric, myristic, palmitic, stearic or the like) or polyethylene glycol moiety can be covalently linked to the N-terminal end of a peptide, e.g., the 0SK1 peptide O analog. Other exemplary N-terminal derivative groups include —NRR 1 (other than —NH2), —NRC(O)R1, —NRC(O)OR 1, —NRS(O) 2R1, —NHC(O)NHR 1, succinimide, or benzyloxycarbonyl-NH— (Cbz-NH—), wherein R and R1 are each independently hydrogen or lower alkyl and wherein the phenyl ring may be substituted with 1 to 3 substituents selected from C1-C4 alkyl, C1-C4 alkoxy, chloro, and bromo.

In another example, basic residues (e.g., lysine) of a peptide of interest can be replaced with other residues (nonfunctional residues preferred). Such molecules will be less basic than the molecules from which they are derived and otherwise retain the activity of the molecules from which they are derived, which can result in advantages in stability and immunogenicity.

Thus, a derivative of a peptide according to at least some embodiments of the present invention may differ from the CGEN-H2, CGEN-H3, CGEN-A8, CGEN-H7, CGEN-G4, CGEN-G6, CGEN-F9, CGEN-F12, CGEN-C6, CGEN-A11, or CGEN-G2 peptide by any modification as described above, on one or more amino acid residues, provided that the resulting peptide retains the biological activity of CGEN-H2, CGEN-H3, CGEN-A8, CGEN-H7, CGEN-G4, CGEN-G6, CGEN-F9, CGEN-F12, CGEN-C6, CGEN-A11, or CGEN-G2, respectively. Persons skilled in the art can readily determine which amino acid residues may be modified using established well known procedures. In one embodiment, a peptide according to at least some embodiments of the present invention is amidated at its C-terminus and acetylated at its N-terminus.

"A peptide with substantially the same amino acid sequence CGEN-H2" as used herein should be understood to encompass a synthetic peptide which has at least 5, preferably at least 8, further preferably at least 30, and at most 50 amino acids, which correspond to a sequential fragment of amino acids 212-241 of the angiopoietin 1 protein sequence (SEQ ID NO: 45)).

"A peptide with substantially the same amino acid sequence as CGEN-H3" as used herein should be understood to encompass a synthetic peptide which has at least 5, preferably at least 8, further preferably at least 11, and at most 32 amino acids, which correspond to a sequential fragment of amino acids 242-252 of the angiopoietin 1 protein sequence (SEQ ID NO: 45).

"A peptide with substantially the same amino acid sequence as CGEN-A8" as used herein should be understood to encompass a synthetic peptide which has at least 5, preferably at least 8, preferably 11, and at most 31 amino acids, which correspond to a sequential fragment of amino acids 254-264 of the angiopoietin 1 protein sequence (SEQ ID NO: 45).

"A peptide with substantially the same amino acid sequence as CGEN-H7" as used herein should be understood to encompass a synthetic peptide which has at least 5, preferably at least 8, preferably 25, and at most 45 amino acids, which correspond to a sequential fragment of amino acids 182-206 of the angiopoietin 1 protein sequence (SEQ ID NO: 45).

"A peptide with substantially the same amino acid sequence as CGEN-G4" as used herein should be understood to encompass a synthetic peptide which has at least 5, preferably at least 8, preferably 16, and at most 36 amino acids, which correspond to a sequential fragment of amino acids 215-230 of the angiopoietin 2 protein sequence (SEQ ID NO: 46).

"A peptide with substantially the same amino acid sequence as CGEN-G6" as used herein should be understood to encompass a synthetic peptide which has at least 5, preferably at least 8, preferably 21, and at most 41 amino acids, which correspond to a sequential fragment of amino acids 250-270 of the angiopoietin 2 protein sequence (SEQ ID NO: 46).

"A peptide with substantially the same amino acid sequence as CGEN-F9" as used herein should be understood to encompass a synthetic peptide which has at least 5, preferably at least 8, preferably 36, and at most 56 amino acids, which correspond to a sequential fragment of amino acids 210-245 of the angiopoietin 4 protein sequence (SEQ ID NO: 47).

"A peptide with substantially the same amino acid sequence as CGEN-F12" as used herein should be understood to encompass a synthetic peptide which has at least 5, preferably at least 8, preferably 23, and at most 43 amino acids, which correspond to a sequential fragment of amino acids 255-277 of the angiopoietin 4 protein sequence (SEQ ID NO: 47).

"A peptide with substantially the same amino acid sequence as CGEN-C6" as used herein should be understood to encompass a synthetic peptide which has at least 5, preferably at least 8, preferably 18, and at most 38 amino acids, which correspond to a sequential fragment of amino acids 150-167 of the angiopoietin 4 protein sequence (SEQ ID NO: 47).

"A peptide with substantially the same amino acid sequence as CGEN-A11" as used herein should be understood to encompass a synthetic peptide which has at least 5, preferably at least 8, preferably 12, and at most 32 amino acids, which correspond to a sequential fragment of amino acids 169-180 of the angiopoietin 4 protein sequence (SEQ ID NO: 47).

"A peptide with substantially the same amino acid sequence as CGEN-G2" as used herein should be understood to encompass a synthetic peptide which has at least 5, preferably at least 8, preferably 29, and at most 49 amino acids, which correspond to a sequential fragment of amino acids 84-112 of the angiopoietin 4 protein sequence (SEQ ID NO: 47).

"A peptide with substantially the same biological activity as CGEN-H2, CGEN-H3, CGEN-A8, CGEN-H7, CGEN-G4, CGEN-G6, CGEN-F9, CGEN-F12, CGEN-C6, CGEN-A11, or CGEN-G2" as used herein should be understood to encompass a peptide which has at least 80% of the biological activity of CGEN-H2, CGEN-H3, CGEN-A8, CGEN-H7, CGEN-G4, CGEN-G6, CGEN-F9, CGEN-F12, CGEN-C6, CGEN-A11, or CGEN-G2, respectively Compositions, Uses and Methods of Treatment According to at least some embodiments of the present invention, there is provided pharmaceutical compositions and formulations, as well as uses and methods of treatment, by using one or more of the peptides or a homolog or a derivative thereof, antibodies and/or fusion proteins as described herein, alone or in combination, optionally and preferably in combination with a pharmaceutically acceptable carrier. Some non-limiting, illustrative examples of such compositions, uses and methods of treatment are described below. Any one or more of the peptides or a homolog or a derivative thereof, antibodies and/or fusion proteins as described herein, alone or in combination, may optionally be described as a "therapeutic agent".

In at least some embodiments, the subject invention further provides a pharmaceutical composition comprising a peptide according to at least some embodiments of the present invention or a homolog or a derivative thereof and a pharmaceutically acceptable carrier. In at least some embodiments, the subject invention also provides a pharmaceutical composition comprising an antibody according to at least some embodiments of the present invention and a pharmaceutically acceptable carrier. In at least some embodiments, the subject invention additionally provides a pharmaceutical composition comprising a fusion protein according to at least some embodiments of the present invention and a pharmaceutically acceptable carrier.

Suitable routes of administration of a peptide or pharmaceutical composition of the subject invention are intravascular delivery (e.g. injection or infusion), oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intra-cerebral, and convection enhanced diffusion), CNS delivery (e.g. intrathecal, perispinal, and intra-spinal) or parenteral (including subcutaneous, intramuscular, intravenous and intradermal), transmucosal (e.g., sublingual administration), administration or administration via an implant, or other delivery routes and/or forms of administration known in the art. In a specific embodiment, a peptide or a pharmaceutical composition according to at least some embodiments of the present invention can be administered intravenously.

The exact dose and regimen of administration of a peptide or pharmaceutical composition comprising a peptide according to at least some embodiments of the present invention will necessarily be dependent upon the therapeutic effect to be achieved (e.g. treatment of cancer) and may vary with the particular compound, the route of administration, and the age and condition of the individual subject to whom the medicament is to be administered.

A dosage for humans is likely to contain 0.01-50 mg per kg body weight per day. The desired dose may be presented as one dose or as multiple sub-doses administered at appropriate intervals.

The present invention thus also relates to a pharmaceutical composition comprising a peptide of the subject invention or a homolog or derivative thereof (or comprising an antibody thereto or comprising a fusion protein comprising a peptide according to at least some embodiments of the present invention) in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for intravascular delivery route such as by injection or infusion, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intra-cerebral, and convection enhanced diffusion), CNS delivery (e.g. intrathecal, perispinal, and intra-spinal) or parenteral (including subcutaneous, intramuscular, intravenous and intradermal), transmucosal (e.g., sublingual administration), administration or administration via an implant. The compositions may be prepared by any method well known in the art of pharmacy.

Such methods include the step of bringing in association a peptide according to at least some embodiments of the present invention with any auxiliary agent. The auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, troches, lozenges, dragées or hard or soft capsules, or as a dispersible powder or granules, or as a solution or suspension for example, as aqueous or oily suspensions, emulsions, syrups, elixirs or enteral formulas. The active ingredient may also be presented as a bolus or paste. The compositions can further be processed into a suppository or enema for rectal administration.

According to at least some embodiments there is further provided a pharmaceutical composition, as hereinbefore described, in combination with packaging material, including instructions for the use of the composition for a use as hereinbefore described.

According to at least some embodiments there is further provided a kit comprising (i) a pharmaceutical composition, as hereinbefore described, in combination with (ii) packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The peptides according to at least some embodiments of the present invention are typically provided in a pharmaceutically acceptable carrier suitable for administering the pharmaceutical composition to a human patient. As would be appreciated by one of skill in this art, the carriers may be chosen based on the route of administration as described above, the location of the target issue, the drug being delivered, the time course of delivery of the drug, etc.

The term "pharmaceutically acceptable carrier" should be understood to encompass a non-toxic, inert solid, semi-solid or liquid filler, diluent, encapsulating material or formulation auxiliary of any type. One exemplary pharmaceutically acceptable carrier is physiological saline. Other physiologically acceptable carriers and their formulations are known to one skilled in the art and described, for example, in Remington's Pharmaceutical Sciences, ($18^{th}$ edition). A. Gennaro, 1990, Mack Publishing Company, Easton, Pa. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN™ 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition.

A variety of conventional thickeners are useful in creams, ointments, suppository and gel configurations of a pharmaceutical composition, such as, but not limited to, alginate, xanthan gum, or petrolatum, may also be employed in such configurations of a pharmaceutical composition of the present invention. A permeation or penetration enhancer, such as polyethylene glycol monolaurate, dimethyl sulfoxide, N-vinyl-2-pyrrolidone, N-(2-hydroxyethyl)-pyrrolidone, or 3-hydroxy-N-methyl-2-pyrrolidone can also be employed. Useful techniques for producing hydrogel matrices are known. (E.g., Feijen, Biodegradable hydrogel matrices for the controlled release of pharmacologically active agents, U.S. Pat. No. 4,925,677; Shah et al., Biodegradable pH/thermosensitive hydrogels for sustained delivery of biologically active agents, WO 00/38651 A1). Such biodegradable gel matrices can be formed, for example, by crosslinking a proteinaceous component and a polysaccharide or mucopolysaccharide component, then loading with a peptide according to at least some embodiments of the present invention to be delivered.

Liquid pharmaceutical compositions of the present invention that are sterile solutions or suspensions can be administered to a patient by injection, for example, intramuscularly, intrathecal, epidurally, intravascularly (e.g., intravenously or intraarterially), intraperitoneally or subcutaneously. (See, e.g., Goldenberg et al., Suspensions for the sustained release of proteins, U.S. Pat. No. 6,245,740 and WO 00/38652 A1). Sterile solutions can also be administered by intravenous infusion. The composition can be included in a sterile solid pharmaceutical composition, such as a lyophilized powder, which can be dissolved or suspended at a convenient time before administration to a patient using sterile water, saline, buffered saline or other appropriate sterile injectable medium.

Implantable sustained release formulations are also useful embodiments according to at least some embodiments of the present invention. For example, a pharmaceutically acceptable carrier, being a biodegradable matrix implanted within the body or under the skin of a human or non-human vertebrate, can be a hydrogel similar to those described above. Alternatively, it may be formed from a poly-alpha-amino acid component. (Sidman, Biodegradable, implantable drug delivery device, and process for preparing and using same, U.S. Pat. No. 4,351,337). Other techniques for making implants for delivery of drugs are also known and useful in accordance with the present invention.

"Pharmaceutically acceptable salt" should be understood to encompass non-toxic acid addition salts or metal complexes which are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like.

An antifrictional agent can be included in the formulation of the therapeutic to prevent sticking during the formulation process. Lubricants can be used as a layer between the therapeutic and the die wall, and these can include but are not limited to; stearic acid including its magnesium and calcium salts, polytetrafluoroethylene (PTFE)1 liquid paraffin, vegetable oils and waxes.

Soluble lubricants can also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants can include starch, talc, pyrogenic silica and hydrated silicoaluminate.

To aid dissolution of the compound of this invention into the aqueous environment a surfactant might be added as a wetting agent. Surfactants can include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of a peptide or derivative either alone or as a mixture in different ratios.

The pharmaceutical compositions can be administered to a patient by any means known in the art including oral and parenteral routes. The term "patient", as used herein, refers to humans as well as non-humans, including, for example, mammals, birds, reptiles, amphibians and fish. Preferably, the non-humans are mammals (e.g., a rodent (including a mouse or rat), a rabbit, a monkey, a dog, a cat, sheep, cow, pig, horse). The non-human animal could alternatively be a bird, e.g., a chicken or turkey.

In certain embodiments parenteral routes are preferred since they avoid contact with the digestive enzymes that are found in the alimentary canal. According to such embodiments, a peptide or composition according to at least some embodiments of the present invention may be administered by one or more of injection (e.g., intravenous, subcutaneous or intramuscular, intraperitoneal injection), rectally, vaginally, topically (as by powders, creams, ointments, or drops), or by inhalation (as by sprays), intranasal, pulmonary, or intrabuccal.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In a particularly preferred embodiment, a therapeutic agent is suspended in a carrier fluid comprising 1% (w/v) sodium carboxymethyl cellulose and 0.1% (v/v) TWEEN80™. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the therapeutic agent with suitable non-irritating excipients or carriers such as cocoa butter, polyethylene glycol, or a suppository wax which are solid at ambient temperature but liquid at body temperature and therefore melt in the rectum or vaginal cavity and release the therapeutic agent.

Dosage forms for topical or transdermal administration of a pharmaceutical composition include ointments, pastes, creams, lotions, gels, powders, solutions, sprays, inhalants, or patches. A peptide (i.e. the therapeutic agent) is admixed under sterile conditions with a pharmaceutically acceptable carrier and any needed preservatives or buffers as may be required. Ophthalmic formulations, ear drops and eye drops are also contemplated as being within the scope of this invention. The ointments, pastes, creams and gels may contain, in addition to the therapeutic agent, excipients such as animal and vegetable fats, oils, waxes, paraffins, starch, tragacanth, cellulose derivatives, polyethylene glycols, silicones, bentonites, silicic acid, talc and zinc oxide, or mixtures thereof. Transdermal patches have the added advantage of providing controlled delivery of to the body. Such dosage forms can be made by dissolving or dispensing the therapeutic agents in a proper medium. Absorption enhancers can also be used to increase the flux of the compound across the skin. The rate can be controlled by either providing a rate controlling membrane or by dispersing the therapeutic agents in a polymer matrix or gel.

Powders and sprays can also contain excipients such as lactose, talc, silicic acid, aluminum hydroxide, calcium silicates and polyamide powder, or mixtures of these drugs. Sprays can additionally contain customary propellants such as chlorofluorohydrocarbons.

Pulmonary delivery is also optionally useful. The peptide (or derivative) is delivered to the lungs of a mammal while inhaling and traverses across the lung epithelial lining to the blood stream. (Adjei et al., *Pharma. Res.* (1990) 7: 565-9; Adjei et al. (1990), *Internatl. J. Pharmaceutics* 63: 135-44 (leuprolide acetate);).

Useful in the practice of this invention are a wide range of mechanical devices designed for pulmonary delivery of therapeutic products, including but not limited to nebulizers, metered dose inhalers, and powder inhalers, all of which are familiar to those skilled in the art. Typically, each formulation is specific to the type of device employed and can involve the use of an appropriate propellant material, in addition to diluents, adjuvants and/or carriers useful in therapy.

The therapeutic agent should most advantageously be prepared in particulate form with an average particle size of less than 10 μm (or microns), most preferably 0.5 to 5 μm, for most effective delivery to the distal lung.

Pharmaceutically acceptable carriers include carbohydrates such as trehalose, mannitol, xylitol, sucrose, lactose, and sorbitol. Other ingredients for use in formulations can include DPPC, DOPE, DSPC and DOPC. Natural or synthetic surfactants can be used. PEG can be used (even apart from its use in derivatizing the protein or homolog). Dextrans, such as cyclodextran, can be used. Bile salts and other related enhancers can be used. Cellulose and cellulose derivatives can be used. Amino acids can be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the therapeutic agent dissolved in water at a concentration of about 0.1 to 25 mg of biologically active agent per mL of solution. The formulation can also include a buffer and a simple sugar (e.g., for protein stabilization and regulation of osmotic pressure). The nebulizer formulation can also contain a surfactant, to reduce or prevent surface induced aggregation of the agent caused by atomization of the solution in forming the aerosol.

Formulations for use with a metered-dose inhaler device will generally comprise a finely divided powder containing the therapeutic agent suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid can also be useful as a surfactant. (See, e.g., Backstr et al., Aerosol drug formulations containing hydrofluoroalkanes and alkyl saccharides, U.S. Pat. No. 6,932,962).

Formulations for dispensing from a powder inhaler device will comprise a finely divided dry powder containing a composition according to at least some embodiments of the present invention and can also include a bulking agent, such as lactose, sorbitol, sucrose, mannitol, trehalose, or xylitol in amounts which facilitate dispersal of the powder from the device, e.g., 50 to 90% by weight of the formulation.

According to at least some embodiments, intranasal delivery of the peptides and/or pharmaceutical compositions is also useful, which allows passage thereof to the blood stream directly after administration to the inside of the nose, without the necessity for deposition of the product in the lung. Formulations suitable for intransal administration include those with dextran or cyclodextran, and intranasal delivery devices are known.

In some embodiments, the composition is configured as a part of a pharmaceutically acceptable transdermal or transmucosal patch or a troche. Transdermal patch drug delivery systems, for example, matrix type transdermal patches, are known and useful for practicing some embodiments of the present pharmaceutical compositions. (E.g., Chien et al., Transdermal estrogen/progestin dosage unit, system and process, U.S. Pat. Nos. 4,906,169 and 5,023,084). A variety of pharmaceutically acceptable systems fort ransmucosal delivery of therapeutic agents are also known in the art and are compatible with the practice of the present invention. (E.g., Heiber et al., Transmucosal delivery of macromolecular drugs, U.S. Pat. Nos. 5,346,701 and 5,516,523; Longenecker et al., Transmembrane formulations for drug administration, U.S. Pat. No. 4,994,439).

Buccal delivery of the compositions is also useful. Buccal delivery formulations are known in the art for use with peptides. For example, known tablet or patch systems configured for drug delivery through the oral mucosa (e.g., sublingual mucosa), include some embodiments that comprise an inner layer containing the drug, a permeation enhancer, such as a bile salt or fusidate, and a hydrophi; c polymer, such as hydroxypropyl cellulose, hydroxypropyl methylcellulose, hydroxyethyl cellulose, dextran, pectin, polyvinyl pyrrolidone, starch, gelatin, or any number of other polymers known to be useful for this purpose. This inner layer can have one surface adapted to contact and adhere to the moist mucosal tissue of the oral cavity and can have an opposing surface adhering to an overlying non-adhesive inert layer. Optionally, such a transmucosal delivery system can be in the form of a bilayer tablet, in which the inner layer also contains additional binding agents, flavoring agents, or fillers. Some useful systems employ a non-ionic detergent along with a permeation enhancer. Transmucosal delivery devices may be in free form, such as a cream, gel, or ointment, or may comprise a determinate form such as a tablet, patch or troche. For example, delivery of a composition can be via a transmucosal delivery system comprising a laminated composite of, for example, an adhesive layer, a backing layer, a permeable membrane defining a reservoir containing a composition, a peel seal disc underlying the membrane, one or more heat seals, and a removable release liner. (E.g., Ebert et al., Transdermal delivery system with adhesive overlay and peel seal disc, U.S. Pat. No. 5,662,925; Chang et al., Device for administering an active agent to the skin or mucosa, U.S. Pat. Nos. 4,849,224 and 4,983,395). These examples are merely illustrative of available transmucosal drug delivery technology and are not limiting of the present invention.

When administered orally, the therapeutic agent is optionally encapsulated. A variety of suitable encapsulation systems are known in the art ("Microcapsules and Nanoparticles in Medicine and Pharmacy," Edited by Doubrow, M., CRC Press, Boca Raton, 1992; Mathiowitz and Langer J. Control. Release 5:13, 1987; Mathiowitz et al., Reactive Polymers 6:275, 1987; Mathiowitz et al., J. Appl. Polymer Sci. 35:755, 1988; Langer Acc. Chem. Res. 33:94, 2000; Langer J. Control. Release 62:7, 1999; Uhrich et al., Chem. Rev. 99:3181, 1999; Zhou et al., J. Control. Release 75:27, 2001; and Hanes et al., Pharm. Biotechnol. 6:389, 1995). For example, the therapeutic agent can be encapsulated within biodegradable polymeric microspheres or liposomes. Examples of natural and synthetic polymers useful in the preparation of biodegradable microspheres include carbohydrates such as alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids, poly(ortho esters) and other biodegradable polyesters. Examples of lipids useful in liposome production include phosphatidyl compounds, such as phosphatidylglycerol, phosphatidylcholine, phosphatidylserine, phosphatidylethanolamine, sphingolipids, cerebrosides and gangliosides.

Pharmaceutical compositions for oral administration can be liquid or solid. Liquid dosage forms suitable for oral administration of compositions include pharmaceutically acceptable emulsions, microemulsions, solutions, suspensions, syrups and elixirs. In addition to an encapsulated or unencapsulated therapeutic agent, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions can also include adjuvants, wetting agents, emulsifying and suspending agents, sweetening, flavoring and perfuming agents. As used herein, the term "adjuvant" refers to any compound which is a nonspecific modulator of the immune response. In certain preferred embodiments, the adjuvant stimulates the immune response. Any adjuvant may be used in accordance with the present invention. A large number of adjuvant compounds are known in the art (Allison, Dev. Biol. Stand. 92:3, 1998; Unkeless et al., Annu. Rev. Immunol. 6:251, 1998; and Phillips et al., Vaccine 10: 151, 1992).

Solid dosage forms for oral administration include capsules, tablets, pills, powders and granules. In such solid dosage forms, the encapsulated or unencapsulated therapeutic agent is mixed with at least one inert, pharmaceutically acceptable excipient or carrier such as sodium citrate or dicalcium phosphate and/or (a) fillers or extenders such as starches, lactose, sucrose, glucose, mannitol and silicic acid, (b) binders such as, for example, carboxymethylcellulose, alginates, gelatin, polyvinylpyrrolidinone, sucrose and acacia, (c) humectants such as glycerol, (d) disintegrating agents such as agar-agar, calcium carbonate, potato or tapioca starch, alginic acid, certain silicates and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay and (i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills and granules can be prepared with coatings and shells such as enteric coatings and other coatings well known in the pharmaceutical formulating art.

The exact dosage of the therapeutic agent is chosen by the individual physician in view of the patient to be treated. In general, dosage and administration are adjusted to provide an effective amount of the therapeutic agent to the patient being treated. As used herein, the "effective amount" of a therapeutic agent refers to the amount necessary to elicit the desired biological response. As will be appreciated by those of ordinary skill in this art, the effective amount of therapeutic agent may vary depending on such factors as the desired biological endpoint, the drug to be delivered, the target tissue, the route of administration, etc. For example, the effective amount of therapeutic agent containing an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy. Long acting pharmaceutical compositions might be administered every 3 to 4 days, every week, or once every two weeks depending on half-life and clearance rate of the particular composition. The therapeutic agents according to at least some embodiments of the present invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compositions of the present invention will be decided by the attending physician within the scope of sound medical judgment. For any therapeutic agent, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of therapeutic agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index and it can be expressed as the ratio, LD50/ED50. Pharmaceutical compositions which exhibit large therapeutic indices are preferred. The data obtained from cell culture assays and animal studies is used in formulating a range of dosage for human use.

If several different therapeutic modalities (e.g., with different therapeutic agents) are to be administered simultaneously then they may optionally be combined into a single pharmaceutical composition. Alternatively, they may optionally be prepared as separate compositions that are then mixed or simply administered one after the other. If several different therapeutic agents (e.g., with different therapeutic agents) are to be administered at different times then they are preferably prepared as separate compositions. If additional drugs are going to be included in a combination therapy they can be added to one or more of these therapeutic agents or prepared as separate compositions.

A peptide could be chemically modified in order to alter its properties such as biodistribution, pharmacokinetics and solubility. Various methods have been used to increase the solubility and stability of drugs, among them the use of organic solvents, their incorporation within emulsions or liposomes, the adjustment of pH, their chemical modifications and their complexation with the cyclodextrins. The cyclodextrins are oligosacharides cyclic family, which include six, seven or eight units of glucopyranose. Due to sterics interactions, the cyclodextrins form a cycle structure in the shape of a cone with an internal cavity. Those are compounds chemically stable that can be modified. The cyclodextrins hosts form complexes with various hydrophobic guests in their cavity. The cyclodextrins are used for the solubilization and encapsulation of drugs.

There are a number of drug delivery systems including but not limited to polymer microcapsules, microparticles, nanoparticles, liposomes and emulsion, prepared from synthetic biodegradable polymers such as polyanhydrides and poly hydroxy acids. In these systems the drugs are incorporated in polymeric microspheres, which release the drug inside the organism in small and controlled daily doses during days, months or years.

Several polymers were already tested in controlled release systems, e.g. poiyuretans for its elasticity, polysiloxans or silicons for being a good one insulation, polymethyl-metacrilate for its physical form; polyvinilalcohol for its hydrophobicity and resistance, and polyethilene for its hardness and impermeability (Gilding, D. K. Biodegradable polymers. Biocompat. Clin. Impl. Mater. 2:209-232, 1981). Biodegradable polymers and biocompatible polymers, have been extensively investigated as vehicles for controlled release systems due to their ability to undergo surface degradation. These kind of polymers can e.g. be chosen from: poly(2-hydroxi-ethyl-metacrilate), polyacrilamide, polymer from lactic acid (PLA), from glicolic acid (PGA), and the respective ones co-polymers, (PLGA) and the poly(anidrides), as described by Tamada and Langer, *J. Biomater. Sci. Polym. Edn,* 3(4): 315-353.

Suitable controlled release vehicles include, but are not limited to, biocompatible polymers, other polymeric matrices, capsules, microcapsules, nanocapsules, microparticles, nanoparticles, bolus preparations, osmotic pumps, diffusion devices, liposomes, lipospheres and transdermal delivery systems, implantable or not.

Liposomes are lipid vesicles that include aqueous internal compartments in which molecules, for example drugs, are encapsulated with the objective of reaching a controlled release of the drug after administration in individuals. Many different techniques have been proposed for the preparation of liposomes [U.S. Pat. No. 4,552,803, Lenk; U.S. Pat. No. 4,310,506, Baldeschwieler; U.S. Pat. No. 4,235,871, Papahadjopoulos; U.S. Pat. No. 4,224,179, Schneider; U.S. Pat. No. 4,078,052, Papahadjopoulos; U.S. Pat. No. 4,394,372, Tailor; U.S. Pat. No. 4,308,166, Marchetti; U.S. Pat. No. 4,485,054, Mezei; and U.S. Pat. No. 4,508,703, Redziniak; Woodle and Papahadjopoulos, *Methods Enzymol.* 171:193-215 (1989]; Unilamellar vesicles display a single membrane [Huang, *Biochemistry* 8:334-352 (1969] while muitilamellar vesicles (MLVs) have numerous concentric membranes [Bangham et al., *J. Mol. Biol.* 13:238-252 (1965]. The procedure of Bangham [*J. Mol. Biol.* 13:238-252 (1965] produces "ordinary MLVs", that present unequal solute distributions among the aqueous compartments and, consequently, differences of osmotic pressure. Lenk et al. (U.S. Pat. Nos. 4,522,803; 5,030,453 and 5,169,637), Fountain et al. (U.S. Pat. No. 4,588,578), Cullis et al. (U.S. Pat. No. 4,975,282) and Gregoriadis et al. (Pat. W.O. 99/65465) introduced methods for the preparation of MLVs that present substantially equal solute distributions among the compartments. Similar solute distributions among the different compartments mean a larger drug encapsulation efficiency as well as smaller differences of osmotic pressure that turns these MLVs more stable than ordinary MLVs. Unilamellar vesicles can be produced by sonication of MLVs or by extrusion through polycarbonate membranes [Cullis et al. (U.S. Pat. No. 5,008,050) and Loughrey et al. (U.S. Pat. No. 5,059,421)].

Suitable lipids include for example, phosphatidylcholine, phosphatidylserine, phosphatidylglycerol, cardiolipin, cholesterol, phosphatidic acid, sphingolipids, glycolipids, fatty acids, sterols, phosphatidylethanolamine, polymerizable lipids in their polymerized or non-polymerized form, mixture of these lipids.

The composition of the liposomes can be manipulated such as to turn them specific for an organ or a cell type. The targeting of liposomes has been classified either on the basis of anatomical factors or on the basis of the mechanism of their interaction with the environment. The anatomical classification is based on their level of selectivity, for example, organ-specific or cell-specific. From the point of view of the mechanisms, the-targeting can be considered as passive or active.

The passive targeting exploits the natural tendency of conventional liposomes to be captured by the cells of the reticuloendothelial system, i.e. mainly the fixed macrophages in the liver, spleen and bone marrow.

Sterically stabilized liposomes (also well-known as "PEG-liposomes") are characterized by a reduced rate of elimination from the blood circulation [Lasic and Martin, *Stealth Liposomes,* CRC Press, Inc., Boca Raton, Fla. (1995)].

PEG-liposomes present a polyethylene glycol polymer conjugated to the head group of some phospholipid that reduces their interaction with plasma proteins, such as opsonins, and reduces the rate of their uptake by cells. The resulting steric barrier allows these liposomes to remain for a longer period of time within the circulation than conventional liposomes [Lasic and Martin, *Stealth Liposomes*, CRC Press, Inc., Boca Raton, Fla. (1995); Woodle et al., *Biochim. Biophys. Acta* 1105:193-200 (1992); Litzinger et al., *Biochim. Biophys. Acta* 1190:99-107 (1994); Bedu Addo, et al., *Pharm. Res.* 13:718-724 (1996]. The drug encapsulation within PEG-liposomes has resulted in the improvement of the effectiveness of many chemotherapeutic agents [Lasic and Martin, *Stealth liposomes*, CRC Press, Inc., Boca Raton, Fla. (1995)] and bioactive peptides [Allen T. M. *In: Liposomes, New Systems, New Trends in their Applications* (F. Puisieux, P. Couvreur, J. Delattre, J.-P. Devissaguet Ed.), Editions de la Sante, France, 1995, pp. 125].

Studies in this area demonstrated that different factors affect the effectiveness of PEG-liposomes. Ideally, the diameter of the vesicles should be below 200 nm, the number of units in PEG of approximately 2.000 and the proportion of Pegylated lipid from 3 to 5 mol % [Lasic and Martin, *Stealth Liposomes,* CRC Press, Inc., Boca Raton, Fla. (1995); Woodle et al., *Biochim. Biophys. Acta* 1105:193-200 (1992); Litzinger et al., *Biochim. Biophys. Acta* 1190:99-107 (1994); Bedu Addo et al., *Pharm. Res.* 13:718-724 (1996)].

The active targeting involves alteration of liposomes through their association with a ligand, such as a monoclonal antibody, a sugar, a glycolipid, protein, a polymer or by changing the lipid composition or the liposome size to target them to organs and cells different from those which accumulate conventional liposomes.

"Mucosal delivery enhancing agents" are defined as chemicals and other excipients that, when added to a formulation comprising water, salts and/or common buffers and peptide within the present invention (the control formulation) produce a formulation that produces a significant increase in transport of peptide across a mucosa as measured by the maximum blood, serum, or cerebral spinal fluid concentration (Cmax) or by the area under the curve, AUC, in a plot of concentration versus time. A mucosa includes the nasal, oral, intestinal, buccal, bronchopulmonary, vaginal, and rectal mucosal surfaces and in fact includes all mucus-secreting membranes lining all body cavities or passages that communicate with the exterior. Mucosal delivery enhancing agents are sometimes called carriers.

The present invention, according to at least some embodiments, provides improved mucosal (e.g., nasal) delivery of a formulation comprising a peptide according to at least some embodiments of the present invention in combination with one or more mucosal delivery-enhancing agents and an optional sustained release-enhancing agent or agents. Mucosal delivery-enhancing agents of the present invention yield an effective increase in delivery, e.g., an increase in the maximal plasma concentration (Cmax) to enhance the therapeutic activity of mucosally-administered peptide. A second factor affecting therapeutic activity of the peptide in the blood plasma and CNS is residence time (RT). Sustained release-enhancing agents, in combination with intranasal delivery-enhancing agents, increase Cmax and increase residence time (RT) of the peptide. Polymeric delivery vehicles and other agents and methods of the present invention that yield sustained release-enhancing formulations, for example, polyethylene glycol (PEG), are disclosed herein. Within the mucosal delivery formulations and methods according to at least some embodiments of the present invention, the peptide is frequently combined or coordinately administered with a suitable carrier or vehicle for mucosal delivery.

As used herein, the term "carrier" means a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories, can be found in the U.S. Pharmacopeia National Formulary, 1857-1859, (1990). As used herein, "mucosal delivery-enhancing agents" include agents which enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery, or at a selected target site of activity such as the bloodstream or central nervous system) of the peptide or other biologically active compound(s). Within certain aspects according to at least some embodiments of the present invention, absorption-promoting agents for coordinate administration or combinatorial formulation with the peptide according to at least some embodiments of the present invention are selected from small hydrophilic molecules, including but not limited to, dimethyl sulfoxide (DMSO), dimethylformamide, ethanol, propylene glycol, and the 2-pyrrolidones. Alternatively, long-chain amphipathic molecules, for example, deacylmethyl sulfoxide, azone, sodium laurylsulfate, oleic acid, and the bile salts, may be employed to enhance mucosal penetration of the peptide. In additional aspects, surfactants (e.g., polysorbates) are employed as adjunct compounds, processing agents, or formulation additives to enhance intranasal delivery of the peptide. Agents such as DMSO, polyethylene glycol, and ethanol can, if present in sufficiently high concentrations in delivery environment (e.g., by pre-administration or incorporation in a therapeutic formulation), enter the aqueous phase of the mucosa and alter its solubilizing properties, thereby enhancing the partitioning of the peptide from the vehicle into the mucosa. The mucosal therapeutic and prophylactic compositions of the present invention may be supplemented with any suitable penetration-promoting agent that facilitates absorption, diffusion, or penetration of the peptide across mucosal barriers. The penetration promoter may be any promoter that is pharmaceutically acceptable.

To improve the transport characteristics of biologically active agents (including the therapeutic agent as described herein), for enhanced delivery across hydrophobic mucosal membrane barriers, according to at least some embodiments of the present invention there are provided techniques and reagents for charge modification of selected biologically active agents or delivery-enhancing agents described herein. In this regard, the relative permeabilities of macromolecules is generally be related to their partition coefficients. The degree of ionization of molecules, which is dependent on the pKa of the molecule and the pH at the mucosal membrane surface, also affects permeability of the molecules. Permeation and partitioning of biologically active agents for mucosal delivery may be facilitated by charge alteration or charge spreading of the active agent or permeabilizing agent, which is achieved, for example, by alteration of charged functional groups, by modifying the pH of the delivery vehicle or solution in which the active agent is delivered, or by coordinate administration of a charge- or pH-altering reagent with the active agent. Consistent with these general teachings, mucosal delivery of charged macromolecular species, such as a therapeutic agent as described herein, is substantially improved when the active agent is delivered to the mucosal surface in a substantially un-ionized, or neutral, electrical charge state.

Certain peptide and protein components of mucosal formulations for use according to at least some embodiments of the present invention will be charge modified to yield an increase in the positive charge density of the peptide or protein. These modifications extend also to cationization of peptide and protein conjugates, carriers and other delivery forms disclosed herein.

Another excipient that may be included in a trans-mucosal preparation is a degradative enzyme inhibitor. Any inhibitor that inhibits the activity of an enzyme to protect the biologically active agent(s) may be usefully employed in the compositions and methods according to at least some embodiments of the present invention. Useful enzyme inhibitors for the protection of biologically active proteins and peptides include, for example, soybean trypsin inhibitor, pancreatic trypsin inhibitor, chymotrypsin inhibitor and trypsin and chrymotrypsin inhibitor isolated from potato (*solanum tuberosum* L.) tubers. A combination or mixtures of inhibitors may be employed. The inhibitor(s) may be incorporated in or bound to a carrier, e.g., a hydrophilic polymer, coated on the surface of the dosage form which is to contact the nasal mucosa, or incorporated in the superficial phase of the surface, in combination with the biologically active agent or in a separately administered (e.g., pre-administered) formulation.

Additional enzyme inhibitors for use within the invention are selected from a wide range of non-protein inhibitors that vary in their degree of potency and toxicity.

As described in further detail below, immobilization of these adjunct agents to matrices or other delivery vehicles, or development of chemically modified analogues, may be readily implemented to reduce or even eliminate toxic effects, when they are encountered. Among this broad group of candidate enzyme inhibitors for use within the invention are organophosphorous inhibitors, such as diisopropylfluorophosphate (DFP) and phenylmethylsulfonyl fluoride (PMSF), which are potent, irreversible inhibitors of serine proteases (e.g., trypsin and chymotrypsin). Yet another type of enzyme inhibitory agent for use within the compositions according to at least some embodiments of the present invention are amino acids and modified amino acids that interfere with enzymatic degradation of specific therapeutic compounds.

According to an additional embodiment of the present invention there is provided a method of treating a disease, disorder or condition, as described herein, in a subject.

As used herein the term "treating" should be understood to encompass preventing, curing, reversing, attenuating, alleviating, minimizing, suppressing, reducing or halting the deleterious effects of the above-described diseases, disorders or conditions.

Treating, according to at least some embodiments of the present invention, can be effected by specifically upregulating the expression of at least one of the peptides in a subject.

Optionally, upregulation may be effected by administering to the subject at least one of the polypeptides according to at least some embodiments of the present invention (e.g., recombinant or synthetic) or an active portion thereof, as described herein. The polypeptide or peptide may optionally be administered as part of a pharmaceutical composition.

Upregulating expression of the therapeutic peptides according to at least some embodiments of the present invention may be effected via the administration of at least one of the exogenous polynucleotide sequences according to at least some embodiments of the present invention, ligated into a nucleic acid expression construct designed for expression of coding sequences in eukaryotic cells (e.g., mammalian cells). Accordingly, the exogenous polynucleotide sequence may be a DNA or RNA sequence encoding the peptides according to at least some embodiments of the present invention or active portions thereof.

It will be appreciated that the nucleic acid construct can be administered to the individual employing any suitable mode of administration including in vivo gene therapy (e.g., using viral transformation as described hereinabove). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

Such cells (i.e., which are transfected with the nucleic acid construct of the present invention) can be any suitable cells, such as kidney, bone marrow, keratinocyte, lymphocyte, adult stem cells, cord blood cells, embryonic stem cells which are derived from the individual and are transfected ex vivo with an expression vector containing the polynucleotide designed to express a polypeptide according to at least some embodiments of the present invention as described hereinabove.

Administration of the ex vivo transfected cells of the present invention can be effected using any suitable route such as intravenous, intra peritoneal, intra kidney, intra gastrointestinal track, subcutaneous, transcutaneous, intramuscular, intracutaneous, intrathecal, epidural and rectal. According to present embodiments, the ex vivo transfected cells of the present invention are introduced to the individual using intravenous, intra kidney, intra gastrointestinal track and/or intra peritoneal administrations.

The ex vivo transfected cells of the present invention can be derived from either autologous sources such as self bone marrow cells or from allogeneic sources such as bone marrow or other cells derived from non-autologous sources. Since non-autologous cells are likely to induce an immune reaction when administered to the body several approaches have been developed to reduce the likelihood of rejection of non-autologous cells. These include either suppressing the recipient immune system or encapsulating the non-autologous cells or tissues in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. *Technology of mammalian cell encapsulation. Adv Drug Deliv Rev.* 2000; 42: 29-64).

Methods of preparing microcapsules are known in the arts and include for example those disclosed by Lu M Z, et al., *Cell encapsulation with alginate and alpha-phenoxycinnamylidene-acetylated poly(allylamine). Biotechnol Bioeng.* 2000, 70: 479-83, Chang T M and Prakash S. *Procedures for microencapsulation of enzymes, cells and genetically engineered microorganisms. Mol. Biotechnol.* 2001, 17: 249-60, and Lu M Z, et al., *A novel cell encapsulation method using photosensitive poly(allylamine alpha-cyanocinnamylidene-acetate). J Microencapsul.* 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. *Multi-layered microcapsules for cell encapsulation Biomaterials.* 2002 23: 849-56).

Other microcapsules are based on alginate, a marine polysaccharide (Sambanis, A. *Encapsulated islets in diabetes treatment. Diabetes Thechnol. Ther.* 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

The subject according to at least some embodiments of the present invention is a mammal, preferably a human (male or female) which is diagnosed with at least one of the disease, disorder or conditions described hereinabove, or alternatively is predisposed to at least one type of disease, disorder or conditions described hereinabove.

In at least some embodiments, the subject invention further provides a use of a peptide according to at least some embodiments of the present invention or a homolog or derivative thereof for the manufacture of a medicament. In at least some embodiments, the subject invention also provides an antibody according to at least some embodiments of the present invention for the manufacture of a medicament. In at least some embodiments, the subject invention additionally provides a fusion protein according to at least some embodiments of the present invention for the manufacture of a medicament. In at least some embodiments, the subject invention also provides a peptide according to at least some embodiments of the present invention or a homolog or derivative thereof for use in therapy. In at least some embodiments, the subject invention also provides an antibody according to at least some embodiments of the present invention for use in therapy. In at least some embodiments, the subject invention additionally provides a fusion protein according to at least some embodiments of the present invention for use in therapy.

In one embodiment, the medicament or therapy is for the treatment of cancer.

The term "therapy for cancer" or "treating cancer" as used herein should be understood to encompass achieving: a decrease in tumor size; a decrease in rate of tumor growth; a decrease or regression in tumor migration; a decrease or regression in tumor epithelial-to-mesenchymal transition (EMT); stasis of tumor size; a decrease or regression in invasiveness of the cancer; a decrease or regression in the rate of progression of the tumor from one stage to the next; inhibition of tumor growth in a tissue of a mammal having a malignant cancer; a decrease or regression in the number of metastasis; a decrease or regression in the number of additional metastasis; control of establishment of metastases; inhibition of tumor metastases formation; regression of established tumors as well as decrease in the angiogenesis induced by the cancer. The term "therapy for cancer" and "treating cancer" as used herein should also be understood to encompass prophylaxis such as prevention as cancer reoccurs after previous treatment (including surgical removal) and prevention of cancer in an individual prone to develop cancer. Subjects may be prone to develop cancer genetically or due to life style, chronic inflammation, hepatitis C(HCV), inflammatory bowel disease (IBD) and so forth.

The term "cancer" as used herein should be understood to encompass any neoplastic disease (whether invasive or metastatic) which is characterized by abnormal and uncontrolled cell division causing malignant growth or tumor. Non-limiting examples of cancer which may be treated with a peptide according to at least some embodiments of the present invention are solid tumors, sarcomas, hematological malignancies, including but not limited to breast cancer (e.g. breast carcinoma), cervical cancer, ovary cancer (ovary carcinoma), endometrial cancer, melanoma, bladder cancer (bladder carcinoma), lung cancer (e.g. adenocarcinoma and non-small cell lung cancer), pancreatic cancer (e.g. pancreatic carcinoma such as exocrine pancreatic carcinoma), colon cancer (e.g. colorectal carcinoma, such ascolon adenocarcinoma and colon adenoma), prostate cancer including the advanced disease, hematopoietic tumors of lymphoid lineage (e.g. leukemia, acute lymphocytic leukemia, chronic lymphocytic leukemia, B-cell lymphoma, Burkitt's lymphoma, multiple myeloma, Hodgkin's lymphoma, Non-Hodgkin's lymphoma), myeloid leukemia (for example, acute myelogenous leukemia (AML), chronic myelogenous leukemia), thyroid cancer, thyroid follicular cancer, myelodysplastic syndrome (MDS), tumors of mesenchymal origin (e.g. fibrosarcomas and rhabdomyosarcomas), melanoma, uveal melanoma, teratocarcinoma, neuroblastoma, glioma, glioblastoma, benign tumor of the skin (e.g. keratoacanthomas), renal cancer, anaplastic large-cell lymphoma, esophageal squamous cells carcinoma, hepatocellular carcinoma, follicular dendritic cell carcinoma, intestinal cancer, muscle-invasive cancer, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, prostatic hypertrophy, myelodysplasia, Waldenstrom's macroglobinaemia, nasopharyngeal, neuroendocrine cancer, myelodysplastic syndrome, mesothelioma, angiosarcoma, Kaposi's sarcoma, carcinoid, oesophagogastric, fallopian tube cancer, peritoneal cancer, papillary serous mullerian cancer, malignant ascites, gastrointestinal stromal tumor (GIST), and a hereditary cancer syndrome such as Li-Fraumeni syndrome and Von Hippel-Lindau syndrome (VHL).

In another embodiment, the cancer is inflammation-induced cancer.

One of the mechanisms for tumorigenesis (the process involved in the production of a new tumor or tumors) is induced by chronic inflammation (Pikarsky E, et al., Nature 2004 Sep. 23; 431(7007):461-6; Moss S F, Blaser M J. Nat Clin Pract Oncol. 2005 February; 2(2):90-7; Karin M, Greten F R. Nat Rev Immunol. 2005 October; 5(10):749-59.) Chronic inflammation is also a mechanism for tumor maintenance.

Without being bound by theory, when used against inflammatory diseases and inflammatory environments that support tumorigenesis and the various steps of tumor progression including invasiveness, migration, epithelial-to-mesenchymal transition (EMT), and metastasis, peptides according to at least some embodiments of the present invention reduce the circulating levels of inflammatory cytokines such as, but not limited to, IL-1beta, TNFalpha, IL-6 and inflammatory chemokines such as, but not limited to, MIP2 and MIP1 alpha.

The peptides according to at least some embodiments of the present invention attenuate inflammation-induced tumorigenesis and tumor maintenance.

In one embodiment, the cancer is invasive. In another embodiment, the cancer is metastatic.

In another embodiment, the medicament or therapy is for the treatment of a respiratory disease.

The term "a respiratory disease" as used herein should be understood to encompass any disease of the respiratory system. These include diseases of the lung, pleural cavity, bronchial tubes, trachea, upper respiratory tract and of the nerves and muscles of breathing. Respiratory diseases range from mild and self-limiting such as the common cold to life-threatening such as bacterial pneumonia or pulmonary embolism. Non-limiting examples of respiratory diseases which may be treated with a peptide according to at least some embodiments of the present invention are asthma, bronchial disease, lung diseases, chronic obstructive pulmonary disease (COPD), Acute Respiratory Distress Syndrome (ARDS), severe acute respiratory syndrome (SARS), fibrosis related asthma, cystic fibrosis, acute lung injury, Emphysema, chronic bronchitis, pneumonia, and pulmonary hypertension.

In yet another embodiment, the medicament or therapy is for the treatment of a metabolic disorder.

The term "metabolic disorder" (congenital metabolic diseases or inherited metabolic diseases) as used herein should be understood to encompass carbohydrate metabolism disorders, amino acid metabolism disorders, organic acid metabolism disorders, fat and lipid metabolism disorders, lysosomal storage diseases and so forth. Non-limiting examples of metabolic disorders which may be treated with a peptide according to at least some embodiments of the present invention are metabolic syndrome X, syndrome X, insulin resistance syndrome, Reaven's syndrome, CHAOS, diabetes, diabetes mellitus, lipodystrophy, hyperthyroidism, glaucoma, hyperlipidaemia, dislipidemia, hypercholesterolemia, non-insulin dependent diabetes, energy control disorders, appetite control, and obesity.

In yet another embodiment, the medicament or therapy is for the treatment of a fibrotic or connective tissue related condition.

The term "fibrotic or connective tissue related condition" as used herein should be understood to encompass any disease, condition or disorder in which a connective tissue is affected. Connective tissue is mesodermally derived tissue that may be specialized. For example, cartilage and bone are specialised connective tissue, while the term is also reserved for less specialized tissue that is rich in extracellular matrix (collagen, proteoglycan etc.) and that surrounds other more highly ordered tissues and organs. Connective tissue related conditions are characterized by abnormal structure or function of one or more of the elements of connective tissue, e.g., collagen, elastin, or the mucopolysaccharides. Non-limiting examples of fibrotic or connective tissue related conditions which may be treated with a peptide according to at least some embodiments of the present invention are fibrotic or connective tissue related conditions involving tissue remodeling following e.g. inflammation, including but not limited to endomyocardial and cardiac fibrosis, mediastinal fibrosis, idiopathy pulmonary fibrosis, pulmonary fibrosis, retroperitoneal fibrosis, fibrosis of the spleen, fibrosis of the pancreas, hepatic fibrosis (cirrhosis) alcohol and non-alcohol related (including viral infection such as HAV, HBV and HCV), fibromatosis, uterine fibroids, angiofibroma, granulomatous lung disease, glomerulonephritis, endometrial fibrosis and endometriosis, diabetes related wound fibrosis, lymphangiogenesis, fibrodysplasia ossificans progressive, osteomyelitis, scar keloid, warts, synovitis, osteophyte, pannus growth, peritoneal sclerosis (in dialysis patients), ascites, hemophilic joints, and myelofibrosis.

In yet another embodiment, the medicament or therapy is for the treatment of an urogenital disorder.

The term "urogenital related disorder" as used herein should be understood to encompass any disorder involving the urinary and/or the genital organs and their function. Non-limiting examples of urogenital related disorders which may be treated with a peptide according to at least some embodiments of the present invention may involve tissue remodeling and neovascularization, follicular cyst, ovarian cyst, ovarian hyper-stimulation.

In yet another embodiment, the medicament or therapy is for the treatment of an ocular disease.

The term "ocular disease" as used herein should be understood to encompass any disease, condition or disorder of the eye (including its internal components such as eyelids, adnexa, conjunctiva, sclera, cornea, uvea, vitreous and retina, optic nerve) and/or vision conditions and disorders. Non-limiting examples of ocular diseases which may be treated with a peptide according to at least some embodiments of the present invention are retinal angiogenesis in a number of human ocular diseases such as ocular neovascularisation, retinopathies (including diabetic retinopathy and retinopathy of prematurity), age-related macular degeneration, macular oedema (i.e diabetic), trachoma, glaucoma, dry eye syndrome, neuro-ophthalmic disease, oculosystemic disease, eye infections, eye inflammation and corneal neovascularization.

In yet another embodiment, the medicament or therapy is for the treatment of a vascular anomaly related disorder.

The term "a vascular anomaly" as used herein should be understood to encompass any birthmark and/or vascular anomaly related disorder which may appear on any part of the body both externally or in internal organs. Non-limiting examples of vascular anomaly related disorders which may be treated with a peptide according to at least some embodiments of the present invention are vascular permeability, plasma leakage, venous malformation (VM), hemangioblastoma, hemangiomas, intramuscular hemangiomas, brain arteriovenous malformations (BAVM), arteriosclerosis, thrombosis, leukomalacia (PLV), Hereditary Hemorrhagic telangiectasia (HHT), Ataxia telangiectasia and Osler-Weber syndrome.

In yet another embodiment, the medicament or therapy is for the treatment of a cardiovascular disease.

The term "cardiovascular disease" as used herein should be understood to encompass any disease, disorder or condition of the heart and/or blood vessels (arteries and veins that affect the cardiovascular system). Non-limiting examples of cardiovascular diseases which may be treated with a peptide according to at least some embodiments of the present invention are myocarditis, cerebrovascular accident, mitral valve regurgitation, hypotension, arterial or post-transplantational atherosclerosis, fibrosis, thrombosis, and platelet aggregation.

In yet another embodiment, the medicament or therapy is for an inflammatory disorder or for the treatment of an inflammatory condition associated with an infection.

The term "an inflammatory condition associated with an infection" as used herein should be understood to encompass any inflammatory condition associated with an infection. Non-limiting examples of such inflammatory conditions (i.e. sepsis-induced multiple organ dysfunction syndrome) associated with an infection are the result of bacterial infections, viral infections, protozoal infections, helminthic infections and so forth.

The term "inflammatory disorder" as used herein should be understood to encompass any disease, disorder or condition that may be characterized by activation and stimulation of the immune system to abnormal levels, caused by pathogens, damaged cells, irritants and so forth. Non-limiting examples of inflammatory disorders which may be treated with a peptide according to at least some embodiments of the present invention are peptic ulcers, gastritis, gout, gouty arthritis, arthritis, rheumatoid arthritis, inflammatory bowel disease, Crohn's disease, ulcerative colitis, ulcers, chronic bronchitis, asthma, allergy, acute lung injury, pulmonary inflammation, airway hyper-responsiveness, vasculitis, septic shock and inflammatory skin disorders, including but not limited to psoriasis, atopic dermatitis, and eczema.

In yet another embodiment, the medicament or therapy is for the treatment of a chronic inflammatory or autoimmune disease.

The term "chronic inflammatory and/or autoimmune disease" as used herein should be understood to encompass any disease, disorder or condition characterized by infiltration of inflammatory cells accompanied by dysregulation of the immune response and destruction of healthy tissue and in some cases production of auto-antibodies. Non-limiting examples of chronic inflammatory or autoimmune diseases which may be treated by a peptide according to at least some embodiments of the present invention are multiple sclerosis, psoriasis, rheumatoid arthritis, systemic lupus erythematosus, ulcerative colitis, Crohn's disease, transplant rejection, immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitus, Goodpasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis, thyroditis. allergic oedema, and granulomas.

In yet another embodiment, the medicament or therapy is for the treatment of a bone disease or bone-related disorder.

The term "bone disease or bone-related disorder" as used herein should be understood to encompass any disease disorder or condition, selected from a group consisting of but not limited to Osteoporosis; Osteoarthritis; Osteopetrosis; Bone inconsistency; bone weakness; bone brittleness; degenerative joint disease; Osteosarcoma; and Cancer metastasis to the bone.

In yet another embodiment, the medicament or therapy is for the treatment or management of pain.

The term "pain" as used herein should be understood to encompass any pain. Non-limiting examples of pain which may be treated by a peptide according to at least some embodiments of the present invention are complex regional pain, muscoskeletal pain, neuropathic pain, nociceptive pain, psychogenic pain, post-herpetic pain, pain associated with cancer, post-operative pain, acute pain, chronic pain, phantom pain, referred pain and so forth.

The term "pain management" as used herein should be understood to refer to the control of pain or discomfort through a combined approach including pharmacological treatment using at least one peptide, homolog or derivative according to at least some embodiments of the present invention, or a pharmaceutical composition thereof in combination with other compositions known and used to treat pain (e.g. analgesics, narcotics, NSAIDs, tricyclic antidepressants, anticonvulsants and so forth), non-pharmacological measures (such as interventional procedures, physical therapy, physical exercise, application of ice or heat, acupuncture and so forth) and physiological measures (such as biofeedback, cognitive therapy and so forth).

In at least some embodiments, the subject invention further provides a method of treating cancer, comprising administering a pharmaceutically effective amount of a peptide according to at least some embodiments of the present invention or a homolog or a derivative thereof and a pharmaceutically acceptable carrier to a subject in need thereof. In at least some embodiments, the subject invention further provides a method of treating cancer, comprising administering a pharmaceutically effective amount of an antibody according to at least some embodiments of the present invention and a pharmaceutically acceptable carrier to a subject in need thereof. In at least some embodiments, the subject invention further provides a method of treating cancer, comprising administering a pharmaceutically effective amount of a fusion protein according to at least some embodiments of the present invention and a pharmaceutically acceptable carrier to a subject in need thereof.

In at least some embodiments, the subject invention further provides a method of treating a respiratory disease comprising administering a pharmaceutically effective amount of a peptide according to at least some embodiments of the present invention or a homolog or a derivative thereof and a pharmaceutically acceptable carrier to a subject in need thereof. In at least some embodiments, the subject invention further provides a method of treating a respiratory disease, comprising administering a pharmaceutically effective amount of an antibody according to at least some embodiments of the present invention and a pharmaceutically acceptable carrier to a subject in need thereof. In at least some embodiments, the subject invention further provides a method of treating a respiratory disease, comprising administering a pharmaceutically effective amount of a fusion protein according to at least some embodiments of the present invention and a pharmaceutically acceptable carrier to a subject in need thereof.

In at least some embodiments, the subject invention further provides a method of treating a metabolic disorder comprising administering a pharmaceutically effective amount of a peptide according to at least some embodiments of the present invention or a homolog or a derivative thereof and a pharmaceutically acceptable carrier to a subject in need thereof. In at least some embodiments, the subject invention further provides a method of treating a metabolic disorder, comprising administering a pharmaceutically effective amount of an antibody according to at least some embodiments of the present invention and a pharmaceutically acceptable carrier to a subject in need thereof. In at least some embodiments, the subject invention further provides a method of treating a metabolic disorder, comprising administering a pharmaceutically effective amount of a fusion protein according to at least some embodiments of the present invention and a pharmaceutically acceptable carrier to a subject in need thereof.

In at least some embodiments, the subject invention further provides a method of treating a fibrotic or connective tissue related condition, comprising administering a pharmaceutically effective amount of a peptide according to at least some embodiments of the present invention or a homolog or a derivative thereof and a pharmaceutically acceptable carrier to a subject in need thereof. In at least some embodiments, the subject invention further provides a method of treating a fibrotic or connective tissue related condition, comprising administering a pharmaceutically effective amount of an antibody according to at least some embodiments of the present invention and a pharmaceutically acceptable carrier to a subject in need thereof. In at least some embodiments, the subject invention further provides a method of treating a fibrotic or connective tissue related condition, comprising administering a pharmaceutically effective amount of a fusion protein according to at least some embodiments of the present invention and a pharmaceutically acceptable carrier to a subject in need thereof.

In at least some embodiments, the subject invention further provides a method of treating an urogenital disorder, comprising administering a pharmaceutically effective amount of a peptide according to at least some embodiments of the present invention or a homolog or a derivative thereof and a pharmaceutically acceptable carrier to a subject in need thereof. In at least some embodiments, the subject invention further provides a method of treating an urogenital disorder, comprising administering a pharmaceutically effective amount of an antibody according to at least some embodiments of the present invention and a pharmaceutically acceptable carrier to a subject in need thereof. In at least some embodiments, the subject invention further provides a method of treating an urogenital disorder, comprising administering a pharmaceutically effective amount of a fusion protein according to at least some embodiments of the present invention and a pharmaceutically acceptable carrier to a subject in need thereof.

In at least some embodiments, the subject invention further provides a method of treating an ocular disease, comprising administering a pharmaceutically effective amount of a peptide according to at least some embodiments of the present invention or a homolog or a derivative thereof and a pharmaceutically acceptable carrier to a subject in need thereof. In at least some embodiments, the subject invention further provides a method of treating an ocular disease, comprising administering a pharmaceutically effective amount of an antibody according to at least some embodiments of the present invention and a pharmaceutically acceptable carrier to a subject in need thereof. In at least some embodiments, the subject invention further provides a method of treating an ocular disease, comprising administering a pharmaceutically effective amount of a fusion protein according to at least some embodiments of the present invention and a pharmaceutically acceptable carrier to a subject in need thereof.

In at least some embodiments, the subject invention further provides a method of treating a vascular anomaly related disorder, comprising administering a pharmaceutically effective amount of a peptide according to at least some embodiments of the present invention or a homolog or a derivative thereof and a pharmaceutically acceptable carrier to a subject in need thereof. In at least some embodiments, the subject invention further provides a method of treating a vascular anomaly related disorder, comprising administering a pharmaceutically effective amount of an antibody according to at least some embodiments of the present invention and a pharmaceutically acceptable carrier to a subject in need thereof. In at least some embodiments, the subject invention further provides a method of treating a vascular anomaly related disorder, comprising administering a pharmaceutically effective amount of a fusion protein according to at least some embodiments of the present invention and a pharmaceutically acceptable carrier to a subject in need thereof.

In at least some embodiments, the subject invention further provides a method of treating a cardiovascular disease, comprising administering a pharmaceutically effective amount of a peptide according to at least some embodiments of the present invention or a homolog or a derivative thereof and a pharmaceutically acceptable carrier to a subject in need thereof. In at least some embodiments, the subject invention further provides a method of treating a cardiovascular disease, comprising administering a pharmaceutically effective amount of an antibody according to at least some embodiments of the present invention and a pharmaceutically acceptable carrier to a subject in need thereof. In at least some embodiments, the subject invention further provides a method of treating a cardiovascular disease, comprising administering a pharmaceutically effective amount of a fusion protein according to at least some embodiments of the present invention and a pharmaceutically acceptable carrier to a subject in need thereof.

In at least some embodiments, the subject invention further provides a method of treating inflammatory condition associated with an infection or an inflammatory disorder, comprising administering a pharmaceutically effective amount of a peptide according to at least some embodiments of the present invention or a homolog or a derivative thereof and a pharmaceutically acceptable carrier to a subject in need thereof. In at least some embodiments, the subject invention further provides a method of treating a inflammatory condition associated with an infection or an inflammatory disorder, comprising administering a pharmaceutically effective amount of an antibody according to at least some embodiments of the present invention and a pharmaceutically acceptable carrier to a subject in need thereof. In at least some embodiments, the subject invention further provides a method of treating inflammatory condition associated with an infection or an inflammatory disorder, comprising administering a pharmaceutically effective amount of a fusion protein according to at least some embodiments of the present invention and a pharmaceutically acceptable carrier to a subject in need thereof.

In at least some embodiments, the subject invention further provides a method of treating a chronic inflammatory or autoimmune disease, comprising administering a pharmaceutically effective amount of a peptide according to at least some embodiments of the present invention or a homolog or a derivative thereof and a pharmaceutically acceptable carrier to a subject in need thereof. In at least some embodiments, the subject invention further provides a method of treating a chronic inflammatory or autoimmune disease, comprising administering a pharmaceutically effective amount of an antibody according to at least some embodiments of the present invention and a pharmaceutically acceptable carrier to a subject in need thereof. In at least some embodiments, the subject invention further provides a method of treating a chronic inflammatory or autoimmune disease, comprising administering a pharmaceutically effective amount of a fusion protein according to at least some embodiments of the present invention and a pharmaceutically acceptable carrier to a subject in need thereof.

In at least some embodiments, the subject invention further provides a method of treating a bone disease or bone-related disorder, comprising administering a pharmaceutically effective amount of a peptide according to at least some embodiments of the present invention or a homolog or a derivative thereof and a pharmaceutically acceptable carrier to a subject in need thereof. In at least some embodiments, the subject invention further provides a method of treating a bone disease or bone-related disorder, comprising administering a pharmaceutically effective amount of an antibody according to at least some embodiments of the present invention and a pharmaceutically acceptable carrier to a subject in need thereof. In at least some embodiments, the subject invention further provides a method of treating bone disease or bone-related disorder, comprising administering a pharmaceutically effective amount of a fusion protein according to at least some embodiments of the present invention and a pharmaceutically acceptable carrier to a subject in need thereof.

In at least some embodiments, the subject invention further provides a method for treating pain, comprising administering a pharmaceutically effective amount of a peptide according to at least some embodiments of the present invention or a homolog or a derivative thereof and a pharmaceutically acceptable carrier to a subject in need thereof. In at least some embodiments, the subject invention further provides a method of treating pain, comprising administering a pharmaceutically effective amount of an antibody according to at least some embodiments of the present invention and a pharmaceutically acceptable carrier to a subject in need thereof. In at least some embodiments, the subject invention further provides a method of treating pain, comprising administering a pharmaceutically effective amount of a fusion protein according to at least some embodiments of the present invention and a pharmaceutically acceptable carrier to a subject in need thereof.

It will be appreciated that treatment of the above-described diseases according to the present invention may be combined with other treatment methods known in the art (i.e., combination therapy). Thus, treatment of diseases using a peptide of the present invention may be combined with one or more of, for example, radiation therapy, antibody therapy, chemotherapy, photodynamic therapy, surgery or in combination therapy with conventional drugs, such as immunosuppressants or cytotoxic drugs.

A peptide or pharmaceutical composition according to at least some embodiments of the present invention may also be administered in conjunction with other compounds. For example, the combination therapy can include a peptide of the present invention combined with at least one other therapeutic or immune modulatory agent, including, but not limited to, antibodies (e.g. bevacizutnab, erbitux), peptides, peptibodies, small molecules, chemotherapeutic agents such as cytotoxic and cytostatic agents (e.g. paclitaxel, cisplatin, vinorelbine, docetaxel, gemcitabine, temozolomide, irinotecan, 5FU, carboplatin), immunological modifiers such as interferons and interleukins, growth hormones or other cytokines, folic acid, vitamins, minerals, aromatase inhibitors, RNAi, Histone Deacetylase Inhibitors, proteasome inhibitors, and so forth.

Without being bound by theory, it is possible that a peptide according to at least some embodiments of the present invention interferes with intra-molecular segment-segment interactions of Ang1, Ang2 or Ang4 proteins, respectively, thereby preventing these proteins from reaching their active state. Without being bound by theory, the mechanism of action of the bioactive antiangiogenic peptides of this invention may be by their binding to their parent proteins (Ang1, Ang2 or Ang4, respectively) to the segment corresponding to the partner helix of each bioactive peptide according to at least some embodiments of the present invention.

In at least some embodiments, the subject invention further provides a (poly) nucleotide sequence encoding a peptide according to at least some embodiments of the present invention or a homolog thereof.

As used herein, "a (poly)nucleotide sequence encoding a peptide according to at least some embodiments of the present invention or a homolog thereof" should be understood to encompass any nucleotide sequence encoding a peptide according to at least some embodiments of the present invention or a homolog thereof. As known to a person skilled in the art, due to the known degeneracy of the genetic code (codon variability), amino acids can be coded for by more than one codon. Indeed, some amino acids have as many as six alternative codons (e.g. leucine) while some others have a single, required codon (e.g. methionine).

In one embodiment, a polynucleotide sequence according to at least some embodiments of the present invention is that encoding SEQ ID NO:1. In one embodiment, the nucleotide sequence is that depicted in SEQ ID NO:23.

In one embodiment, a polynucleotide sequence according to at least some embodiments of the present invention is that encoding SEQ ID NO:2. In one embodiment, the nucleotide sequence is that depicted in SEQ ID NO:24.

In one embodiment, a polynucleotide sequence according to at least some embodiments of the present invention is that encoding SEQ ID NO:3. In one embodiment, the nucleotide sequence is that depicted in SEQ ID NO:25.

In one embodiment, a polynucleotide sequence according to at least some embodiments of the present invention is that encoding SEQ ID NO:4. In one embodiment, the nucleotide sequence is that depicted in SEQ ID NO:26.

In one embodiment, a polynucleotide sequence according to at least some embodiments of the present invention is that encoding SEQ ID NO:5. In one embodiment, the nucleotide sequence is that depicted in SEQ ID NO:27.

In one embodiment, a polynucleotide sequence according to at least some embodiments of the present invention is that encoding SEQ ID NO:6. In one embodiment, the nucleotide sequence is that depicted in SEQ ID NO:28.

In one embodiment, a polynucleotide sequence according to at least some embodiments of the present invention is that encoding SEQ ID NO:7. In one embodiment, the nucleotide sequence is that depicted in SEQ ID NO:29.

In one embodiment, a polynucleotide sequence according to at least some embodiments of the present invention is that encoding SEQ ID NO:8. In one embodiment, the nucleotide sequence is that depicted in SEQ ID NO:30.

In one embodiment, a polynucleotide sequence according to at least some embodiments of the present invention is that encoding SEQ ID NO:9. In one embodiment, the nucleotide sequence is that depicted in SEQ ID NO:31.

In one embodiment, a polynucleotide sequence according to at least some embodiments of the present invention is that encoding SEQ ID NO:10. In one embodiment, the nucleotide sequence is that depicted in SEQ ID NO:32.

In one embodiment, a polynucleotide sequence according to at least some embodiments of the present invention is that encoding SEQ ID NO:11. In one embodiment, the nucleotide sequence is that depicted in SEQ ID NO:33.

In one embodiment, a polynucleotide sequence according to at least some embodiments of the present invention is that encoding SEQ ID NO:12. In one embodiment, the nucleotide sequence is that depicted in SEQ ID NO:34.

In one embodiment, a polynucleotide sequence according to at least some embodiments of the present invention is that encoding SEQ ID NO:13. In one embodiment, the nucleotide sequence is that depicted in SEQ ID NO:35.

In one embodiment, a polynucleotide sequence according to at least some embodiments of the present invention is that encoding SEQ ID NO:14. In one embodiment, the nucleotide sequence is that depicted in SEQ ID NO:36.

In one embodiment, a polynucleotide sequence according to at least some embodiments of the present invention is that encoding SEQ ID NO:15. In one embodiment, the nucleotide sequence is that depicted in SEQ ID NO:37.

In one embodiment, a polynucleotide sequence according to at least some embodiments of the present invention is that encoding SEQ ID NO:16. In one embodiment, the nucleotide sequence is that depicted in SEQ ID NO:38.

In one embodiment, a polynucleotide sequence according to at least some embodiments of the present invention is that encoding SEQ ID NO:17. In one embodiment, the nucleotide sequence is that depicted in SEQ ID NO:39.

In one embodiment, a polynucleotide sequence according to at least some embodiments of the present invention is that encoding SEQ ID NO:18. In one embodiment, the nucleotide sequence is that depicted in SEQ ID NO:40.

In one embodiment, a polynucleotide sequence according to at least some embodiments of the present invention is that encoding SEQ ID NO:19. In one embodiment, the nucleotide sequence is that depicted in SEQ ID NO:41.

In one embodiment, a polynucleotide sequence according to at least some embodiments of the present invention is that encoding SEQ ID NO:20. In one embodiment, the nucleotide sequence is that depicted in SEQ ID NO:42.

In one embodiment, a polynucleotide sequence according to at least some embodiments of the present invention is that encoding SEQ ID NO:21. In one embodiment, the nucleotide sequence is that depicted in SEQ ID NO:43.

In one embodiment, a polynucleotide sequence according to at least some embodiments of the present invention is that encoding SEQ ID NO:22. In one embodiment, the nucleotide sequence is that depicted in SEQ ID NO:44.

Antibodies and Fragments and Derivatives Thereof, and/or Fusion or Conjugate Proteins According to some embodiments of the present invention, there is provided an antibody, fragment or derivative thereof with specific binding affinity to epitopes according to at least some embodiments of the present invention as described herein. Also described herein are fusion and/or conjugate proteins according to at least some embodiments of the present invention.

The term "antibody" as used herein should be understood to encompass a polypeptide ligand substantially encoded by an immunoglobulin gene or immunoglobulin genes, or fragments thereof, which specifically bind and recognize an epitope (e.g., an antigen).

The antibody can be provided as, e.g., an intact immunoglobulin or as a fragment, e.g., a fragment produced by digestion with various peptidases. This includes, e.g. Fab' and F(ab)'$_2$ Fv fragments (defined as a genetically engineered fragment containing the variable region of the light chain and the variable region of the heavy chain expressed as two chains) and single chain antibodies ("SCAs"), genetically engineered molecules containing the variable region of the light chain and the variable region of the heavy chain, linked by a suitable polypeptide linker as a genetically fused single chain molecule.

The term "antibody," as used herein, also includes antibody fragments produced e.g. by modification of whole antibodies or synthesized de novo using recombinant DNA methodologies.

The term "antibody" includes, but is not limited to, polyclonal antibodies, monoclonal antibodies, chimeric antibodies, humanized antibodies, or single chain antibodies. In one embodiment, an antibody according to at least some embodiments of the present invention is a monoclonal antibody.

"Fc" portion of an antibody refers to that portion of an immunoglobulin heavy chain that comprises one or more heavy chain constant region domains, CH1, CH2 and CH3, but does not include the heavy chain variable region.

An antibody according to at least some embodiments of the present invention may be conjugated or coupled to e.g. a detectable label, a radioactive label, an enzyme, a fluorescent label, a luminescent label, a bioluminescent label, a therapeutic agent and so forth.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments may be prepared by proteolytic hydrolysis of the antibody or by expression in e.g. *E. coli* or mammalian cells (e.g. Chinese hamster ovary cell culture or other protein expression systems) of DNA encoding the fragment. Antibody fragments can be obtained by pepsin or papain digestion of whole antibodies by conventional methods.

The antibody may e.g. correspond to a single complementary-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry *Methods*, 2: 106-10 (1991). Humanized forms of non-human (e.g., murine) antibodies may be chimeric molecules of immunoglobulins, or immunoglobulin chains or fragments thereof (such as Fv, Fab, Fab', F(ab') or other antigen-binding subsequences of antibodies) which contain a short sequence, typically of about 20-50 amino acids, derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues.

Humanized antibodies may also comprise residues which are found neither in the recipient antibody nor in the imported CDR or framework (FR) sequences. In general, the humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be performed by, for example, substituting rodent CDRs or other CDR sequences for the corresponding sequences of a human antibody. Accordingly, such humanized antibodies are chimeric antibodies (see e.g. U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in e.g. rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)1 The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)]. Similarly, human antibodies can be prepared by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., *Bio/Technology* 10: 779-783 (1992); Lonberg et al., *Nature* 368: 856-859 (1994); Morrison, *Nature* 368 812-13 (1994); Fishwild et al., *Nature Biotechnology* 14, 845-51 (1996); Neuberger, *Nature Biotechnology* 14: 826 (1996); and Lonberg and Huszar, *Intern. Rev. Immunol.* 13, 65-93 (1995).

The antibody preferably binds specifically (or selectively) to a peptide according to at least some embodiments of the present invention. The term "specifically (or selectively) binds" to an antibody or the term "specifically (or selectively) immunoreactive with," when referring to a protein or peptide, refers to a binding reaction that is determinative of the presence of the peptide in a heterogeneous population of peptide and other biologics. Thus, under designated immunoassay conditions, the specified antibodies bind to a particular peptide at least twice the background and do not substantially bind in a significant amount to other proteins or peptides present in the sample. Specific binding to an antibody under such conditions may require an antibody that is selected for its specificity to a particular peptide. A variety of immunoassay formats may be used to select antibodies specifically immunoreactive with a particular peptide. For example, solid-phase ELISA immunoassays are routinely used to select antibodies specifically immunoreactive with a protein or a peptide (see, e.g., Harlow & Lane, Antibodies, A Laboratory Manual (1988)). Typically a specific or selective reaction will be at least twice the background signal or noise and more typically more than 10 to 100 times background.

In at least some embodiments, the subject invention provides an antibody according to at least some embodiments of the present invention for use in therapy. In at least some embodiments, the subject invention also provides a use of an antibody according to at least some embodiments of the present invention for the manufacture of a medicament. In at least some embodiments, the subject invention further provides a pharmaceutical composition comprising an antibody according to at least some embodiments of the present invention.

In at least some embodiments, the subject invention further provides a method of treating conditions, disorders and diseases where treatment or prevention of undesired angiogenesis can be of therapeutic value, comprising administering a pharmaceutically effective amount of an antibody according to at least some embodiments of the present invention or a pharmaceutical composition comprising the antibody according to at least some embodiments of the present invention, to a subject in need thereof.

In at least some embodiments, the subject invention further provides a method of treating conditions, disorders and diseases, selected from but not limited to cancer, respiratory diseases, metabolic disorders, fibrotic and connective tissue related conditions, urogenital disorders, ocular diseases, vascular anomalies, cardiovascular diseases and their complications, inflammatory conditions associated with an infection or inflammatory disorders, chronic inflammatory and autoimmune diseases, bone disease or bone-related disorder and pain, comprising administering a pharmaceutically effective amount of an antibody according to at least some embodiments of the present invention or a pharmaceutical composition comprising the antibody according to at least some embodiments of the present invention, to a subject in need thereof.

In at least some embodiments, the subject invention further provides a peptide of the present invention conjugated or fused to another peptide or to a polypeptide. Such conjugates/fusion proteins may be prepared by any methodology known in the art such as, but not limited to, the preparation of conjugates/fusion proteins using chemical synthesis or using recombinant technology.

Examples of peptides or polypeptides which may be conjugated/fused to a peptide according to at least some embodiments of the present invention are multiple antigenic peptides (MAP), Fc chains of immunoglobulins and signal sequences.

In one embodiment, a peptide or a polypeptide which may be conjugated to a peptide according to at least some embodiments of the present invention is an immunoglobulin sequence (e.g., an IgG sequence). Non-limiting examples of immunoreactive ligands (which may e.g. serve as a targeting moiety) are an antigen-recognizing immunoglobulin (also referred to herein as "antibody") and an antigen-recognizing fragment thereof, e.g., immunoglobulins that can recognize a tumor-associated antigen.

As used herein, "immunoglobulin" should be understood to refer to any recognized class or subclass of immunoglobulins such as IgG, IgA, IgM, IgD, or IgE. In one embodiment, the immunoglobulin is within the IgG class of immunoglobulins. The immunoglobulin may be derived from any species, such as, but not limited to human, murine, or rabbit origin. In addition, the immunoglobulin may be polyclonal or monoclonal. In one embodiment, the immunoglobulin is monoclonal.

A conjugate/fusion protein may be prepared from a peptide according to the present invention by fusion with e.g. a portion of an immunoglobulin comprising a constant region of an immunoglobulin. In one embodiment, the portion of the immunoglobulin comprises a heavy chain constant region. In another embodiment, the heavy chain constant region comprises a human heavy chain constant region. In yet another embodiment, the heavy chain constant region is an IgG heavy chain constant region. In yet another embodiment, the heavy chain constant region is an Fc chain. In yet another embodiment, the Fc chain is an IgG Fc fragment that comprises CH2 and CH3 domains. In yet another embodiment, the IgG Fc fragment is of the IgG1 subtype. The Fc chain may be a known or "wild type" Fc chain, or may be mutated. Non-limiting, illustrative, exemplary types of mutations are described in US Patent Application No. 20060034852, hereby incorporated by reference as if fully set forth herein.

The term "Fc chain" as used herein should be understood to encompass any type of Fc fragment. Several of the specific amino acid residues that are important for antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific modifications may result e.g. in glycosylation and/or other desired modifications to the Fc chain. It is envisaged that modifications may be made to e.g. block a function of Fc which is considered to be undesirable, such as an undesirable immune system effect.

Non-limiting, illustrative examples of mutations to Fc which may be made to modulate the activity of the fusion protein include the following changes (given with regard to the Fc sequence nomenclature as given by Kabat, from Kabat E A et al: *Sequences of Proteins of Immunological Interest*. US Department of Health and Human Services, NIH, 1991): 220C->S; 233-238 ELLGGP->EAEGAP; 265D->A, preferably in combination with 434N->A; 297N->A (for example to block N-glycosylation); 318-322 EYKCK->AYACA; 330-331AP->SS; or a combination thereof (see for example M Clark, "*Chemical Immunol and Antibody Engineering*", pp 1-31 for a description of these mutations and their effect). The construct for the Fc chain which features the above changes optionally comprises a combination of the hinge region with the CH2 and CH3 domains.

The above mutations may optionally be implemented to enhance desired properties or alternatively to block non-desired properties. For example, aglycosylation of antibodies was shown to maintain the desired binding functionality while blocking depletion of T-cells or triggering cytokine release, which may optionally be undesired functions (see M Clark, "*Chemical Immunol and Antibody Engineering*", pp 1-31). Substitution of 331proline for serine may block the ability to activate complement, which may optionally be considered an undesired function (see M Clark, "*Chemical Immunol and Antibody Engineering*", pp 1-31). Changing 330alanine to serine in combination with this change may also enhance the desired effect of blocking the ability to activate complement.

Residues 235 and 237 were shown to be involved in antibody-dependent cell-mediated cytotoxicity (ADCC), such that changing the block of residues from 233-238 as described may also block such activity if ADCC is considered to be an undesirable function.

Residue 220 is normally a cysteine for Fc from IgG1, which is the site at which the heavy chain forms a covalent linkage with the light chain. Optionally, this residue may be changed to a serine, to avoid any type of covalent linkage (see M Clark, "*Chemical Immunol and Antibody Engineering*", pp 1-31).

The above changes to residues 265 and 434 may optionally be implemented to reduce or block binding to the Fc receptor, which may optionally block undesired functionality of Fc related to its immune system functions (see "*Binding site on Human IgG1 for Fc Receptors*", Shields et al. vol 276, pp 6591-6604, 2001).

The above changes are intended as illustrations only of optional changes and are not meant to be limiting in any way. Furthermore, the above explanation is provided for descriptive purposes only, without wishing to be bound by a single hypothesis.

Thus, conjugates according to at least some embodiments of the present invention (which comprise a peptide according to at least some embodiments of the present invention) may comprise an antigen-recognizing immunoglobulin fragment and/or Fc chain. Such immunoglobulin fragments may comprise, for example, the Fab', F (ab') 2, Fv or Fab fragments, or other antigen-recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing such immunoglobulin fragments are well-known to those skilled in the art. See Parham, *J. Immunology*, 131, 2895, 1983; Lamoyi et al., *J. Immunological Methods*, 56, 235, 1983.

In at least some embodiments, the subject invention thus provides a conjugate/fusion protein comprising a peptide according to at least some embodiments of the present invention as depicted in any one of SEQ ID NOs: 1-22 and 48-186.

In at least some embodiments, the subject invention provides a conjugate/fusion protein according to at least some embodiments of the present invention for use in therapy. In at least some embodiments, the subject invention also provides a use of a conjugate/fusion protein according to at least some embodiments of the present invention for the manufacture of a medicament. In at least some embodiments, the subject invention further provides a pharmaceutical composition comprising a conjugate or fusion protein according to at least some embodiments of the present invention.

In at least some embodiments, the subject invention further provides a method of treating conditions, disorders and diseases where treatment or prevention of undesired angiogenesis can be of therapeutic value, comprising administering a pharmaceutically effective amount of a conjugate or fusion protein according to at least some embodiments of the present invention or a pharmaceutical composition comprising such conjugate or fusion protein to a subject in need thereof.

In at least some embodiments, the subject invention further provides a method of treating conditions, disorders and diseases, selected from but not limited to cancer, respiratory diseases, metabolic disorders, fibrotic and connective tissue related conditions, urogenital disorders, ocular diseases, vascular anomalies, cardiovascular diseases and their complications, inflammatory conditions associated with an infection or inflammatory disorders, chronic inflammatory and autoimmune diseases, bone disease or bone-related disorder and pain, comprising administering a pharmaceutically effective amount of a conjugate or fusion protein according to at least some embodiments of the present invention or a pharmaceutical composition comprising such conjugate or fusion protein to a subject in need thereof.

The following abbreviations should be understood as follows:

Amino Acid Abbreviation IUPAC Symbol:

A=Ala=Alanine
C=Cys=Cysteine
D=Asp=Aspartic Acid
E=Glu=Glutamic Acid
F=Phe=PhenylAlanine
G=Gly=Glycine
H=His=Histidine
I=Ile=Isoleucine
L=Lys=Lysine
M=Met=Methionine
N=Asn=Asparagine
P=Pro=Proline
Q=Gln=Glutamine
R=Arg=Arginine
S=Ser=Serine
T=Thr=Threonine
V=Val=Valine
W=Trp=Tryptophan
Y=Tyr=Tyrosine The following abbreviations shall be employed for nucleotide bases: A for adenine; G for guanine; T for thymine; U for uracil; and C for cytosine.

The invention is further described in the following examples, which are not in any way intended to limit the scope of the present invention as claimed.

EXAMPLES

Example 1

Synthesis of Peptides According to at Least Some Embodiments of the Present Invention The peptides were synthesized by solid-phase peptide synthesis using Fmoc-chemistry at Pepscan Systems (http://www.pepscan.nl). The peptides were amidated at their C-terminus, and acetylated at their N-terminus. CGEN-H2 (SEQ ID NO: 1) has a molecular weight of 3628.3, CGEN-H3 (SEQ ID NO: 2) has a molecular weight of 1313.6, CGEN-A8 (SEQ ID NO: 3) has a molecular weight of 1268.4, CGEN-H7 (SEQ ID NO: 4) has a molecular weight of 3052.7, CGEN-G4 (SEQ ID NO: 5) has a molecular weight of 1882.3, CGEN-G6 (SEQ ID NO: 6) has a molecular weight of 2356.8, CGEN-F9 (SEQ ID NO: 7) has a molecular weight of 4006.8, CGEN-F12 (SEQ ID NO: 8) has a molecular weight of 2694.3, CGEN-C6 (SEQ ID NO: 9) has a molecular weight of 2124.5, CGEN-A11 (SEQ ID NO: 10) has a molecular weight of 1464.7, and CGEN-G2 (SEQ ID NO: 11) has a molecular weight of 3506.2

1. CGEN-H2 [SEQ ID NO: 1] LKEEKENLQGLVTRQTYIQELEKQLNRAT
2. CGEN-H3 [SEQ ID NO: 2] TNNSVLQKQQL
3. CGEN-A8 [SEQ ID NO: 3] LMDTVHNLVNL
4. CGEN-H7 [SEQ ID NO: 4] NEILKIHEKNSLLEHKILEMEGKHK
5. CGEN-G4 [SEQ ID NO: 5] QLQVLVSKQNSIIEEL
6. CGEN-G6 [SEQ ID NO: 6] DLMETVNNLLTMMSTSNSAKD

7. CGEN-F9 [SEQ ID NO: 7] QEELASILSKKAK-LLNTLSRQSAALTNIERGLRGVR
8. CGEN-F12 [SEQ ID NO: 8] QHSLRQLLVLL-RHLVQERANASA
9. CGEN-C6 [SEQ ID NO: 9] TDMEAQLLNQTSRM-DAQM
10. CGEN-A11 [SEQ ID NO: 10] ETFLSTNKLENQ
11. CGEN-G2 [SEQ ID NO: 11] TQQVKQLEQALQNNT-QWLKKLERAIKTIL

Example 2

Analysis of Activity of Peptides According to at Least Some Embodiments of the Present Invention on Angiogenesis In Vitro CGEN-H2 (SEQ ID NO: 1), CGEN-H3 (SEQ ID NO: 2), CGEN-A8 (SEQ ID NO: 3), CGEN-H7 (SEQ ID NO: 4), CGEN-G4 (SEQ ID NO: 5), CGEN-G6 (SEQ ID NO: 6), CGEN-F9 (SEQ ID NO: 7), CGEN-F12 (SEQ ID NO: 8), CGEN-C6 (SEQ ID NO: 9), CGEN-A11 (SEQ ID NO: 10), and CGEN-G2 (SEQ ID NO: 11) as synthesized in Example 1, were analyzed for their ability to affect angiogenesis in vitro in a human multicellular model (AngioKit, TCS Cell-Works, UK). This model reproduces the different phases of the angiogenesis process using a co-culture of human endothelial cells with other human cell types in specially developed medium (Bishop E. T. et al, 1999 Angiogenesis 3(4):335). Briefly, 24 well plates were seeded with cells on day 0 and medium was changed on days 3, 4, 7, 10 and 12 in accordance with the standard AngioKit procedure. Test and control compounds at the appropriate dilutions were included in the medium changes on days 4, 7, 10 and 12. CGEN-H2 (SEQ ID NO: 1), CGEN-H3 (SEQ ID NO: 2), CGEN-A8 (SEQ ID NO: 3), CGEN-H7 (SEQ ID NO: 4), CGEN-F9 (SEQ ID NO: 7), CGEN-F12 (SEQ ID NO: 8), CGEN-A11 (SEQ ID NO: 10), and CGEN-G2 (SEQ ID NO: 11) were dissolved in 20% DMSO and CGEN-G4 (SEQ ID NO: 5), CGEN-G6 (SEQ ID NO: 6), and CGEN-C6 (SEQ ID NO: 9) were dissolved in 1% NH$_4$HCO$_3$ to a stock concentration of 1 mg/ml. All test samples were diluted in medium to their final concentration on the day that they were added to the appropriate wells. Peptides were assayed at two concentrations (1 and 20 µg/mL) in duplicates. The following control treatments were included: "untreated" optimized growth medium, suramin (20 µM) as anti-angiogenic control, Tie-2 neutralizing antibody (R&D Systems, Cat# AF313, 5 µg/ml) as anti-angiogenic inhibitor of the Ang/Tie2 pathway, VEGF (2 ng/mL) as pro-angiogenic control, and treatments of the appropriate buffers; DMSO or NH$_4$HCO$_3$, as vehicle controls. All Angio-Kits were then fixed and stained on day 14, using the CD31 Staining Kits according to the standard AngioKit procedure. Comparison of tubule development was conducted using the "AngioSys" (TCS Cellworks, UK) image analysis system developed specifically for the analysis of images produced using the AngioKit. Four images taken from predetermined positions within each well were recorded. Each concentration of test compound therefore yielded 4 images for analysis in duplicate.

FIG. 1 demonstrates the effect of CGEN-H2 (SEQ ID NO: 1), CGEN-H3 (SEQ ID NO: 2), CGEN-A8 (SEQ ID NO: 3), CGEN-H7 (SEQ ID NO: 4), CGEN-G4 (SEQ ID NO: 5), CGEN-G6 (SEQ ID NO: 6), CGEN-F9 (SEQ ID NO: 7), CGEN-F12 (SEQ ID NO: 8), CGEN-C6 (SEQ ID NO: 9), CGEN-A11 (SEQ ID NO: 10), and CGEN-G2 (SEQ ID NO: 11) on in vitro angiogenesis. CGEN-H2 (SEQ ID NO: 1), CGEN-H3 (SEQ ID NO: 2), CGEN-A8 (SEQ ID NO: 3), CGEN-H7 (SEQ ID NO: 4), CGEN-G4 (SEQ ID NO: 5), CGEN-G6 (SEQ ID NO: 6), CGEN-F9 (SEQ ID NO: 7), CGEN-F12 (SEQ ID NO: 8), CGEN-C6 (SEQ ID NO: 9), CGEN-A11 (SEQ ID NO: 10), and CGEN-G2 (SEQ ID NO: 11) were added at 1 or 20 µg/mL to a commercial co-culture (Angiokit) of early passage human endothelial cells with early passage human interstitial cells and the total tubule length was measured after 14 days. The results, shown in FIG. 1, are given as total tubule length relative to the untreated growth medium, defined as 100%. As shown in FIG. 1, CGEN-H2 (SEQ ID NO: 1), CGEN-H3 (SEQ ID NO: 2), CGEN-A8 (SEQ ID NO: 3), CGEN-H7 (SEQ ID NO: 4), CGEN-G4 (SEQ ID NO: 5), CGEN-G6 (SEQ ID NO: 6), CGEN-F9 (SEQ ID NO: 7), CGEN-F12 (SEQ ID NO: 8), CGEN-C6 (SEQ ID NO: 9), CGEN-A11 (SEQ ID NO: 10), and CGEN-G2 (SEQ ID NO: 11) reduced total tubule length by 15-36%. VEGF induced tubule length by 130%, wheras the Tie-2 neutralizing antibody control and the positive anti-angiogenic control, suramin, reduced the tubule length by 32% and 50%, respectively (data not shown).

Example 3

Orthologs

Figure 2A:
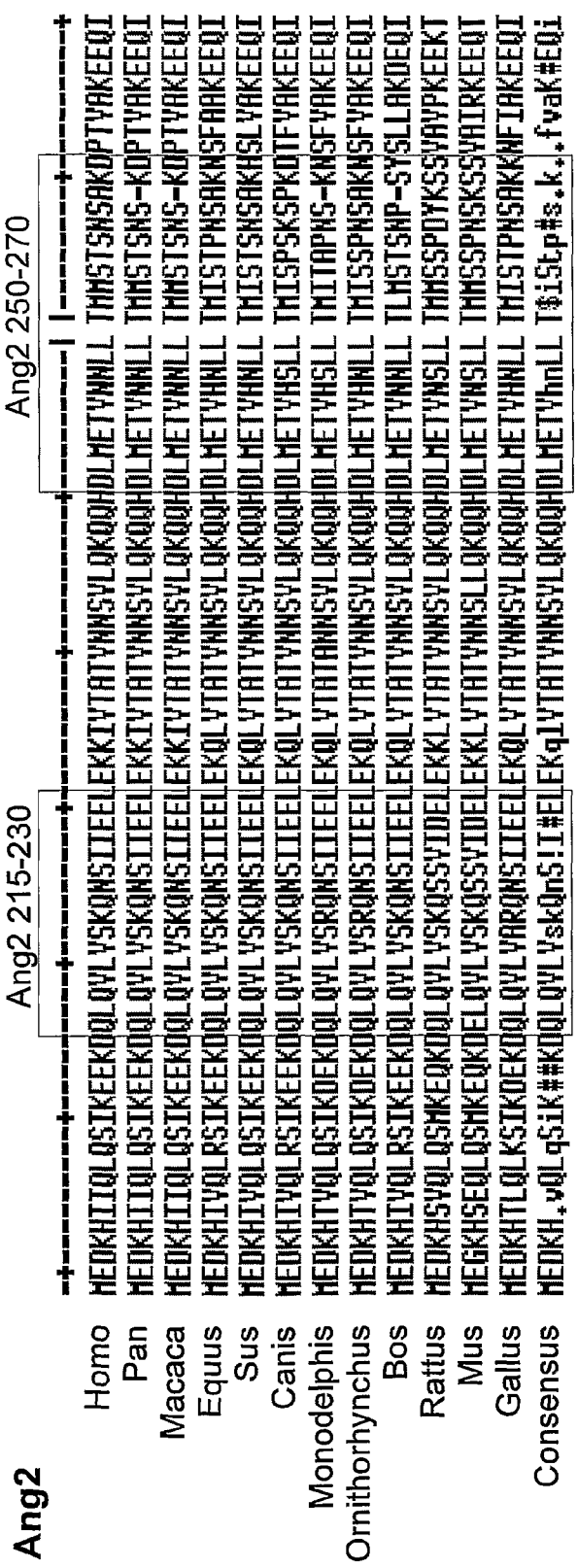
FIG. 2A shows a multiple alignment comparison of the sequence of CGEN-G4 (SEQ ID NO: 5), CGEN-G6 (SEQ ID NO: 6), corresponding to amino acid residues 215-230 and 250-270, respectively, of the human angiopoietin 2 protein sequence (SEQ ID NO: 46), and homologous sequences derived from Macaca mulatta (gi|109085520), Equus caballus (gi|149742724), Sus scrofa (gi|47523224), Bos Taurus (gi|157426837), Mus musculus (gi|31982508), Rattus norvegicus (gi|109503530), Canis lupus familiaris (gi|114326363), Monodelphis domestica (gi|126303279), Gallus gallus (gi|10120280), Ornithorhynchus anatinus (gi|149412433), Pan troglodytes (gi|114618691).
Figure 2B:
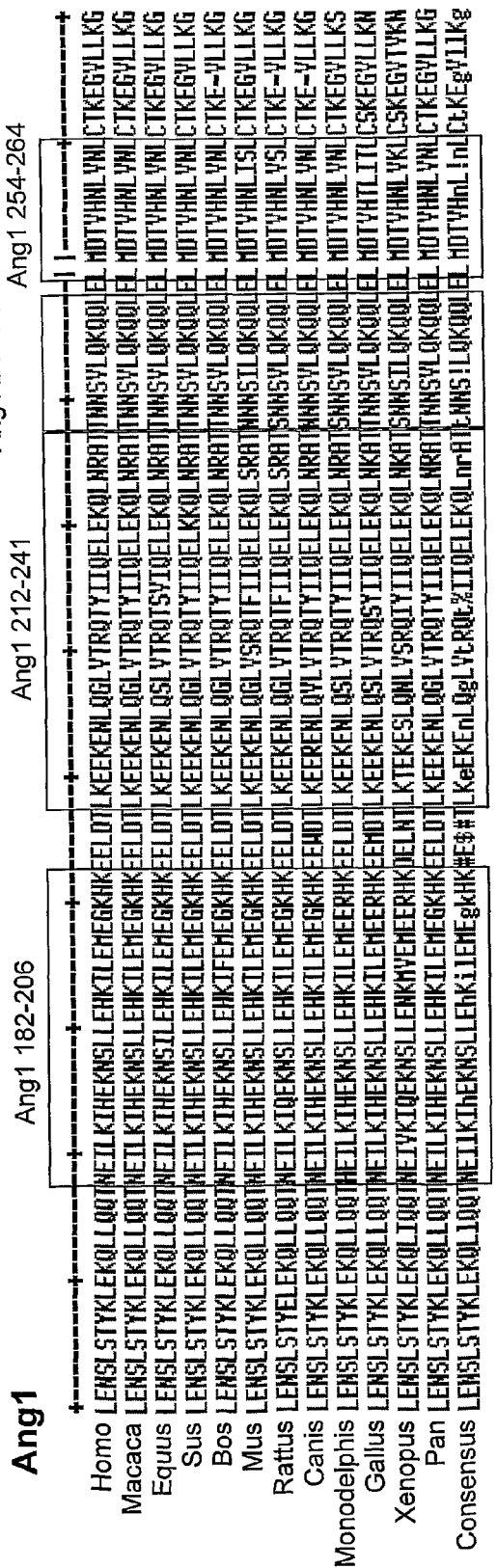
FIG. 2B shows a multiple alignment comparison of the sequence of CGEN-H2 (SEQ ID NO: 1), CGEN-H3 (SEQ ID NO: 2), CGEN-A8 (SEQ ID NO: 3), CGEN-H7 (SEQ ID NO: 4) corresponding to amino acid residues 212-241, 242-252, 254-264, 182-206, respectively, in the human angiopoietin 1 protein (SEQ ID NO: 45), and homologous sequences derived from Macaca mulatta (gi|109087219), Equus caballus (gi|149721604), Sus scrofa (gi|47522748), Bos Taurus (gi|116003815), Mus musculus (gi|46048213), Rattus norvegicus (gi|123308739), Canis lupus familiaris (gi|54262113), Monodelphis domestica (gi|126322207), Gallus gallus (gi|118087303), Xenopus laevis (gi|148238152), Pan troglodytes (gi|114621310).

The sequence of the CGEN-H2 (SEQ ID NO: 1), CGEN-H3 (SEQ ID NO: 2), CGEN-A8 (SEQ ID NO: 3), CGEN-H7 (SEQ ID NO: 4) corresponding to amino acid residues 212-241, 242-252, 254-264, 182-206, respectively, in the human angiopoietin 1 protein (SEQ ID NO: 45) is highly conserved throughout other species and orthologs, as can be seen from FIG. 2B.

FIG. 2B shows a multiple alignment comparison of the sequence of CGEN-H2 (SEQ ID NO: 1), CGEN-H3 (SEQ ID NO: 2), CGEN-A8 (SEQ ID NO: 3), CGEN-H7 (SEQ ID NO: 4) corresponding to amino acid residues 212-241, 242-252, 254-264, 182-206, respectively, in the human angiopoietin 1 protein (SEQ ID NO: 45), and homologous sequences derived from various organisms, including *Macaca mulatta* (gi|109087219), *Equus caballus* (gi|149721604), *Sus scrofa* (gi|47522748), *Bos Taurus* (gi|116003815), *Mus musculus* (gi|46048213), *Rattus norvegicus* (gi|23308739), *Canis lupus familiaris* (gi|54262113), *Monodelphis domestica* (gi|126322207), *Gallus gallus* (gi|118087303), *Xenopus laevis* (gi|148238152), *Pan troglodytes* (gi|114621310). The rectangles show the comparison blocks for the peptides. Positions of the peptides are identified according to human angiopoietin 1 protein (SEQ ID NO: 45). The sequences of orthologous peptides for CGEN-H2 (SEQ ID NO: 1), CGEN-H3 (SEQ ID NO: 2), CGEN-A8 (SEQ ID NO: 3), and CGEN-H7 (SEQ ID NO: 4) are provided in SEQ ID NO: 165-172, 161-164, 137-140, and 149-154, respectively.

The sequence of the CGEN-G4 (SEQ ID NO: 5), CGEN-G6 (SEQ ID NO: 6), corresponding to amino acid residues 215-230 and 250-270, respectively, of the angiopoietin 2 protein sequence (GenBank Accession number: gi|4557315, SEQ ID NO: 46) is highly conserved throughout other species and orthologs, as can be seen from FIG. 2A.

FIG. 2A shows a multiple alignment comparison of the sequence of CGEN-G4 (SEQ ID NO: 5), CGEN-G6 (SEQ ID NO: 6), corresponding to amino acid residues 215-230 and 250-270, respectively, of the human angiopoietin 2 protein sequence (SEQ ID NO: 46), and homologous sequences derived from various organisms, including *Macaca mulatta* (gi|109085520), *Equus caballus* (gi|149742724), *Sus scrofa* (gi|47523224), *Bos Taurus* (gi|157426837), *Mus musculus* (gi|31982508), *Rattus norvegicus* (gi|109503530), *Canis*

*lupus familiaris* (gi|114326363), *Monodelphis domestica* (gi|126303279), *Gallus gallus* (gi|10120280), *Ornithorhynchus anatinus* (gi|149412433), *Pan troglodytes* (gi|114618691).

The rectangles show the comparison blocks for the peptides. Positions of the peptides are identified according to human angiopoietin 2 protein (SEQ ID NO: 46). The sequences of orthologous peptides for CGEN-G4 (SEQ ID NO: 5), and CGEN-G6 (SEQ ID NO: 6) are provided in SEQ ID NO: 73-76, and 63-72, respectively.

Figure 2C:
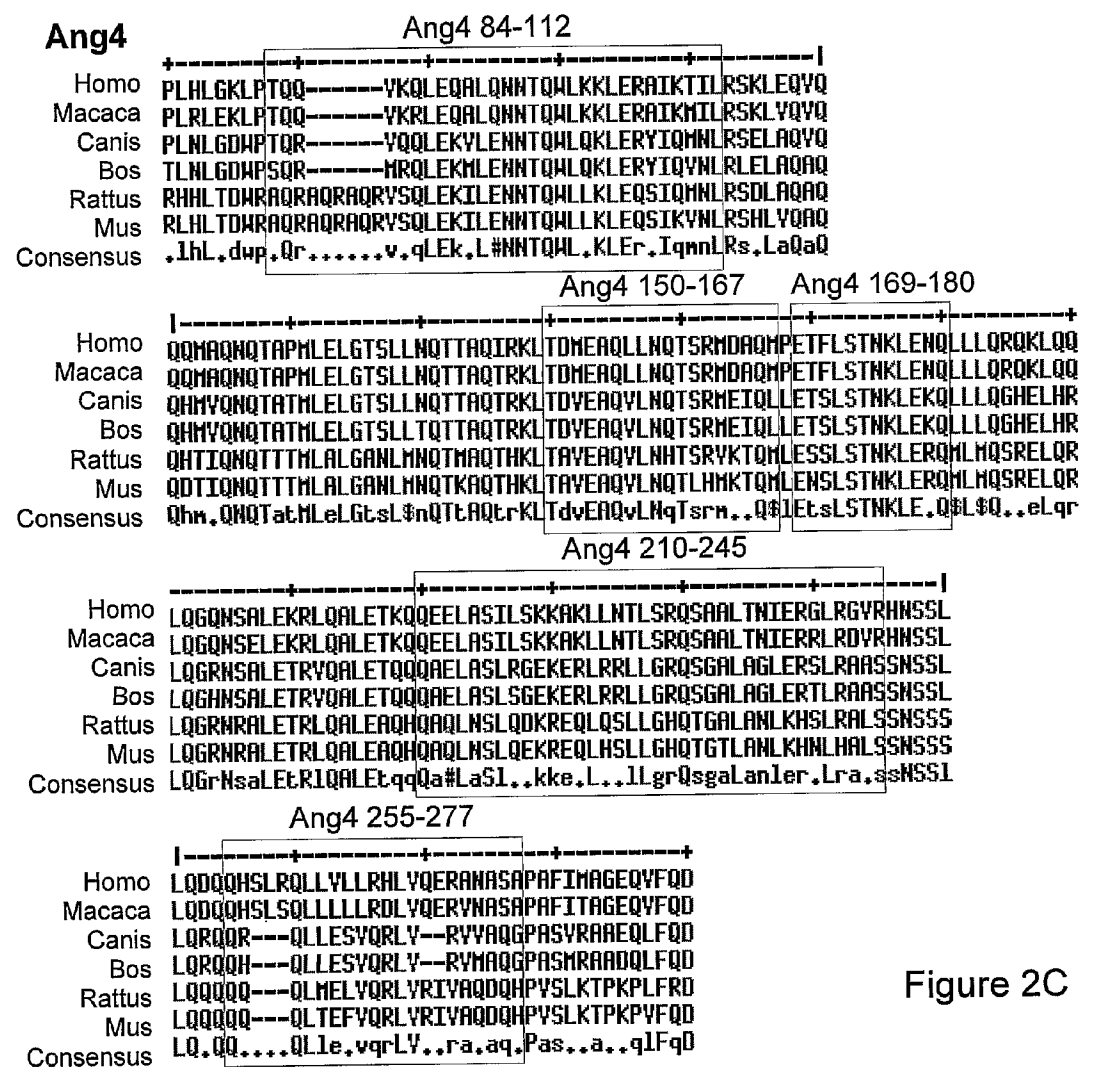

The sequence of the CGEN-F9 (SEQ ID NO: 7), CGEN-F12 (SEQ ID NO: 8), CGEN-C6 (SEQ ID NO: 9), CGEN-A11 (SEQ ID NO: 10), CGEN-G2 (SEQ ID NO: 11) corresponding to amino acid residues 210-245, 255-277, 150-167, 169-180, 84-112 of the angiopoietin 4 protein sequence (GenBank Accession number: gi|7705276, SEQ ID NO: 47) is highly conserved throughout other species and orthologs, as can be seen from FIG. 2C.

FIG. 2C shows a multiple alignment comparison of the sequence of CGEN-F9 (SEQ ID NO: 7), CGEN-F12 (SEQ ID NO: 8), CGEN-C6 (SEQ ID NO: 9), CGEN-A11 (SEQ ID NO: 10), CGEN-G2 (SEQ ID NO: 11) corresponding to amino acid residues 210-245, 255-277, 150-167, 169-180, 84-112 of the angiopoietin 4 protein sequence (GenBank Accession number: gi|7705276, SEQ ID NO: 47), and homologous sequences derived from various organisms, including *Macaca mulatta* (gi|109092550), *Bos Taurus* (gi|115497116), *Mus musculus* (gi|6753006), *Rattus norvegicus* (gi|157820699), *Canis lupus familiaris* (gi|73992066).

The rectangles show the comparison blocks for the peptides. Positions of the peptides are identified according to human angiopoietin 4 protein (SEQ ID NO: 47). The sequences of orthologous peptides for CGEN-F9 (SEQ ID NO: 7), CGEN-F12 (SEQ ID NO: 8), CGEN-C6 (SEQ ID NO: 9), CGEN-A11 (SEQ ID NO: 10), and CGEN-G2 (SEQ ID NO: 11) are provided in SEQ ID NO: 98-102, 106-110, 116-119, 134-136, and 124-128, respectively.

Example 4

Design of Conformational Change Blockers of Angiopoietins

Conformational changes in proteins play a major role in activity regulation. Natural and synthetic molecules that modulate such changes are of considerable biological importance. Such molecules include allosteric effectors that alter the rapidity of enzyme-catalyzed reactions (J. Monod, et al., *J Mol Biol* 12, 88 (1965)), molecules that shift the oligomerization equilibrium of proteins (Z Hayouka et al., *Proc Natl Acad Sci USA* 104, 8316 (2007)), and molecules that interfere with transmembrane helix-helix associations (H Yin et al., *Science* 315, 1817 (2007)).

Conformational change modulators of Angiopoietins were designed. The designed peptides were identified using a unique computerized method to interfere with conformational changes involving helix-helix interactions.

Figure 3A:
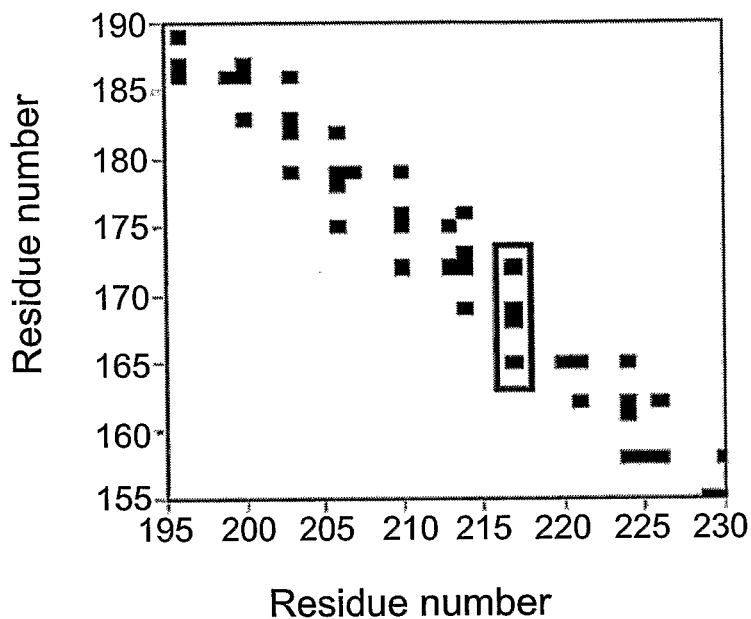
FIG. 3A demonstrates an example for a known protein (BAG-1, Protein Data Bank ID 1hx1 (chain B)) that comprises two helices that interact with each other in an anti-parallel manner.

A computational approach for sequence-based identification of intra-molecular helix-helix interactions was able to detect interactions that ordinarily difficult to observe experimentally. The computational approach was based on the analysis of correlated mutations in the sequences of a target protein and its homologs (FIG. 3*and* FIG. 4).

Such analysis aims at identifying intra-molecular interactions between pairs of amino acid residues (S. S. Choi, et al., *Nat Genet.* 37, 1367 (2005); G. B. Gloor, et al., *Biochemistry* 44, 7156 (2005); U Gobel, et al., *Proteins* 18, 309 (1994); S. W. Lockless, et al., *Science* 286, 295 (1999); L. C. Martin, et al., *Bioinformatics* 21, 4116 (2005); F. Pazos, et al., *Comput Appl Biosci* 13, 319 (1997)) facilitated by the introduction of a new category of residue-residue contact prediction into the Critical Assessment of techniques for protein Structure Prediction (CASP) competition (J. M Izarzugaza, et al., *Proteins* 69 *Suppl* 8, 152 (2007)). Nevertheless, despite these algorithmic advances and the growing availability of sequence data, the signal to noise ratio of correlated mutation analysis remains relatively low, and does not currently allow ab initio structure prediction.

Figure 3B:
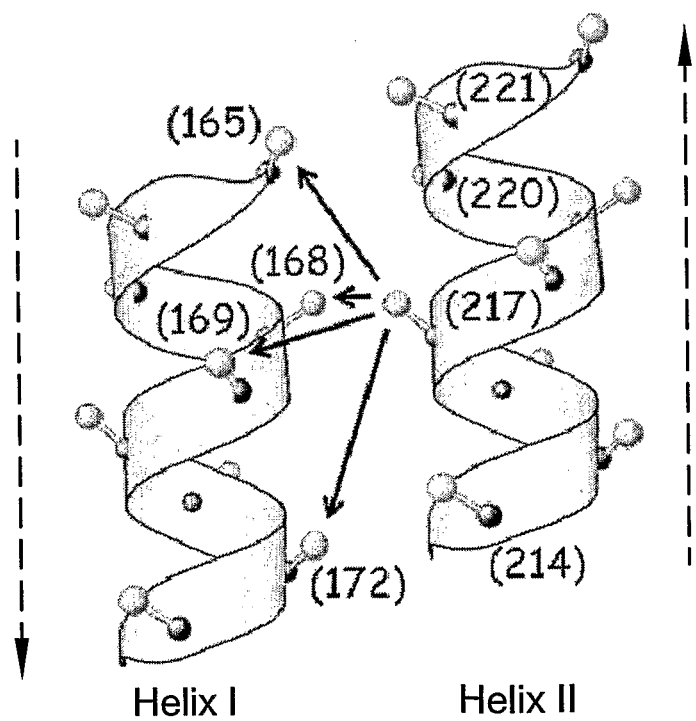
FIG. 3B demonstrates a schematic view of two helices interacting through their adjacent faces.
Figure 3C:
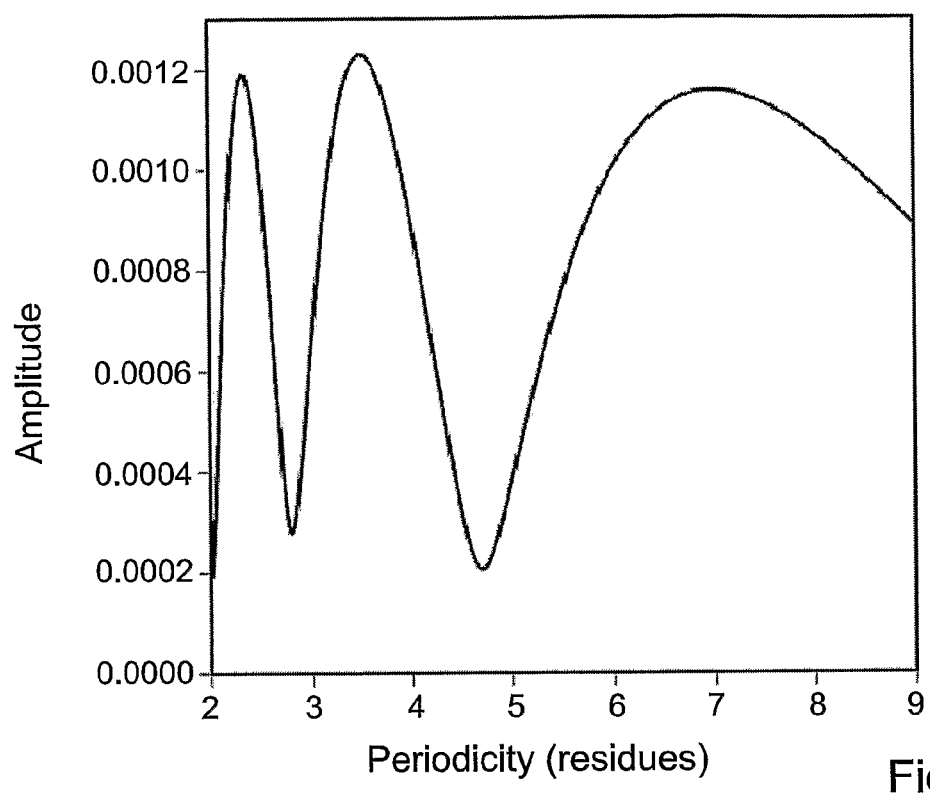
FIG. 3C shows a typical Fourier transform corresponding to the sum of columns in the 21 by 21 matrix (a submatrix of the protein's contact map) that represents the anti-parallel interaction.

The detection of interacting segments through correlated mutation analysis is hindered by the thus low signal to noise ratio, when applied naively, e.g., averaging over a sliding window approach. The conceptual new ingredient of the unique in silico approach used herein for identification of peptides capable of acting as conformational change blockers of Angiopoietins, was the exploitation of the periodic nature of the correlated mutation data for helix-helix interactions, for which the corresponding periodicity should be around 3.6 amino acids (FIGS. 3A-B). Technically, this was achieved using an appropriate application of the Fourier transform. An interaction in Ang4 was detected by a peak in the absolute value of the Fourier transform of the correlated mutations signal around the typical periodicity (FIG. 3C). Although the transform is one dimensional, it analyses the two dimensional matrix of correlated mutation scores, detecting the periodicity manifested in both interacting segments (FIG. 4). In this unique technology, used for computerized detection of peptides capable of acting as conformational change blockers of Angiopoietins, Fourier transform was introduced to correlated mutations analysis, substantially improving the signal to noise ratio, as well as a "two dimensional" Fourier analysis was employed in protein structure determination.

This newly-developed tool was applied to Ang1, Ang2, and Ang4, and resulted in detection of remarkable peaks of the absolute values of the Fourier transform around the expected periodicity.

Using this approach, an interaction between CGEN-F9 (SEQ ID NO:7) and a helix peptide corresponding to SEQ ID NO:58-59 in Ang 4 (partner helix) was computationally identified.

FIG. 3 shows the identification using the unique computerized method for prediction of helix-helix interactions. FIG. 3A demonstrates an example of residue-residue contact map of two anti-parallel helices taken from the solved structure of BAG-1 (PDB id: 1HX1 Chain B) calculated using CSU (V. Sobolev, A. Sorokine, J. Prilusky, E. E. Abola, M. Edelman, *Bioinformatics* 15, 327 (1999)). FIG. 3B demonstrates a schematic view of two helices interacting through their adjacent faces. This interaction gives rise to the 3.6-residue periodicity that is the basis of our Fourier transform-based approach. Each residue on one helix may interact with 3-4 residues on the other helix spanning a region of 8-9 residues (see rectangle in FIG. 3A). The residue-residue contact map for Ang 4 was predicted by SVMcon (J. Cheng, et al., *BMC Bioinformatics* 8, 113 (2007)). Typically, in these methods (S. S. Choi, *Nat Genet.* 37, 1367 (2005); G. B. Gloor, *Biochemistry* 44, 7156 (2005); U. Gobel, et al., *Proteins* 18, 309 (1994); L. C. Martin, et al., *Bioinformatics* 21, 4116 (2005); F. Pazos, et al., *Comput Appl Biosci* 13, 319 (1997); J. Cheng, et al., *BMC Bioinformatics* 8, 113 (2007); S. D. Dunn, et al., *Bioinformatics* 24, 333 (2008); G. Shackelford, et al., *Proteins* 69 *Suppl* 8, 159 (2007)) the sequences of the protein of interest and its homologs are used for constructing a multiple sequence alignment (MSA). Correlations between columns in the MSA (correlated mutations) point to predicted residue-residue interactions. Until today however, known contact map prediction technologies suffered from low recall and low precision. These drawbacks in helix-helix interactions identification have now been solved by the unique in silico approach used herein for identification of peptides capable of acting as conformational change blockers of Angiopoietins. FIG. 4 shows a map of scores based on the Fourier transform of the correlated mutation signal of Ang 4. In order to detect helix-helix interactions, for each pair of 21-residue long segments two vectors of sums of the predicted residue-residue scores were calculated: one for the rows and one for the columns of the corresponding 21 by 21 matrix. For the detection of parallel helix-helix interactions only the principal (i.e. major) diagonal and its 4 neighboring diagonals from each side were summed. For anti-parallel interactions, the minor diagonal was similarly utilized. The two vectors are then Fourier transformed. A joint score was calculated that is non-zero only if a significant peak representing a periodicity of about 3.6 residues exists in the Fourier Transform of both the 'rows' and the 'column' vectors.

Figure 4:
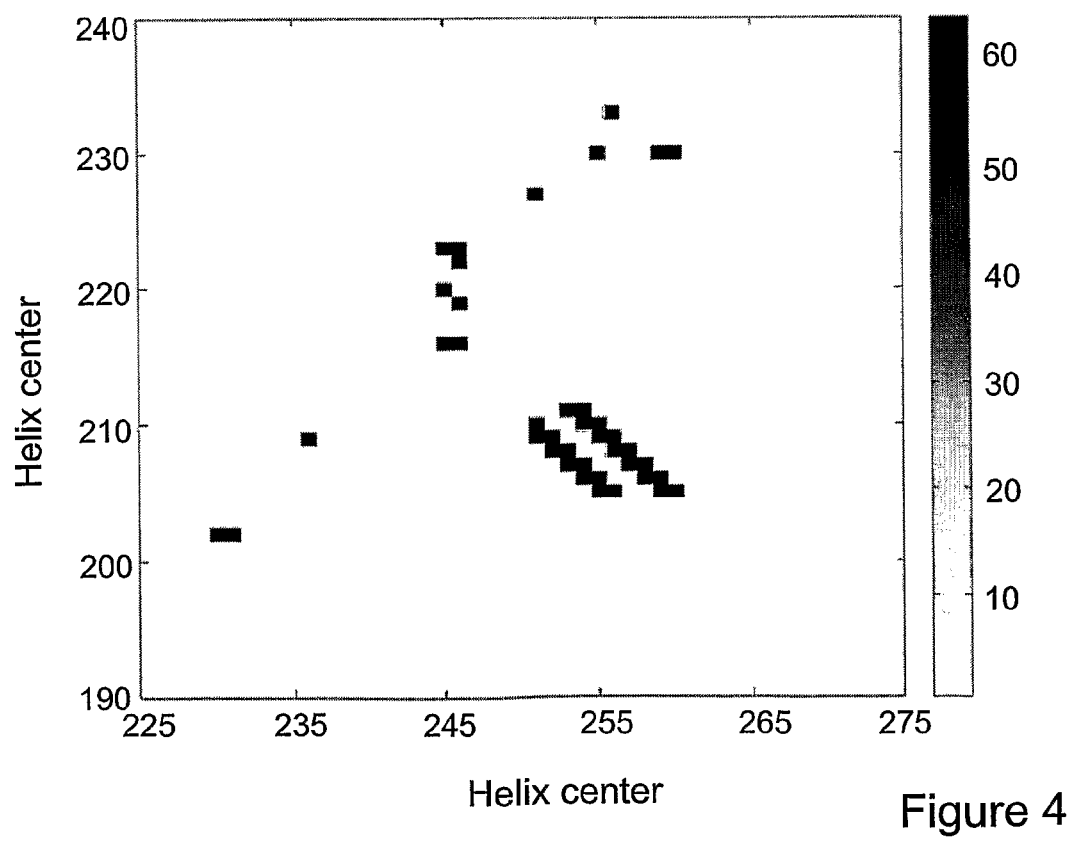
FIG. 4 shows a map of scores based on the Fourier transform of the predicted contact map of Ang4. The residue-residue contact map for Ang4 was calculated using SVMcon (J. Cheng, P. Baldi, BMC Bioinformatics 8, 113 (2007).

FIG. 4 presents In Silico detection of a helix-helix interaction in Ang 4.

Similar to the way the intra-molecular helix-helix that involves CGEN-F9 (SEQ ID NO:7) was detected, the computational analysis revealed other intra-molecular helix-helix interaction in Ang1, Ang2, and Ang4. The results are the peptides corresponding to SEQ ID NO:1-11 and their partner helix described as SEQ ID NO:48-62.

Example 5

Binding Analysis of Peptides According to at Least Some Embodiments of The Present Invention to Recombinant Ang1, Ang2, and Ang4

The capability of CGEN-H2 [SEQ ID NO: 1], CGEN-H3 [SEQ ID NO: 2], CGEN-A8 [SEQ ID NO: 3], CGEN-H7 [SEQ ID NO: 4], CGEN-G4 [SEQ ID NO: 5], CGEN-G6 [SEQ ID NO: 6], CGEN-F9 [SEQ ID NO: 7], CGEN-F12 [SEQ ID NO: 8], CGEN-C6 [SEQ ID NO: 9], CGEN-A11 [SEQ ID NO: 10], and CGEN-G2 [SEQ ID NO: 11] to specifically bind to recombinant Ang1, Ang2, and Ang4 was investigated using the BIACORE technology, measuring protein-protein interaction and binding affinity (Wendler et al 2005, *Anal Bioanal Chem*, 381: 1056-4064). The technology is based on surface plasmon resonance (SPR), an optical phenomenon that enables detection of unlabeled interactants in real time. The SPR-based biosensors can be used in determination of active concentration, screening and characterization in terms of both affinity and kinetics.

Peptide-protein binding was analyzed using surface plasmon resonance. Analysis of the to interaction between CGEN-H2 [SEQ ID NO: 1], CGEN-H3 [SEQ ID NO: 2], CGEN-A8 [SEQ ID NO: 3], CGEN-H7 [SEQ ID NO: 4], CGEN-G4 [SEQ ID NO: 5], CGEN-G6 [SEQ ID NO: 6], CGEN-F9 [SEQ ID NO: 7], CGEN-F12 [SEQ ID NO: 8], CGEN-C6 [SEQ ID NO: 9], CGEN-A11 [SEQ ID NO: 10], and CGEN-G2 [SEQ ID NO: 11] peptides and recombinant human Ang1 carrier-free (R&D Systems, Cat# 923-AN-025/CF, Lot# FHW1507031), human Ang2 carrier-free (R&D Systems, Cat# 623-AN-025/CF, Lot# BNO0457121), and human Ang4 carrier-free (R&D Systems, Cat# 964-AN-025/CF, Lot# ELM025121) was conducted using the BIAcore biosensor (Pharmacia Biosensor, Uppsala, Sweden). The recombinant Ang1, Ang2, and Ang4 were immobilized directly to a CM5 sensor chip. Solutions containing 10-50 µM of CGEN-H2 [SEQ ID NO: 1], CGEN-H3 [SEQ ID NO: 2], CGEN-A8 [SEQ ID NO: 3], CGEN-H7 [SEQ ID NO: 4], CGEN-G4 [SEQ ID NO: 5], CGEN-G6 [SEQ ID NO: 6], CGEN-F9 [SEQ ID NO: 7], CGEN-F12 [SEQ ID NO: 8], CGEN-C6 [SEQ ID NO: 9], CGEN-A11 [SEQ ID NO: 10], and CGEN-G2 [SEQ ID NO: 11] peptides were injected into the sample chamber of the BIACORE device at a rate of 20 µl/min and the interaction was monitored using surface plasmon resonance. Peptides CGEN-H2 [SEQ ID NO: 1], CGEN-H3 [SEQ ID NO: 2], CGEN-A8 [SEQ ID NO: 3], CGEN-H7 [SEQ ID NO: 4], and CGEN-G4 [SEQ ID NO: 5] showed none or low binding to the chip, possibly due to technical problems. CGEN-C6 [SEQ ID NO: 9] did not bind Ang1 and Ang4. Binding of CGEN-C6 to Ang2 was not sufficiently strong and too noisy for kinetic measurements or determination of affinity constant.

Peptides CGEN-G6 [SEQ ID NO: 6], CGEN-F9 [SEQ ID NO: 7], CGEN-F12 [SEQ ID NO: 8], CGEN-A11 [SEQ ID NO: 10], and CGEN-G2 [SEQ ID NO: 11] were capable of binding to immobilized Ang1, Ang2, and Ang4 on the chip and were further analyzed for binding kinetics, as follows. Solutions containing different concentrations of CGEN-G6 [SEQ ID NO: 6], CGEN-F9 [SEQ ID NO: 7], CGEN-F12 [SEQ ID NO: 8], CGEN-A11 [SEQ ID NO: 10], and CGEN-G2 [SEQ ID NO: 11] peptides (as indicated in Table 2) were injected into the sample chamber of the BIACORE device at a rate of 30 µl/min and the interaction was monitored using surface plasmon resonance. As a background, the solutions were also injected onto an empty flow cell with no immobilized ligand and the binding levels achieved were subtracted. Data was analyzed using BIAevaluation software. The affinity constant of the interaction between CGEN-G6 [SEQ ID NO: 6], CGEN-F9 [SEQ ID NO: 7], CGEN-F12 [SEQ ID NO: 8], CGEN-C6 [SEQ ID NO: 9], CGEN-A11 [SEQ ID NO: 10], and CGEN-G2 [SEQ ID NO: 11] and Ang1, Ang2, or Ang4 was determined by direct kinetic analysis. The 1:1 Langmuir binding model was used to fit kinetic data.

Table 2 summarizes results of analysis of CGEN-G6 [SEQ ID NO: 6], CGEN-F9 [SEQ ID NO: 7], CGEN-F12 [SEQ ID NO: 8], CGEN-A11 [SEQ ID NO: 10], and CGEN-G2 [SEQ ID NO: 11] interaction with Ang1, Ang2, or Ang4. Kinetic measurements were done at the indicated concentration range, and they are presented as $K_D$(M). CGEN-F12 [SEQ ID NO: 8] bound to Ang1 and Ang4 with high affinity. The specificity of this binding is not clear.

TABLE 2

| Peptide | Conc. (µM) range | Ang1 | Ang2 | Ang4 |
| --- | --- | --- | --- | --- |
| CGEN-F12 | 0.625-0.039 | $1.88 \times 10^{-9}$ | $5.84 \times 10^{-6}$ | $2.43 \times 10^{-10}$ |
| CGEN-G6 | 1.25-0.039 | $1.33 \times 10^{-8}$ | ND | $2.21 \times 10^{-8}$ |
| CGEN-F9 | 25-1.56 | $2.14 \times 10^{-5}$ | $3.07 \times 10^{-6}$ | $2.82 \times 10^{-6}$ |
| CGEN-A11 | 25-1.56 | $6.74 \times 10^{-6}$ | $2.36 \times 10^{-6}$ | $3.69 \times 10^{-6}$ |
| CGEN-G2 | 0.625-0.039 | $1.74 \times 10^{-8}$ | $5.66 \times 10^{-8}$ | $2.5 \times 10^{-8}$ |

Example 6

Binding Analysis of Peptides According to at Least Some Embodiments of The Present Invention to Recombinant Tie2 and Competition with Ligand Binding to Tie-2

The capability of CGEN-G6 [SEQ ID NO: 6], CGEN-F9 [SEQ ID NO: 7], CGEN-C6 [SEQ ID NO: 9], CGEN-A11 [SEQ ID NO: 10], and CGEN-G2 [SEQ ID NO: 11] to specifically bind to recombinant Tie2 and interfere with the binding of Ang1, Ang2, or Ang4 to Tie2 was investigated using the BIACORE technology, measuring protein-protein interaction and binding affinity (Wendler et al 2005, *Anal Bioanal Chem*, 381: 1056-1064). The technology is based on surface plasmon resonance (SPR), an optical phenomenon that enables detection of unlabeled interactants in real time. The SPR-based biosensors can be used in determination of active concentration, screening and characterization in terms of both affinity and kinetics.

Peptide-protein interaction was analyzed using surface plasmon resonance. Analysis of the interaction between CGEN-G6 [SEQ ID NO: 6], CGEN-F9 [SEQ ID NO: 7], CGEN-C6 [SEQ ID NO: 9], CGEN-A11 [SEQ ID NO: 10], and CGEN-G2 [SEQ ID NO: 11] peptides and recombinant human Tie-2/Fc chimera (carrier-free, R&D Systems, Cat# 313-TI, Lot# BKC0707121) was conducted using the BIAcore biosensor (Pharmacia Biosensor, Uppsala, Sweden). The recombinant Tie-2/Fc chimera was immobilized directly to a CM5 sensor chip. Solutions containing 10-50 µM of CGEN-G6 [SEQ ID NO: 6], CGEN-F9 [SEQ ID NO: 7], CGEN-C6 [SEQ ID NO: 9], CGEN-A11 [SEQ ID NO: 10], and CGEN-G2 [SEQ ID NO: 11] were injected into the sample chamber of the BIACORE device at a rate of 20 µl/min and the interaction was monitored using surface plasmon resonance. In addition, solutions containing 100-500 nM of Ang1, Ang2, and Ang4 proteins were injected alone or in combination with 10-50 µM of CGEN-G6 [SEQ ID NO: 6], CGEN-F9 [SEQ ID NO: 7], CGEN-C6 [SEQ ID NO: 9], CGEN-A11 [SEQ ID NO: 10], and CGEN-G2 [SEQ ID NO: 11] peptides at a constant ratio of 1:100 (Ang ligand to peptide) into the sample chamber of the BIACORE device at a rate of 20 µl/min and the interaction was monitored using surface plasmon resonance. CGEN-02 [SEQ ID NO: 11] peptide showed some non specific binding and its capability to interfere with Ang ligand binding to Tie2 was not determined.

Figure 5A:
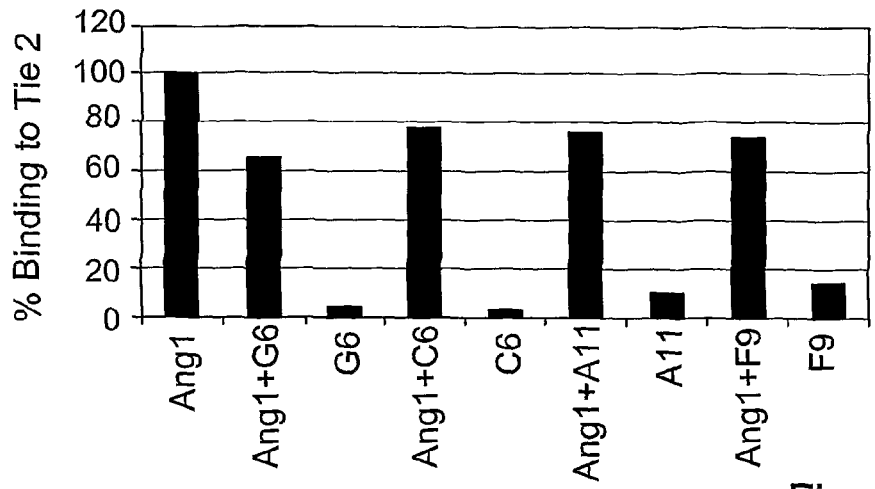
FIG. 5 demonstrates the capability of peptides CGEN-G6 (SEQ ID NO: 6), CGEN-F9 (SEQ ID NO: 7), CGEN-C6 (SEQ ID NO: 9), and CGEN-A11 (SEQ ID NO: 10) to interfere with the binding of Ang1 (FIG. 5A), Ang2 (FIG. 5B), or Ang4 (FIG. 5C) to Tie2 using the BIACORE technology.
Figure 5B:
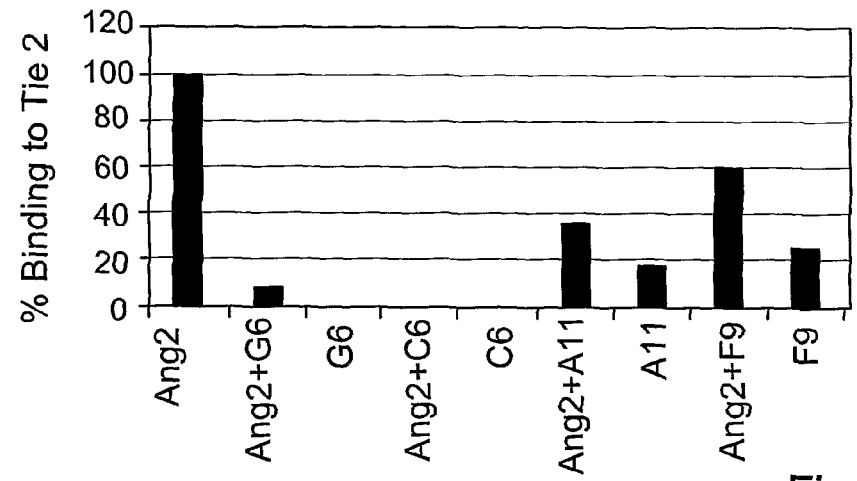
Figure 5C:
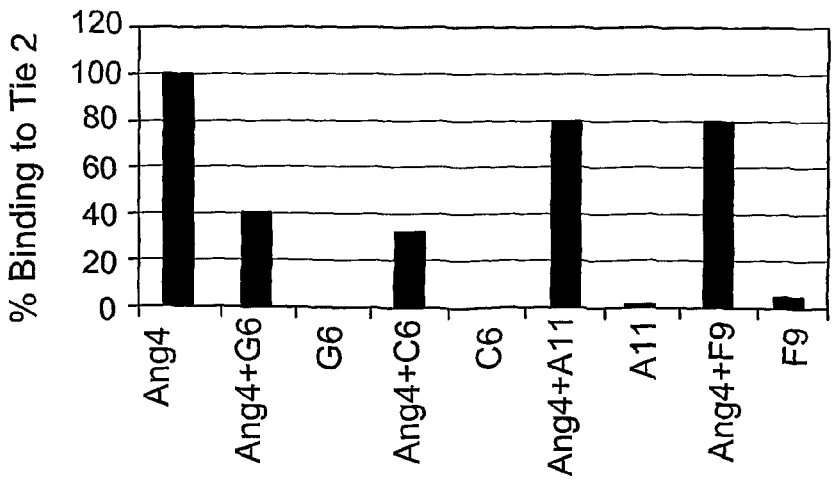

FIG. 5 shows the inhibition of Ang1, Ang2, and Ang4 binding to Tie2 immobilized to the chip by the various peptides, as well as their direct binding to immobilized Tie2. Binding of Ang1 to Tie2 was reduced by up to 34% after incubation with CGEN-G6 [SEQ ID NO: 6], CGEN-C6 [SEQ ID NO: 9], CGEN-A11 [SEQ ID NO: 10], and CGEN-F9 [SEQ ID NO: 7] peptides (FIG. 5A). Binding of Ang2 to Tie2 was reduced by 91-100% after incubation with CGEN-G6 [SEQ ID NO: 6] and CGEN-C6 [SEQ ID NO: 9], and to a lesser extent after incubation with CGEN-A11 [SEQ ID NO: 10] and CGEN-F9 [SEQ ID NO: 7] peptides (FIG. 5B). Binding of Ang4 to Tie2 was reduced by 60-67% after incubation with CGEN-G6 [SEQ ID NO: 6] and CGEN-C6 [SEQ ID NO: 9], and to a lesser extent after incubation with CGEN-A11 [SEQ ID NO: 10] and CGEN-F9 [SEQ ID NO: 7] peptides (FIG. 5C). Binding of peptides alone to Tie2 was negligible in most cases.

Example 7

Analysis of Activity of Peptides According to at Least Some Embodiments of the Present Invention on Angiogenesis in Ovo CGEN-G6 [SEQ ID NO: 6], CGEN-F9 [SEQ ID NO: 7], CGEN-F12 [SEQ ID NO: 8], CGEN-C6 [SEQ ID NO: 9], CGEN-A11 [SEQ ID NO: 10], and CGEN-G2 [SEQ ID NO: 11], were analyzed for their ability to affect angiogenesis using the in ovo avian chorioallantoic membrane (CAM) model of angiogenesis, which is widely used as a model to examine compounds affecting angiogenesis (Richardson and Singh 2003, *Curr Drug Targets Cardiovasc Haematol Disord.*, 3(2):155-85). Two positive controls were used: fumagillin as a general anti-angiogenic compound, and Tie2 neutralizing antibody as anti-angiogenic inhibitor of the Ang/Tie2 pathway. Leghorn fertilized eggs were incubated for 4 days at 37° C., when a window was opened on the egg's shell, exposing the CAM. Two different doses of peptides (0.5 and 5 nmol/CAM), Tie-2 neutralizing antibody (R&D Systems, Cat# AF313, 10 µg/ml; 0.4 µg/CAM) or fumagillin (Tocris Bioscience, Cat # 1768; 5 µg/CAM) were applied in a 40 µl volume inside an area of 1 cm$^2$ (restricted by a plastic ring) of the CAM on day 9 of embryo development. The appropriate vehicle controls were also tested. Forty-eight hours after treatment and subsequent incubation at 37° C., CAMs were fixed in situ, excised from the eggs, placed on slides and left to air-dry. Pictures were taken through a stereoscope equipped with a digital camera and the total length of the vessels was measured using image analysis software (NIH Image). For each group a total of 17-24 eggs from three different experiments were used. Data are presented as means±SEM and expressed as % of vehicle control. Statistical analysis (ANOVA followed by Dunnett's post-hoc test) was performed using Graph Pad.

Figure 6:
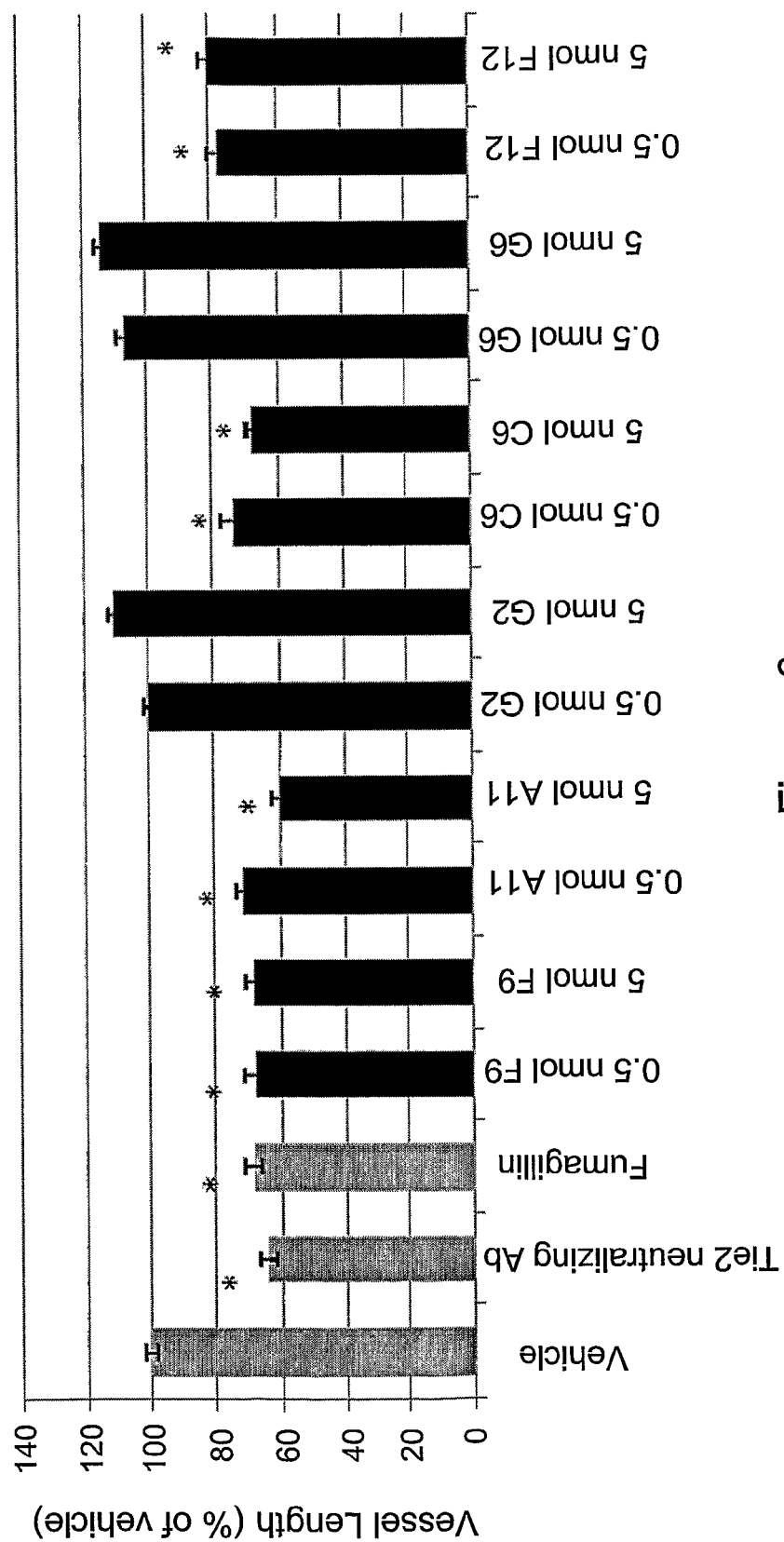
FIG. 6 demonstrates the effect of 0.5 and 5 nmole of peptides CGEN-G6 (SEQ ID NO: 6), CGEN-F9 (SEQ ID NO: 7), CGEN-F12 (SEQ ID NO: 8), CGEN-C6 (SEQ ID NO: 9), CGEN-A11 (SEQ ID NO: 10), and CGEN-G2 (SEQ ID NO: 11) on in ovo angiogenesis in the avian chorioallantoic membrane (CAM) model.

FIG. 6 depict results obtained on vessel length with peptides CGEN-G6 [SEQ ID NO: 6], CGEN-F9 [SEQ ID NO: 7], CGEN-F12 [SEQ ID NO: 8], CGEN-C6 [SEQ ID NO: 9], CGEN-A11 [SEQ ID NO: 10], and CGEN-G2 [SEQ ID NO: 11], compared to Tie2 neutralizing antibody (Ab) and the anti-angiogenic compound fumagillin. Neutralizing Tie2 Ab blocked vessel length by 36%, while the angiogenesis inhibitor fumagillin blocked vessel length by 32%. From the peptides tested, treatment with CGEN-F9 [SEQ ID NO: 7], CGEN-F12 [SEQ ID NO: 8], CGEN-C6 [SEQ ID NO: 9], and CGEN-A11 [SEQ ID NO: 10], resulted in 20-40% inhibition, with CGEN-A11 [SEQ ID NO: 10] having the greatest effect at 5 nmole. The extent of inhibition achieved by treatment with CGEN-F9 [SEQ ID NO: 7], CGEN-A11 [SEQ ID NO: 10] and CGEN-C6 [SEQ ID NO: 9] was similar to that of the positive controls. CGEN-G2 [SEQ ID NO: 11] and CGEN-G6 [SEQ ID NO: 6] did not inhibit angiogenesis in this system. A large number of clots were noted in most of the eggs treated with CGEN-G6 [SEQ ID NO: 6], thus, the results obtained with this peptide should be interpreted with caution.

These results indicate clear anti-angiogenic activity for CGEN-F9 [SEQ ID NO: 7], CGEN-F12 [SEQ ID NO: 8], CGEN-A11 [SEQ ID NO: 10] and CGEN-C6 [SEQ ID NO: 9] and support the potential use of these peptides for the treatment of angiogenesis-related diseases.

Example 8

Anal Sis of the Effect of Peptides According to at Least Some Embodiments of the Present Invention on Tie2 Signaling In order to determine whether peptides according to at least some embodiments of the present inventions inhibit Ang1 and/or Ang2-induced Tie2 signaling, human umbilical vein endothelial cells (EC) are isolated and used to perform Tie2 signaling studies. Human umbilical vein EC are isolated from at least three donors and pooled. Experiments are repeated three times with at least two different batches of donors. Cells are plated in 6 well dishes and treated with two doses of peptide alone or in combination with Ang1 or Ang2. Tie2 phosphorylation by Ang-1 is used as positive control. Cells are incubated with peptide for 15 min, followed by treatment with 250 ng/ml Ang-1 or Ang-2 for 5-10 min. Cells are then lysed and the Tie2 receptor immunoprecipitated and blotted with a phosphotyrosine antibody to determine the phosphorylation levels of Tie2. In parallel, total cell lysates are used to determine the activation of ERK1/2 and Akt by using phospho-specific antibodies for the two kinases. Blots are scanned and bands are quantified using an image analysis software program.

Example 9

Analysis of the Effect of CGEN-A11 [SEQ ID NO: 10] on In Vivo Angiogenesis in a Rodent Model of Oxygen-induced Retinopathy In order to assess the in vivo efficacy of CGEN-A11 [SEQ ID NO: 10] in a disease model of angiogenesis, a rodent model of oxygen-induced retinopathy (OIR) was used. Sprague Dawley rats were raised from birth through day P14 in a variable oxygen atmosphere consisting of 24-hour alternating cycles of 50% and 10% oxygen. Rats were predisposed to pathological retinal angiogenesis as a result of oxygen treatment. Upon removal from the oxygen exposure chamber on day P14, rats received intravitreal injections of CGEN-A11 [SEQ ID NO: 10] in one of two doses: 15 µg/ml (low) or 75 µg/ml (high), 100 µg/ml recombinant rat Tie-2/Fc (R&D Systems, 3874-T2) or 100 µg/ml anti-VEGFR2 (Sigma, V1014) as positive controls, a combination of CGEN-A11 [SEQ ID NO: 10] at 30 µg/ml and anti-VEGFR2 (100 µg/ml), or vehicle (PBS) at a volume of 5 µl. An additional similar intravitreal administration took place 3 days later, on day P17. All pups were sacrificed on day P20. Both normal, intra-retinal vascular growth and abnormal, pre-retinal neovascular growth were assessed at six days post-exposure (P20) in ADPase-stained retinal flat-mounts, using widely published methods (e.g. Penn J S et al., 1991, *Invest Ophthalmol V is Sci.*, 32(4):1147; McLeod D S et al., 1987, *Microvasc Res.*, 33:257-269). All assessments were performed by a single, highly trained observer, who was blinded to treatment group. Areas of normal and abnormal vascular growth were measured via computer-assisted image analysis using high-resolution digital images of the stained retinal flat-mounts. The data were subjected to analysis of variance to determine statistical significance and a Dunnett's post hoc test to identify how the various treatment groups compared.

Figure 7A:
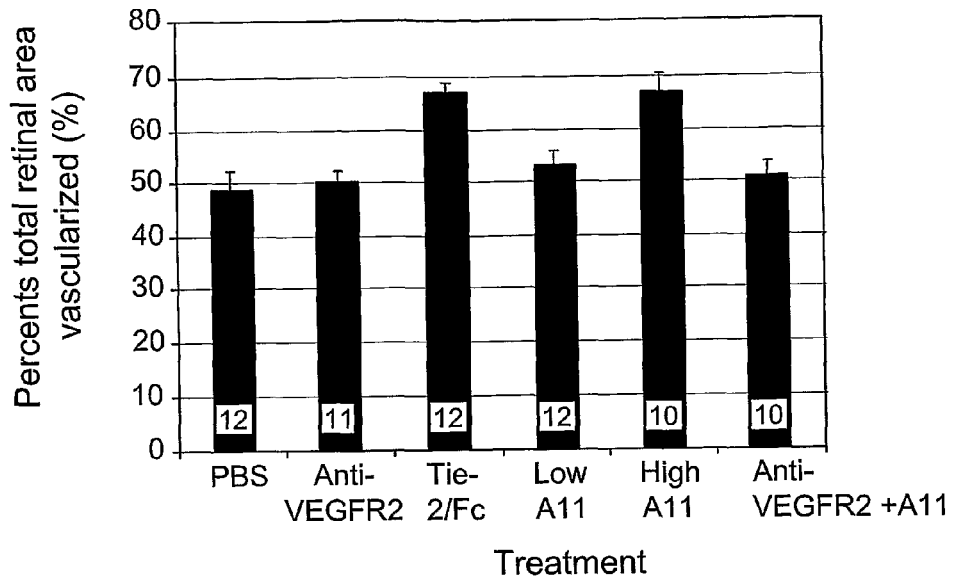
FIG. 7A demonstrates the effect of CGEN-A11 (SEQ ID NO: 10) on intra-retinal vascular development.

FIG. 7A shows the effect of CGEN-A11 [SEQ ID NO: 10] on intra-retinal, i.e. normal vascular development. Data are depicted using percent total retinal area vascularized. Sample sizes (10, 11 or 12) are indicated on each bar. Only CGEN-A11 [SEQ ID NO: 10] at the high concentration of 75 µg/ml and Tie-2/Fc showed a statistically significant increase in intra-retinal normal vascular growth compared to the PBS control. These differences yielded statistical significance, both at $p<0.0001$. Statistical significance was calculated using area ($mm^2$) measurements.

Figure 7B:
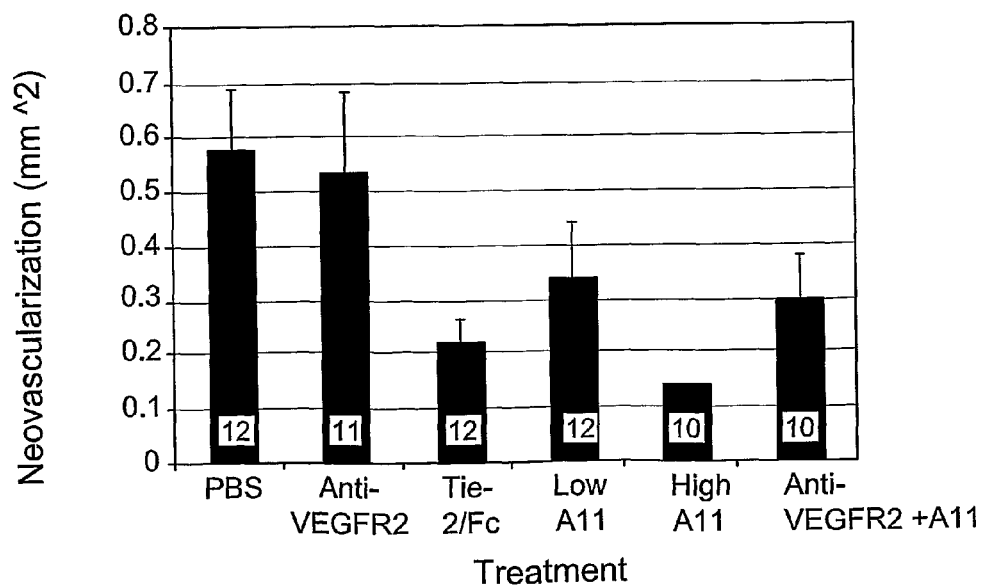
FIG. 7B shows the effect of CGEN-A11 (SEQ ID NO: 10) on pre-retinal neovascular growth.

FIG. 7B shows the effect of CGEN-A11 [SEQ ID NO: 10] on pre-retinal neovascular growth (i.e. pathological angiogenesis). Data are depicted as area vascularized ($mm^2$). Sample sizes (10, 11 or 12) are indicated on each bar. Intravitreal injection of CGEN-A11 [SEQ ID NO: 10] inhibited angiogenesis by 38.9% at the lower concentration (15 µg/ml) and by 76.4% at the higher concentration (75 µg/ml), relative to PBS-injected eyes. Also, Tie-2/Fc showed a 61.9% inhibition of angiogenesis. The 75 µg/ml CGEN-A11 [SEQ ID NO: 10] and 100 µg/ml Tie-2/Fc study arms showed a statistically significant decrease in the pathologic effects of oxygen-induced retinopathy ($p=0.0126$ and $p=0.0436$, respectively.). At this concentration, CGEN-A11 [SEQ ID NO: 10] demonstrated a profound angiostatic potency, outperforming all other test compounds, including Tie-2/Fc (although the difference in the performance of these two treatments was not statistically significant; $p=0.9643$; student's t-test).

Unexpectedly, the anti-VEGFR2 antibody, one of the two positive controls, did not exhibit any inhibition of neovascularization. Although the failure of this antibody to provide efficacy in this assay is atypical, it is not unprecedented, as commercial antibodies frequently demonstrate inconsistent performance from one lot to the next. There are a number of explanations for this, including the presence of endotoxin contamination in the antibody preparation. Accordingly, the CGEN-A11 [SEQ ID NO: 10] is believed to be solely responsible for the efficacy observed in the combined therapy arm, demonstrated in FIG. 7B. The soluble Tie-2 chimera served as an appropriate and adequate positive control and significantly inhibited retinal neovascularization. The profound angiostatic potency of CGEN-A11 [SEQ ID NO: 10] further demonstrated the anti-angiogenic properties of this compound and its potential as a therapeutic compound for angiogenesis-related diseases.

Example 10

Antibodies

Reagents other than peptides are also used to inhibit the formation of the helix-helix interactions between the peptide according to at least some embodiments of the present invention (SEQ ID NOs: 1-11) and the segment corresponding to the partner helix of a peptide according to at least some embodiments of the present invention (SEQ ID NO:48-62). Antibodies that specifically bind to an epitope in the sequence corresponding to the peptide according to at least some embodiments of the present invention (SEQ ID NOs: 1-11) or in the partner helix of a peptide according to at least some embodiments of the present invention (SEQ ID NO:48-62) are highly effective to inhibit the formation of the helix-helix interactions between the two segments and thereby to act as modulators of Ang 1, Ang 2 and/or Ang4.

Thus, antibodies that specifically bind to an epitope in a peptide according to at least some embodiments of the present invention (SEQ ID NOs: 1-11) or in the partner helix of a peptide according to at least some embodiments of the present invention (SEQ ID NO:48-62) or fragments thereof are used for treating wide range of conditions, disorders and diseases, selected from but not limited to cancer, respiratory diseases, metabolic disorders, fibrotic and connective tissue related conditions, urogenital disorders, ocular diseases, vascular anomalies, cardiovascular diseases and their complications, inflammatory conditions associated with an infection, inflammatory disorders, chronic inflammatory diseases, autoimmune diseases, bone disease or bone-related disorder and pain.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. An isolated peptide consisting essentially of an amino acid sequence selected from the group consisting of
   an amino acid sequence as set forth in any one of SEQ ID NO: 10, or a homolog or a derivative thereof,
   wherein said peptide has anti-angiogenic activity, said peptide having at most 32 amino acids.

2. The isolated peptide according to claim 1, wherein said homolog is selected from the group consisting of the amino acid sequence as set forth in SEQ ID NOs. 134-136.

3. A fusion protein comprising the peptide of claim 1 fused to an immunoglobulin molecule.

4. The protein of claim 3, wherein the peptide is fused to an Fc fragment.

5. A pharmaceutical composition comprising the peptide according to claim 1 and a pharmaceutically acceptable carrier.

6. A pharmaceutical composition comprising the peptide according to claim 2 and a pharmaceutically acceptable carrier.

7. A method of treating or preventing an ocular disease in a subject in need thereof comprising administering the pharmaceutical composition according to claim 5 to said subject.

8. The pharmaceutical composition according to claim 5 wherein the pharmaceutically acceptable carrier is a controlled release vehicle, selected from the group consisting of biocompatible polymers, other polymeric matrices, capsules, microcapsules, nanocapsules, microparticles, nanoparticles, microspheres, bolus preparations, osmotic pumps, diffusion devices, liposomes, lipospheres and transdermal delivery systems, implantable or not.

9. The method of claim 7, wherein said ocular disease is an angiogenesis-related ocular disease.

10. The method according to claim 9, wherein the ocular disease is selected from the group consisting of retinal angiogenesis disorder, ocular neovascularisation, retinopathy, age-related macular degeneration, macular oedema, trachoma and corneal neovascularization.

11. The method according to claim 7, further comprising administering an additional therapeutic agent.

12. The method according to claim 11, wherein the additional therapeutic agent is an anti-angiogenic antibody.

13. The method according to claim 12, wherein said anti-angiogenic antibody is selected from the group consisting of bevacizumab and erbitux.

14. The method according to claim 5, wherein administering comprises topical or transdermal administration of the pharmaceutical composition in a formulation selected from the group consisting of an ointment, a paste, a cream, a lotion, an emulsion, a gel, a powder, a solution, a spray, an inhalant and a patch.

15. The isolated peptide of claim 1, wherein said peptide inhibits binding of Tie2 to an angiogenic protein.

16. The isolated peptide of claim 15, wherein said angiopoietin is selected from the group consisting of angiopoietin 1, angiopoetin 2 and angiopoietin 4.

17. The isolated peptide of claim 1, wherein said peptide inhibits in-ovo angiogenesis in the chorio-allantoic membranes of a fertilized egg.

\* \* \* \* \*

```
                        SEQUENCE LISTING

<160> NUMBER OF SEQ ID NOS: 186

<210> SEQ ID NO 1
<211> LENGTH: 30
<212> TYPE: PRT
<213> ORGANISM: Artificial
<220> FEATURE:
<223> OTHER INFORMATION: Synthetic polypeptide

<400> SEQUENCE: 1

Leu Lys Glu Glu Lys Glu Asn Leu Gln Gly Leu Val Thr Arg Gln Thr
1               5                   10                  15

Tyr Ile Ile Gln Glu Leu Glu Lys Gln Leu Asn Arg Ala Thr
            20                  25                  30

<210> SEQ ID NO 2
<211> LENGTH: 11
<212> TYPE: PRT
<213> ORGANISM: Artificial
<220> FEATURE:
<223> OTHER INFORMATION: Synthetic polypeptide

<400> SEQUENCE: 2

Thr Asn Asn Ser Val Leu Gln Lys Gln Gln Leu
1               5                   10

<210> SEQ ID NO 3
<211> LENGTH: 11
<212> TYPE: PRT
<213> ORGANISM: Artificial
<220> FEATURE:
<223> OTHER INFORMATION: Synthetic polypeptide

<400> SEQUENCE: 3

Leu Met Asp Thr Val His Asn Leu Val Asn Leu
1               5                   10

<210> SEQ ID NO 4
<211> LENGTH: 25
<212> TYPE: PRT
<213> ORGANISM: Artificial
<220> FEATURE:
<223> OTHER INFORMATION: Synthetic polypeptide

<400> SEQUENCE: 4

Asn Glu Ile Leu Lys Ile His Glu Lys Asn Ser Leu Leu Glu His Lys
1               5                   10                  15

Ile Leu Glu Met Glu Gly Lys His Lys
            20                  25

<210> SEQ ID NO 5
<211> LENGTH: 16
<212> TYPE: PRT
<213> ORGANISM: Artificial
<220> FEATURE:
<223> OTHER INFORMATION: Synthetic polypeptide
```

-continued

```
<400> SEQUENCE: 5

Gln Leu Gln Val Leu Val Ser Lys Gln Asn Ser Ile Ile Glu Glu Leu
1               5                   10                  15

<210> SEQ ID NO 6
<211> LENGTH: 21
<212> TYPE: PRT
<213> ORGANISM: Artificial
<220> FEATURE:
<223> OTHER INFORMATION: Synthetic polypeptide

<400> SEQUENCE: 6

Asp Leu Met Glu Thr Val Asn Asn Leu Leu Thr Met Met Ser Thr Ser
1               5                   10                  15

Asn Ser Ala Lys Asp
            20

<210> SEQ ID NO 7
<211> LENGTH: 36
<212> TYPE: PRT
<213> ORGANISM: Artificial
<220> FEATURE:
<223> OTHER INFORMATION: Synthetic polypeptide

<400> SEQUENCE: 7

Gln Glu Glu Leu Ala Ser Ile Leu Ser Lys Lys Ala Lys Leu Leu Asn
1               5                   10                  15

Thr Leu Ser Arg Gln Ser Ala Ala Leu Thr Asn Ile Glu Arg Gly Leu
            20                  25                  30

Arg Gly Val Arg
        35

<210> SEQ ID NO 8
<211> LENGTH: 23
<212> TYPE: PRT
<213> ORGANISM: Artificial
<220> FEATURE:
<223> OTHER INFORMATION: Synthetic polypeptide

<400> SEQUENCE: 8

Gln His Ser Leu Arg Gln Leu Leu Val Leu Leu Arg His Leu Val Gln
1               5                   10                  15

Glu Arg Ala Asn Ala Ser Ala
            20

<210> SEQ ID NO 9
<211> LENGTH: 18
<212> TYPE: PRT
<213> ORGANISM: Artificial
<220> FEATURE:
<223> OTHER INFORMATION: Synthetic polypeptide

<400> SEQUENCE: 9

Thr Asp Met Glu Ala Gln Leu Leu Asn Gln Thr Ser Arg Met Asp Ala
1               5                   10                  15

Gln Met

<210> SEQ ID NO 10
<211> LENGTH: 12
<212> TYPE: PRT
<213> ORGANISM: Artificial
<220> FEATURE:
<223> OTHER INFORMATION: Synthetic polypeptide
```

```
<400> SEQUENCE: 10

Glu Thr Phe Leu Ser Thr Asn Lys Leu Glu Asn Gln
1               5                   10

<210> SEQ ID NO 11
<211> LENGTH: 29
<212> TYPE: PRT
<213> ORGANISM: Artificial
<220> FEATURE:
<223> OTHER INFORMATION: Synthetic polypeptide

<400> SEQUENCE: 11

Thr Gln Gln Val Lys Gln Leu Glu Gln Ala Leu Gln Asn Asn Thr Gln
1               5                   10                  15

Trp Leu Lys Lys Leu Glu Arg Ala Ile Lys Thr Ile Leu
            20                  25

<210> SEQ ID NO 12
<211> LENGTH: 50
<212> TYPE: PRT
<213> ORGANISM: Artificial
<220> FEATURE:
<223> OTHER INFORMATION: Synthetic polypeptide

<400> SEQUENCE: 12

Glu Gly Lys His Lys Glu Glu Leu Asp Thr Leu Lys Glu Glu Lys Glu
1               5                   10                  15

Asn Leu Gln Gly Leu Val Thr Arg Gln Thr Tyr Ile Ile Gln Glu Leu
            20                  25                  30

Glu Lys Gln Leu Asn Arg Ala Thr Thr Asn Asn Ser Val Leu Gln Lys
        35                  40                  45

Gln Gln
    50

<210> SEQ ID NO 13
<211> LENGTH: 32
<212> TYPE: PRT
<213> ORGANISM: Artificial
<220> FEATURE:
<223> OTHER INFORMATION: Synthetic polypeptide

<400> SEQUENCE: 13

Gln Glu Leu Glu Lys Gln Leu Asn Arg Ala Thr Thr Asn Asn Ser Val
1               5                   10                  15

Leu Gln Lys Gln Gln Leu Glu Leu Met Asp Thr Val His Asn Leu Val
            20                  25                  30

<210> SEQ ID NO 14
<211> LENGTH: 31
<212> TYPE: PRT
<213> ORGANISM: Artificial
<220> FEATURE:
<223> OTHER INFORMATION: Synthetic polypeptide

<400> SEQUENCE: 14

Asn Ser Val Leu Gln Lys Gln Gln Leu Glu Leu Met Asp Thr Val His
1               5                   10                  15

Asn Leu Val Asn Leu Cys Thr Lys Glu Gly Val Leu Leu Lys Gly
            20                  25                  30

<210> SEQ ID NO 15
<211> LENGTH: 45
<212> TYPE: PRT
<213> ORGANISM: Artificial
```

```
<220> FEATURE:
<223> OTHER INFORMATION: Synthetic polypeptide

<400> SEQUENCE: 15

Lys Leu Glu Lys Gln Leu Leu Gln Gln Thr Asn Glu Ile Leu Lys Ile
1               5                   10                  15

His Glu Lys Asn Ser Leu Leu Glu His Lys Ile Leu Glu Met Glu Gly
                20                  25                  30

Lys His Lys Glu Glu Leu Asp Thr Leu Lys Glu Glu Lys
                35                  40                  45

<210> SEQ ID NO 16
<211> LENGTH: 36
<212> TYPE: PRT
<213> ORGANISM: Artificial
<220> FEATURE:
<223> OTHER INFORMATION: Synthetic polypeptide

<400> SEQUENCE: 16

Gln Leu Gln Ser Ile Lys Glu Glu Lys Asp Gln Leu Gln Val Leu Val
1               5                   10                  15

Ser Lys Gln Asn Ser Ile Ile Glu Glu Leu Glu Lys Lys Ile Val Thr
                20                  25                  30

Ala Thr Val Asn
        35

<210> SEQ ID NO 17
<211> LENGTH: 41
<212> TYPE: PRT
<213> ORGANISM: Artificial
<220> FEATURE:
<223> OTHER INFORMATION: Synthetic polypeptide

<400> SEQUENCE: 17

Asn Asn Ser Val Leu Gln Lys Gln Gln His Asp Leu Met Glu Thr Val
1               5                   10                  15

Asn Asn Leu Leu Thr Met Met Ser Thr Ser Asn Ser Ala Lys Asp Pro
                20                  25                  30

Thr Val Ala Lys Glu Glu Gln Ile Ser
        35                  40

<210> SEQ ID NO 18
<211> LENGTH: 56
<212> TYPE: PRT
<213> ORGANISM: Artificial
<220> FEATURE:
<223> OTHER INFORMATION: Synthetic polypeptide

<400> SEQUENCE: 18

Lys Arg Leu Gln Ala Leu Glu Thr Lys Gln Gln Glu Glu Leu Ala Ser
1               5                   10                  15

Ile Leu Ser Lys Lys Ala Lys Leu Leu Asn Thr Leu Ser Arg Gln Ser
                20                  25                  30

Ala Ala Leu Thr Asn Ile Glu Arg Gly Leu Arg Gly Val Arg His Asn
        35                  40                  45

Ser Ser Leu Leu Gln Asp Gln Gln
    50                  55

<210> SEQ ID NO 19
<211> LENGTH: 43
<212> TYPE: PRT
<213> ORGANISM: Artificial
```

```
<220> FEATURE:
<223> OTHER INFORMATION: Synthetic polypeptide

<400> SEQUENCE: 19

Arg His Asn Ser Ser Leu Leu Gln Asp Gln Gln His Ser Leu Arg Gln
1               5                   10                  15

Leu Leu Val Leu Leu Arg His Leu Val Gln Glu Arg Ala Asn Ala Ser
            20                  25                  30

Ala Pro Ala Phe Ile Met Ala Gly Glu Gln Val
        35                  40

<210> SEQ ID NO 20
<211> LENGTH: 38
<212> TYPE: PRT
<213> ORGANISM: Artificial
<220> FEATURE:
<223> OTHER INFORMATION: Synthetic polypeptide

<400> SEQUENCE: 20

Asn Gln Thr Thr Ala Gln Ile Arg Lys Leu Thr Asp Met Glu Ala Gln
1               5                   10                  15

Leu Leu Asn Gln Thr Ser Arg Met Asp Ala Gln Met Pro Glu Thr Phe
            20                  25                  30

Leu Ser Thr Asn Lys Leu
        35

<210> SEQ ID NO 21
<211> LENGTH: 32
<212> TYPE: PRT
<213> ORGANISM: Artificial
<220> FEATURE:
<223> OTHER INFORMATION: Synthetic polypeptide

<400> SEQUENCE: 21

Gln Thr Ser Arg Met Asp Ala Gln Met Pro Glu Thr Phe Leu Ser Thr
1               5                   10                  15

Asn Lys Leu Glu Asn Gln Leu Leu Leu Gln Arg Gln Lys Leu Gln Gln
            20                  25                  30

<210> SEQ ID NO 22
<211> LENGTH: 49
<212> TYPE: PRT
<213> ORGANISM: Artificial
<220> FEATURE:
<223> OTHER INFORMATION: Synthetic polypeptide

<400> SEQUENCE: 22

Ala Asn Pro Leu His Leu Gly Lys Leu Pro Thr Gln Gln Val Lys Gln
1               5                   10                  15

Leu Glu Gln Ala Leu Gln Asn Asn Thr Gln Trp Leu Lys Lys Leu Glu
            20                  25                  30

Arg Ala Ile Lys Thr Ile Leu Arg Ser Lys Leu Glu Gln Val Gln Gln
        35                  40                  45

Gln

<210> SEQ ID NO 23
<211> LENGTH: 90
<212> TYPE: DNA
<213> ORGANISM: Artificial
<220> FEATURE:
<223> OTHER INFORMATION: Synthetic polynucleotide
```

<400> SEQUENCE: 23
ttaaaggaag agaaagagaa ccttcaaggc ttggttactc gtcaaacata tataatccag    60
gagctggaaa agcaattaaa cagagctacc    90

<210> SEQ ID NO 24
<211> LENGTH: 33
<212> TYPE: DNA
<213> ORGANISM: Artificial
<220> FEATURE:
<223> OTHER INFORMATION: Synthetic polynucleotide

<400> SEQUENCE: 24
accaacaaca gtgtccttca gaagcagcaa ctg    33

<210> SEQ ID NO 25
<211> LENGTH: 33
<212> TYPE: DNA
<213> ORGANISM: Artificial
<220> FEATURE:
<223> OTHER INFORMATION: Synthetic polynucleotide

<400> SEQUENCE: 25
ctgatggaca cagtccacaa ccttgtcaat ctt    33

<210> SEQ ID NO 26
<211> LENGTH: 75
<212> TYPE: DNA
<213> ORGANISM: Artificial
<220> FEATURE:
<223> OTHER INFORMATION: Synthetic polynucleotide

<400> SEQUENCE: 26
aatgaaatct tgaagatcca tgaaaaaaac agtttattag aacataaaat cttagaaatg    60
gaaggaaaac acaag    75

<210> SEQ ID NO 27
<211> LENGTH: 48
<212> TYPE: DNA
<213> ORGANISM: Artificial
<220> FEATURE:
<223> OTHER INFORMATION: Synthetic polynucleotide

<400> SEQUENCE: 27
cagctacagg tgttagtatc caagcaaaat tccatcattg aagaacta    48

<210> SEQ ID NO 28
<211> LENGTH: 63
<212> TYPE: DNA
<213> ORGANISM: Artificial
<220> FEATURE:
<223> OTHER INFORMATION: Synthetic polynucleotide

<400> SEQUENCE: 28
gatctcatgg agacagttaa taacttactg actatgatgt ccacatcaaa ctcagctaag    60
gac    63

<210> SEQ ID NO 29
<211> LENGTH: 108
<212> TYPE: DNA
<213> ORGANISM: Artificial
<220> FEATURE:
<223> OTHER INFORMATION: Synthetic polynucleotide

```
<400> SEQUENCE: 29
caggaggagc tggccagcat cctcagcaag aaggcgaagc tgctgaacac gctgagccgc      60
cagagcgccg ccctcaccaa catcgagcgc ggcctgcgcg tgtcagg                   108

<210> SEQ ID NO 30
<211> LENGTH: 73
<212> TYPE: DNA
<213> ORGANISM: Artificial
<220> FEATURE:
<223> OTHER INFORMATION: Synthetic polynucleotide

<400> SEQUENCE: 30
cagcacagcc tgcgccagct gctggtgttg ttgcggcacc tggtgcaaga aagggctaac      60
gcctcggccc cgg                                                        73

<210> SEQ ID NO 31
<211> LENGTH: 54
<212> TYPE: DNA
<213> ORGANISM: Artificial
<220> FEATURE:
<223> OTHER INFORMATION: Synthetic polynucleotide

<400> SEQUENCE: 31
accgacatgg aggctcagct cctgaaccag acatcaagaa tggatgccca gatg            54

<210> SEQ ID NO 32
<211> LENGTH: 36
<212> TYPE: DNA
<213> ORGANISM: Artificial
<220> FEATURE:
<223> OTHER INFORMATION: Synthetic polynucleotide

<400> SEQUENCE: 32
gagacctttc tgtccaccaa caagctggag aaccag                                36

<210> SEQ ID NO 33
<211> LENGTH: 87
<212> TYPE: DNA
<213> ORGANISM: Artificial
<220> FEATURE:
<223> OTHER INFORMATION: Synthetic polynucleotide

<400> SEQUENCE: 33
acccagcagg tgaaacagct ggagcaggca ctgcagaaca acacgcagtg gctgaagaag      60
ctagagaggg ccatcaagac gatcttg                                         87

<210> SEQ ID NO 34
<211> LENGTH: 150
<212> TYPE: DNA
<213> ORGANISM: Artificial
<220> FEATURE:
<223> OTHER INFORMATION: Synthetic polynucleotide

<400> SEQUENCE: 34
gaaggaaaac acaaggaaga gttggacacc ttaaaggaag agaaagagaa ccttcaaggc      60
ttggttactc gtcaaacata tataatccag gagctggaaa agcaattaaa cagagctacc     120
accaacaaca gtgtccttca gaagcagcaa                                     150

<210> SEQ ID NO 35
<211> LENGTH: 96
<212> TYPE: DNA
<213> ORGANISM: Artificial
```

```
<220> FEATURE:
<223> OTHER INFORMATION: Synthetic polynucleotide

<400> SEQUENCE: 35
caggagctgg aaaagcaatt aaacagagct accaccaaca acagtgtcct tcagaagcag    60
caactggagc tgatggacac agtccacaac cttgtc                              96

<210> SEQ ID NO 36
<211> LENGTH: 93
<212> TYPE: DNA
<213> ORGANISM: Artificial
<220> FEATURE:
<223> OTHER INFORMATION: Synthetic polynucleotide

<400> SEQUENCE: 36
aacagtgtcc ttcagaagca gcaactggag ctgatggaca cagtccacaa ccttgtcaat    60
ctttgcacta aagaaggtgt tttactaaag gga                                 93

<210> SEQ ID NO 37
<211> LENGTH: 134
<212> TYPE: DNA
<213> ORGANISM: Artificial
<220> FEATURE:
<223> OTHER INFORMATION: Synthetic polynucleotide

<400> SEQUENCE: 37
aagctagaga agcaacttct tcaacagaca aatgaaatct tgaagatcca tgaaaaaaac    60
agtttattag aacataaaat cttagaaatg gaaggaaaac acaaggaaga ttggacacct   120
taaaggaaga gaaa                                                    134

<210> SEQ ID NO 38
<211> LENGTH: 108
<212> TYPE: DNA
<213> ORGANISM: Artificial
<220> FEATURE:
<223> OTHER INFORMATION: Synthetic polynucleotide

<400> SEQUENCE: 38
caactacagt caataaaaga agagaaagat cagctacagg tgttagtatc caagcaaaat    60
tccatcattg aagaactaga aaaaaaaata gtgactgcca cggtgaat               108

<210> SEQ ID NO 39
<211> LENGTH: 123
<212> TYPE: DNA
<213> ORGANISM: Artificial
<220> FEATURE:
<223> OTHER INFORMATION: Synthetic polynucleotide

<400> SEQUENCE: 39
aataattcag ttcttcagaa gcagcaacat gatctcatgg agacagttaa taacttactg    60
actatgatgt ccacatcaaa ctcagctaag gaccccactg ttgctaaaga agaacaaatc   120
agc                                                                123

<210> SEQ ID NO 40
<211> LENGTH: 168
<212> TYPE: DNA
<213> ORGANISM: Artificial
<220> FEATURE:
<223> OTHER INFORMATION: Synthetic polynucleotide
```

```
<400> SEQUENCE: 40
aagcggttgc aggccctgga gaccaagcag caggaggagc tggccagcat cctcagcaag    60
aaggcgaagc tgctgaacac gctgagccgc cagagcgccg ccctcaccaa catcgagcgc   120
ggcctgcgcg gtgtcaggca caactccagc ctcctgcagg accagcag               168

<210> SEQ ID NO 41
<211> LENGTH: 133
<212> TYPE: DNA
<213> ORGANISM: Artificial
<220> FEATURE:
<223> OTHER INFORMATION: Synthetic polynucleotide

<400> SEQUENCE: 41
aggcacaact ccagcctcct gcaggaccag cagcacagcc tgcgccagct gctggtgttg    60
ttgcggcacc tggtgcaaga aagggctaac gcctcggccc cggccttcat aatggcaggt   120
gagcaggtgt tcc                                                     133

<210> SEQ ID NO 42
<211> LENGTH: 114
<212> TYPE: DNA
<213> ORGANISM: Artificial
<220> FEATURE:
<223> OTHER INFORMATION: Synthetic polynucleotide

<400> SEQUENCE: 42
aaccagacca ctgcccagat ccgcaagctg accgacatgg aggctcagct cctgaaccag    60
acatcaagaa tggatgccca gatgccagag acctttctgt ccaccaacaa gctg         114

<210> SEQ ID NO 43
<211> LENGTH: 96
<212> TYPE: DNA
<213> ORGANISM: Artificial
<220> FEATURE:
<223> OTHER INFORMATION: Synthetic polynucleotide

<400> SEQUENCE: 43
cagacatcaa gaatggatgc ccagatgcca gagacctttc tgtccaccaa caagctggag    60
aaccagctgc tgctacagag gcagaagctc cagcag                             96

<210> SEQ ID NO 44
<211> LENGTH: 147
<212> TYPE: DNA
<213> ORGANISM: Artificial
<220> FEATURE:
<223> OTHER INFORMATION: Synthetic polynucleotide

<400> SEQUENCE: 44
gccaacccac tgcacctggg gaagttgccc acccagcagg tgaaacagct ggagcaggca    60
ctgcagaaca acacgcagtg gctgaagaag ctagagaggg ccatcaagac gatcttgagg   120
tcgaagctgg agcaggtcca gcagcaa                                      147

<210> SEQ ID NO 45
<211> LENGTH: 498
<212> TYPE: PRT
<213> ORGANISM: Homo sapiens
```

<400> SEQUENCE: 45

```
Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
    50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
            260                 265                 270

Lys Gly Gly Lys Arg Glu Glu Glu Lys Pro Phe Arg Asp Cys Ala Asp
        275                 280                 285

Val Tyr Gln Ala Gly Phe Asn Lys Ser Gly Ile Tyr Thr Ile Tyr Ile
    290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
        355                 360                 365

Arg Gln Tyr Met Leu Arg Ile Glu Leu Met Asp Trp Glu Gly Asn Arg
    370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415
```

-continued

```
Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
        435                 440                 445

Phe Asp Ala Cys Gly Pro Ser Asn Leu Asn Gly Met Phe Tyr Thr Ala
450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 46
<211> LENGTH: 496
<212> TYPE: PRT
<213> ORGANISM: Homo sapiens

<400> SEQUENCE: 46

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Gly Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285
```

```
Lys Ser Gly His Thr Thr Asn Gly Ile Tyr Thr Leu Thr Phe Pro Asn
        290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 47
<211> LENGTH: 503
<212> TYPE: PRT
<213> ORGANISM: Homo sapiens

<400> SEQUENCE: 47

Met Leu Ser Gln Leu Ala Met Leu Gln Gly Ser Leu Leu Leu Val Val
1               5                   10                  15

Ala Thr Met Ser Val Ala Gln Gln Thr Arg Gln Glu Ala Asp Arg Gly
                20                  25                  30

Cys Glu Thr Leu Val Val Gln His Gly His Cys Ser Tyr Thr Phe Leu
            35                  40                  45

Leu Pro Lys Ser Glu Pro Cys Pro Pro Gly Pro Glu Val Ser Arg Asp
        50                  55                  60

Ser Asn Thr Leu Gln Arg Glu Ser Leu Ala Asn Pro Leu His Leu Gly
65                  70                  75                  80

Lys Leu Pro Thr Gln Gln Val Lys Gln Leu Glu Gln Ala Leu Gln Asn
                85                  90                  95

Asn Thr Gln Trp Leu Lys Lys Leu Glu Arg Ala Ile Lys Thr Ile Leu
            100                 105                 110

Arg Ser Lys Leu Glu Gln Val Gln Gln Met Ala Gln Asn Gln Thr
        115                 120                 125

Ala Pro Met Leu Glu Leu Gly Thr Ser Leu Leu Asn Gln Thr Thr Ala
130                 135                 140

Gln Ile Arg Lys Leu Thr Asp Met Glu Ala Gln Leu Leu Asn Gln Thr
145                 150                 155                 160
```

-continued

```
Ser Arg Met Asp Ala Gln Met Pro Glu Thr Phe Leu Ser Thr Asn Lys
            165                 170                 175

Leu Glu Asn Gln Leu Leu Leu Gln Arg Gln Lys Leu Gln Leu Gln Leu
        180                 185                 190

Gly Gln Asn Ser Ala Leu Glu Lys Arg Leu Gln Ala Leu Glu Thr Lys
    195                 200                 205

Gln Gln Glu Glu Leu Ala Ser Ile Leu Ser Lys Ala Lys Leu Leu
210                 215                 220

Asn Thr Leu Ser Arg Gln Ser Ala Ala Leu Thr Asn Ile Glu Arg Gly
225                 230                 235                 240

Leu Arg Gly Val Arg His Asn Ser Ser Leu Leu Gln Asp Gln Gln His
                245                 250                 255

Ser Leu Arg Gln Leu Leu Val Leu Leu Arg His Leu Val Gln Glu Arg
            260                 265                 270

Ala Asn Ala Ser Ala Pro Ala Phe Ile Met Ala Gly Glu Gln Val Phe
        275                 280                 285

Gln Asp Cys Ala Glu Ile Gln Arg Ser Gly Ala Ser Ala Ser Gly Val
    290                 295                 300

Tyr Thr Ile Gln Val Ser Asn Ala Thr Lys Pro Arg Lys Val Phe Cys
305                 310                 315                 320

Asp Leu Gln Ser Ser Gly Gly Arg Trp Thr Leu Ile Gln Arg Arg Glu
                325                 330                 335

Asn Gly Thr Val Asn Phe Gln Arg Asn Trp Lys Asp Tyr Lys Gln Gly
            340                 345                 350

Phe Gly Asp Pro Ala Gly Glu His Trp Leu Gly Asn Glu Val Val His
        355                 360                 365

Gln Leu Thr Arg Arg Ala Ala Tyr Ser Leu Arg Val Glu Leu Gln Asp
    370                 375                 380

Trp Glu Gly His Glu Ala Tyr Ala Gln Tyr Glu His Phe His Leu Gly
385                 390                 395                 400

Ser Glu Asn Gln Leu Tyr Arg Leu Ser Val Val Gly Tyr Ser Gly Ser
                405                 410                 415

Ala Gly Arg Gln Ser Ser Leu Val Leu Gln Asn Thr Ser Phe Ser Thr
            420                 425                 430

Leu Asp Ser Asp Asn Asp His Cys Leu Cys Lys Cys Ala Gln Val Met
        435                 440                 445

Ser Gly Gly Trp Trp Phe Asp Ala Cys Gly Leu Ser Asn Leu Asn Gly
    450                 455                 460

Val Tyr Tyr His Ala Pro Asp Asn Lys Tyr Lys Met Asp Gly Ile Arg
465                 470                 475                 480

Trp His Tyr Phe Lys Gly Pro Ser Tyr Ser Leu Arg Ala Ser Arg Met
                485                 490                 495

Met Ile Arg Pro Leu Asp Ile
            500
```

<210> SEQ ID NO 48
<211> LENGTH: 36
<212> TYPE: PRT
<213> ORGANISM: Artificial
<220> FEATURE:
<223> OTHER INFORMATION: Synthetic polypeptide -continued

```
<400> SEQUENCE: 48

Ala Thr Met Leu Glu Ile Gly Thr Ser Leu Leu Ser Gln Thr Ala Glu
1               5                   10                  15

Gln Thr Arg Lys Leu Thr Asp Val Glu Thr Gln Val Leu Asn Gln Thr
            20                  25                  30

Ser Arg Leu Glu
        35

<210> SEQ ID NO 49
<211> LENGTH: 16
<212> TYPE: PRT
<213> ORGANISM: Artificial
<220> FEATURE:
<223> OTHER INFORMATION: Synthetic polypeptide

<400> SEQUENCE: 49

Leu Thr Asp Val Glu Thr Gln Val Leu Asn Gln Thr Ser Arg Leu Glu
1               5                   10                  15

<210> SEQ ID NO 50
<211> LENGTH: 33
<212> TYPE: PRT
<213> ORGANISM: Artificial
<220> FEATURE:
<223> OTHER INFORMATION: Synthetic polypeptide

<400> SEQUENCE: 50

Thr Met Leu Glu Ile Gly Thr Ser Leu Leu Ser Gln Thr Ala Glu Gln
1               5                   10                  15

Thr Arg Lys Leu Thr Asp Val Glu Thr Gln Val Leu Asn Gln Thr Ser
            20                  25                  30

Arg

<210> SEQ ID NO 51
<211> LENGTH: 36
<212> TYPE: PRT
<213> ORGANISM: Artificial
<220> FEATURE:
<223> OTHER INFORMATION: Synthetic polypeptide

<400> SEQUENCE: 51

Leu Thr Asp Val Glu Thr Gln Val Leu Asn Gln Thr Ser Arg Leu Glu
1               5                   10                  15

Ile Gln Leu Leu Glu Asn Ser Leu Ser Thr Tyr Lys Leu Glu Lys Gln
            20                  25                  30

Leu Leu Gln Gln
        35

<210> SEQ ID NO 52
<211> LENGTH: 36
<212> TYPE: PRT
<213> ORGANISM: Artificial
<220> FEATURE:
<223> OTHER INFORMATION: Synthetic polypeptide

<400> SEQUENCE: 52

Gln Thr Ala Val Met Ile Glu Ile Gly Thr Asn Leu Leu Asn Gln Thr
1               5                   10                  15

Ala Glu Gln Thr Arg Lys Leu Thr Asp Val Glu Ala Gln Val Leu Asn
            20                  25                  30

Gln Thr Thr Arg
        35
```

```
<210> SEQ ID NO 53
<211> LENGTH: 36
<212> TYPE: PRT
<213> ORGANISM: Artificial
<220> FEATURE:
<223> OTHER INFORMATION: Synthetic polypeptide

<400> SEQUENCE: 53

Arg Lys Leu Thr Asp Val Glu Ala Gln Val Leu Asn Gln Thr Thr Arg
1               5                   10                  15

Leu Glu Leu Gln Leu Leu Glu His Ser Leu Ser Thr Asn Lys Leu Glu
            20                  25                  30

Lys Gln Ile Leu
        35

<210> SEQ ID NO 54
<211> LENGTH: 21
<212> TYPE: PRT
<213> ORGANISM: Artificial
<220> FEATURE:
<223> OTHER INFORMATION: Synthetic polypeptide

<400> SEQUENCE: 54

Arg Lys Leu Thr Asp Val Glu Ala Gln Val Leu Asn Gln Thr Thr Arg
1               5                   10                  15

Leu Glu Leu Gln Leu
            20

<210> SEQ ID NO 55
<211> LENGTH: 41
<212> TYPE: PRT
<213> ORGANISM: Artificial
<220> FEATURE:
<223> OTHER INFORMATION: Synthetic polypeptide

<400> SEQUENCE: 55

Val Glu Ala Gln Val Leu Asn Gln Thr Thr Arg Leu Glu Leu Gln Leu
1               5                   10                  15

Leu Glu His Ser Leu Ser Thr Asn Lys Leu Glu Lys Gln Ile Leu Asp
            20                  25                  30

Gln Thr Ser Glu Ile Asn Lys Leu Gln
        35                  40

<210> SEQ ID NO 56
<211> LENGTH: 26
<212> TYPE: PRT
<213> ORGANISM: Artificial
<220> FEATURE:
<223> OTHER INFORMATION: Synthetic polypeptide

<400> SEQUENCE: 56

Thr Ala Glu Gln Thr Arg Lys Leu Thr Asp Val Glu Ala Gln Val Leu
1               5                   10                  15

Asn Gln Thr Thr Arg Leu Glu Leu Gln Leu
            20                  25

<210> SEQ ID NO 57
<211> LENGTH: 51
<212> TYPE: PRT
<213> ORGANISM: Artificial
<220> FEATURE:
<223> OTHER INFORMATION: Synthetic polypeptide
```

```
<400> SEQUENCE: 57

Phe Leu Glu Lys Lys Val Leu Ala Met Glu Asp Lys His Ile Ile Gln
1               5                   10                  15

Leu Gln Ser Ile Lys Glu Glu Lys Asp Gln Leu Gln Val Leu Val Ser
            20                  25                  30

Lys Gln Asn Ser Ile Ile Glu Glu Leu Glu Lys Lys Ile Val Thr Ala
        35                  40                  45

Thr Val Asn
        50

<210> SEQ ID NO 58
<211> LENGTH: 41
<212> TYPE: PRT
<213> ORGANISM: Artificial
<220> FEATURE:
<223> OTHER INFORMATION: Synthetic polypeptide

<400> SEQUENCE: 58

Gln Leu Leu Val Leu Leu Arg His Leu Val Gln Glu Arg Ala Asn Ala
1               5                   10                  15

Ser Ala Pro Ala Phe Ile Met Ala Gly Glu Gln Val Phe Gln Asp Cys
            20                  25                  30

Ala Glu Ile Gln Arg Ser Gly Ala Ser
        35                  40

<210> SEQ ID NO 59
<211> LENGTH: 16
<212> TYPE: PRT
<213> ORGANISM: Artificial
<220> FEATURE:
<223> OTHER INFORMATION: Synthetic polypeptide

<400> SEQUENCE: 59

Gln Leu Leu Val Leu Leu Arg His Leu Val Gln Glu Arg Ala Asn Ala
1               5                   10                  15

<210> SEQ ID NO 60
<211> LENGTH: 39
<212> TYPE: PRT
<213> ORGANISM: Artificial
<220> FEATURE:
<223> OTHER INFORMATION: Synthetic polypeptide

<400> SEQUENCE: 60

Asn Gln Thr Ala Pro Met Leu Glu Leu Gly Thr Ser Leu Leu Asn Gln
1               5                   10                  15

Thr Thr Ala Gln Ile Arg Lys Leu Thr Asp Met Glu Ala Gln Leu Leu
            20                  25                  30

Asn Gln Thr Ser Arg Met Asp
        35

<210> SEQ ID NO 61
<211> LENGTH: 43
<212> TYPE: PRT
<213> ORGANISM: Artificial
<220> FEATURE:
<223> OTHER INFORMATION: Synthetic polypeptide
```

-continued

```
<400> SEQUENCE: 61

Gln Leu Leu Val Leu Leu Arg His Leu Val Gln Glu Arg Ala Asn Ala
1               5                   10                  15

Ser Ala Pro Ala Phe Ile Met Ala Gly Glu Gln Val Phe Gln Asp Cys
            20                  25                  30

Ala Glu Ile Gln Arg Ser Gly Ala Ser Ala Ser
        35                  40

<210> SEQ ID NO 62
<211> LENGTH: 32
<212> TYPE: PRT
<213> ORGANISM: Artificial
<220> FEATURE:
<223> OTHER INFORMATION: Synthetic polypeptide

<400> SEQUENCE: 62

Ser Asn Thr Leu Gln Arg Glu Ser Leu Ala Asn Pro Leu His Leu Gly
1               5                   10                  15

Lys Leu Pro Thr Gln Gln Val Lys Gln Leu Glu Gln Ala Leu Gln Asn
            20                  25                  30

<210> SEQ ID NO 63
<211> LENGTH: 21
<212> TYPE: PRT
<213> ORGANISM: Artificial
<220> FEATURE:
<223> OTHER INFORMATION: Synthetic polypeptide

<400> SEQUENCE: 63

Asp Leu Met Glu Thr Val Asn Ser Leu Leu Thr Met Met Ser Ser Pro
1               5                   10                  15

Asp Tyr Lys Ser Ser
            20

<210> SEQ ID NO 64
<211> LENGTH: 21
<212> TYPE: PRT
<213> ORGANISM: Artificial
<220> FEATURE:
<223> OTHER INFORMATION: Synthetic polypeptide

<400> SEQUENCE: 64

Asp Leu Met Glu Thr Val His Ser Leu Leu Thr Met Ile Ser Pro Ser
1               5                   10                  15

Lys Ser Pro Lys Asp
            20

<210> SEQ ID NO 65
<211> LENGTH: 20
<212> TYPE: PRT
<213> ORGANISM: Artificial
<220> FEATURE:
<223> OTHER INFORMATION: Synthetic polypeptide

<400> SEQUENCE: 65

Asp Leu Met Glu Thr Val Asn Asn Leu Leu Thr Met Met Ser Thr Ser
1               5                   10                  15

Asn Ser Lys Asp
            20

<210> SEQ ID NO 66
<211> LENGTH: 20
<212> TYPE: PRT
<213> ORGANISM: Artificial
```

```
<220> FEATURE:
<223> OTHER INFORMATION: Synthetic polypeptide

<400> SEQUENCE: 66

Asp Leu Met Glu Thr Val His Ser Leu Leu Thr Met Ile Thr Ala Pro
1               5                   10                  15

Asn Ser Lys Asn
            20

<210> SEQ ID NO 67
<211> LENGTH: 21
<212> TYPE: PRT
<213> ORGANISM: Artificial
<220> FEATURE:
<223> OTHER INFORMATION: Synthetic polypeptide

<400> SEQUENCE: 67

Asp Leu Met Glu Thr Val His Asn Leu Leu Thr Met Ile Ser Thr Pro
1               5                   10                  15

Asn Ser Ala Lys Lys
            20

<210> SEQ ID NO 68
<211> LENGTH: 21
<212> TYPE: PRT
<213> ORGANISM: Artificial
<220> FEATURE:
<223> OTHER INFORMATION: Synthetic polypeptide

<400> SEQUENCE: 68

Asp Leu Met Glu Thr Val His Asn Leu Leu Thr Met Ile Ser Ser Pro
1               5                   10                  15

Asn Ser Ala Lys Asn
            20

<210> SEQ ID NO 69
<211> LENGTH: 21
<212> TYPE: PRT
<213> ORGANISM: Artificial
<220> FEATURE:
<223> OTHER INFORMATION: Synthetic polypeptide

<400> SEQUENCE: 69

Asp Leu Met Glu Thr Val His Asn Leu Leu Thr Met Ile Ser Thr Pro
1               5                   10                  15

Asn Ser Ala Lys Asn
            20

<210> SEQ ID NO 70
<211> LENGTH: 21
<212> TYPE: PRT
<213> ORGANISM: Artificial
<220> FEATURE:
<223> OTHER INFORMATION: Synthetic polypeptide

<400> SEQUENCE: 70

Asp Leu Met Glu Thr Val His Asn Leu Leu Thr Met Ile Ser Thr Ser
1               5                   10                  15

Asn Ser Ala Lys His
            20

<210> SEQ ID NO 71
<211> LENGTH: 21
<212> TYPE: PRT
<213> ORGANISM: Artificial
```

```
<220> FEATURE:
<223> OTHER INFORMATION: Synthetic polypeptide

<400> SEQUENCE: 71

Asp Leu Met Glu Thr Val Asn Ser Leu Leu Thr Met Met Ser Ser Pro
1               5                   10                  15

Asn Ser Lys Ser Ser
            20

<210> SEQ ID NO 72
<211> LENGTH: 20
<212> TYPE: PRT
<213> ORGANISM: Artificial
<220> FEATURE:
<223> OTHER INFORMATION: Synthetic polypeptide

<400> SEQUENCE: 72

Asp Leu Met Glu Thr Val Asn Asn Leu Leu Thr Leu Met Ser Thr Ser
1               5                   10                  15

Asn Pro Ser Tyr
            20

<210> SEQ ID NO 73
<211> LENGTH: 16
<212> TYPE: PRT
<213> ORGANISM: Artificial
<220> FEATURE:
<223> OTHER INFORMATION: Synthetic polypeptide

<400> SEQUENCE: 73

Gln Leu Gln Val Leu Val Ser Lys Gln Ser Ser Val Ile Asp Glu Leu
1               5                   10                  15

<210> SEQ ID NO 74
<211> LENGTH: 16
<212> TYPE: PRT
<213> ORGANISM: Artificial
<220> FEATURE:
<223> OTHER INFORMATION: Synthetic polypeptide

<400> SEQUENCE: 74

Gln Leu Gln Val Leu Val Ser Arg Gln Asn Ser Ile Ile Glu Glu Leu
1               5                   10                  15

<210> SEQ ID NO 75
<211> LENGTH: 16
<212> TYPE: PRT
<213> ORGANISM: Artificial
<220> FEATURE:
<223> OTHER INFORMATION: Synthetic polypeptide

<400> SEQUENCE: 75

Gln Leu Gln Val Leu Val Ala Arg Gln Asn Ser Ile Ile Glu Glu Leu
1               5                   10                  15

<210> SEQ ID NO 76
<211> LENGTH: 16
<212> TYPE: PRT
<213> ORGANISM: Artificial
<220> FEATURE:
<223> OTHER INFORMATION: Synthetic polypeptide

<400> SEQUENCE: 76

Glu Leu Gln Val Leu Val Ser Lys Gln Ser Ser Val Ile Asp Glu Leu
1               5                   10                  15
```

```
<210> SEQ ID NO 77
<211> LENGTH: 41
<212> TYPE: PRT
<213> ORGANISM: Artificial
<220> FEATURE:
<223> OTHER INFORMATION: Synthetic polypeptide

<400> SEQUENCE: 77

Asn Asn Ser Val Leu Gln Lys Gln Gln His Asp Leu Met Glu Thr Val
1               5                   10                  15

His Ser Leu Leu Thr Met Ile Ser Pro Ser Lys Ser Pro Lys Asp Thr
            20                  25                  30

Phe Val Ala Lys Glu Glu Gln Ile Ile
        35                  40

<210> SEQ ID NO 78
<211> LENGTH: 40
<212> TYPE: PRT
<213> ORGANISM: Artificial
<220> FEATURE:
<223> OTHER INFORMATION: Synthetic polypeptide

<400> SEQUENCE: 78

Asn Asn Ser Val Leu Gln Lys Gln Gln His Asp Leu Met Glu Thr Val
1               5                   10                  15

Asn Asn Leu Leu Thr Met Met Ser Thr Ser Asn Ser Lys Asp Pro Thr
            20                  25                  30

Val Ala Lys Glu Glu Gln Ile Ser
        35                  40

<210> SEQ ID NO 79
<211> LENGTH: 40
<212> TYPE: PRT
<213> ORGANISM: Artificial
<220> FEATURE:
<223> OTHER INFORMATION: Synthetic polypeptide

<400> SEQUENCE: 79

Asn Asn Ser Val Leu Gln Lys Gln Gln His Asp Leu Met Glu Thr Val
1               5                   10                  15

His Ser Leu Leu Thr Met Ile Thr Ala Pro Asn Ser Lys Asn Ser Phe
            20                  25                  30

Val Ala Lys Glu Glu Gln Ile Ile
        35                  40

<210> SEQ ID NO 80
<211> LENGTH: 41
<212> TYPE: PRT
<213> ORGANISM: Artificial
<220> FEATURE:
<223> OTHER INFORMATION: Synthetic polypeptide

<400> SEQUENCE: 80

Asn Asn Ser Val Leu Gln Lys Gln Gln His Asp Leu Met Glu Thr Val
1               5                   10                  15

His Asn Leu Leu Thr Met Ile Ser Thr Pro Asn Ser Ala Lys Lys Asn
            20                  25                  30

Phe Ile Ala Lys Glu Glu Gln Ile Ser
        35                  40

<210> SEQ ID NO 81
<211> LENGTH: 41
<212> TYPE: PRT
<213> ORGANISM: Artificial
```

-continued

```
<220> FEATURE:
<223> OTHER INFORMATION: Synthetic polypeptide

<400> SEQUENCE: 81

Asn Asn Ser Val Leu Gln Lys Gln Gln His Asp Leu Met Glu Thr Val
1               5                   10                  15

His Asn Leu Leu Thr Met Ile Ser Ser Pro Asn Ser Ala Lys Asn Ser
            20                  25                  30

Phe Val Ala Lys Glu Glu Gln Ile Leu
        35                  40

<210> SEQ ID NO 82
<211> LENGTH: 41
<212> TYPE: PRT
<213> ORGANISM: Artificial
<220> FEATURE:
<223> OTHER INFORMATION: Synthetic polypeptide

<400> SEQUENCE: 82

Asn Asn Ser Val Leu Gln Lys Gln Gln His Asp Leu Met Glu Thr Val
1               5                   10                  15

His Asn Leu Leu Thr Met Ile Ser Thr Pro Asn Ser Ala Lys Asn Ser
            20                  25                  30

Phe Ala Ala Lys Glu Glu Gln Ile Ile
        35                  40

<210> SEQ ID NO 83
<211> LENGTH: 41
<212> TYPE: PRT
<213> ORGANISM: Artificial
<220> FEATURE:
<223> OTHER INFORMATION: Synthetic polypeptide

<400> SEQUENCE: 83

Asn Asn Ser Val Leu Gln Lys Gln Gln His Asp Leu Met Glu Thr Val
1               5                   10                  15

His Asn Leu Leu Thr Met Ile Ser Thr Ser Asn Ser Ala Lys His Ser
            20                  25                  30

Leu Val Ala Lys Glu Glu Gln Ile Ile
        35                  40

<210> SEQ ID NO 84
<211> LENGTH: 41
<212> TYPE: PRT
<213> ORGANISM: Artificial
<220> FEATURE:
<223> OTHER INFORMATION: Synthetic polypeptide

<400> SEQUENCE: 84

Asn Asn Ser Leu Leu Gln Lys Gln Gln His Asp Leu Met Glu Thr Val
1               5                   10                  15

Asn Ser Leu Leu Thr Met Met Ser Ser Pro Asn Ser Lys Ser Ser Val
            20                  25                  30

Ala Ile Arg Lys Glu Glu Gln Thr Thr
        35                  40

<210> SEQ ID NO 85
<211> LENGTH: 40
<212> TYPE: PRT
<213> ORGANISM: Artificial
<220> FEATURE:
<223> OTHER INFORMATION: Synthetic polypeptide
```

```
<400> SEQUENCE: 85

Asn Asn Ser Val Leu Gln Lys Gln Gln His Asp Leu Met Glu Thr Val
1               5                   10                  15

Asn Asn Leu Leu Thr Leu Met Ser Thr Ser Asn Pro Ser Tyr Ser Leu
            20                  25                  30

Leu Ala Lys Asp Glu Gln Ile Ile
        35                  40

<210> SEQ ID NO 86
<211> LENGTH: 36
<212> TYPE: PRT
<213> ORGANISM: Artificial
<220> FEATURE:
<223> OTHER INFORMATION: Synthetic polypeptide

<400> SEQUENCE: 86

Gln Leu Gln Ser Met Lys Glu Gln Lys Asp Gln Leu Gln Val Leu Val
1               5                   10                  15

Ser Lys Gln Ser Ser Val Ile Asp Glu Leu Glu Lys Lys Leu Val Thr
            20                  25                  30

Ala Thr Val Asn
        35

<210> SEQ ID NO 87
<211> LENGTH: 36
<212> TYPE: PRT
<213> ORGANISM: Artificial
<220> FEATURE:
<223> OTHER INFORMATION: Synthetic polypeptide

<400> SEQUENCE: 87

Gln Leu Arg Ser Ile Lys Glu Glu Lys Asp Gln Leu Gln Val Leu Val
1               5                   10                  15

Ser Lys Gln Asn Ser Ile Ile Glu Glu Leu Glu Lys Gln Leu Val Thr
            20                  25                  30

Ala Thr Val Asn
        35

<210> SEQ ID NO 88
<211> LENGTH: 36
<212> TYPE: PRT
<213> ORGANISM: Artificial
<220> FEATURE:
<223> OTHER INFORMATION: Synthetic polypeptide

<400> SEQUENCE: 88

Gln Leu Gln Ser Ile Lys Asp Glu Lys Asp Gln Leu Gln Val Leu Val
1               5                   10                  15

Ser Arg Gln Asn Ser Ile Ile Glu Glu Leu Glu Lys Gln Leu Val Thr
            20                  25                  30

Ala Thr Ala Asn
        35

<210> SEQ ID NO 89
<211> LENGTH: 36
<212> TYPE: PRT
<213> ORGANISM: Artificial
<220> FEATURE:
<223> OTHER INFORMATION: Synthetic polypeptide
```

<400> SEQUENCE: 89

Gln Leu Lys Ser Ile Lys Asp Glu Lys Asp Gln Leu Gln Val Leu Val
1               5                   10                  15

Ala Arg Gln Asn Ser Ile Ile Glu Glu Leu Glu Lys Gln Leu Val Thr
                20                  25                  30

Ala Thr Val Asn
        35

<210> SEQ ID NO 90
<211> LENGTH: 36
<212> TYPE: PRT
<213> ORGANISM: Artificial
<220> FEATURE:
<223> OTHER INFORMATION: Synthetic polypeptide

<400> SEQUENCE: 90

Gln Leu Gln Ser Ile Lys Asp Glu Lys Asp Gln Leu Gln Val Leu Val
1               5                   10                  15

Ser Arg Gln Asn Ser Ile Ile Glu Glu Leu Glu Lys Gln Leu Val Thr
                20                  25                  30

Ala Thr Val Asn
        35

<210> SEQ ID NO 91
<211> LENGTH: 36
<212> TYPE: PRT
<213> ORGANISM: Artificial
<220> FEATURE:
<223> OTHER INFORMATION: Synthetic polypeptide

<400> SEQUENCE: 91

Gln Leu Gln Ser Ile Lys Glu Glu Lys Asp Gln Leu Gln Val Leu Val
1               5                   10                  15

Ser Lys Gln Asn Ser Ile Ile Glu Glu Leu Glu Lys Gln Leu Val Thr
                20                  25                  30

Ala Thr Val Asn
        35

<210> SEQ ID NO 92
<211> LENGTH: 36
<212> TYPE: PRT
<213> ORGANISM: Artificial
<220> FEATURE:
<223> OTHER INFORMATION: Synthetic polypeptide

<400> SEQUENCE: 92

Gln Leu Gln Ser Met Lys Glu Gln Lys Asp Glu Leu Gln Val Leu Val
1               5                   10                  15

Ser Lys Gln Ser Ser Val Ile Asp Glu Leu Glu Lys Lys Leu Val Thr
                20                  25                  30

Ala Thr Val Asn
        35

<210> SEQ ID NO 93
<211> LENGTH: 38
<212> TYPE: PRT
<213> ORGANISM: Artificial
<220> FEATURE:
<223> OTHER INFORMATION: Synthetic polypeptide

```
<400> SEQUENCE: 93

Asn Gln Thr Thr Ala Gln Thr Arg Lys Leu Thr Asp Met Glu Ala Gln
1               5                   10                  15

Leu Leu Asn Gln Thr Ser Arg Met Asp Ala Gln Met Pro Glu Thr Phe
            20                  25                  30

Leu Ser Thr Asn Lys Leu
        35

<210> SEQ ID NO 94
<211> LENGTH: 38
<212> TYPE: PRT
<213> ORGANISM: Artificial
<220> FEATURE:
<223> OTHER INFORMATION: Synthetic polypeptide

<400> SEQUENCE: 94

Thr Gln Thr Thr Ala Gln Thr Arg Lys Leu Thr Asp Val Glu Ala Gln
1               5                   10                  15

Val Leu Asn Gln Thr Ser Arg Met Glu Ile Gln Leu Leu Glu Thr Ser
            20                  25                  30

Leu Ser Thr Asn Lys Leu
        35

<210> SEQ ID NO 95
<211> LENGTH: 38
<212> TYPE: PRT
<213> ORGANISM: Artificial
<220> FEATURE:
<223> OTHER INFORMATION: Synthetic polypeptide

<400> SEQUENCE: 95

Asn Gln Thr Thr Ala Gln Thr Arg Lys Leu Thr Asp Val Glu Ala Gln
1               5                   10                  15

Val Leu Asn Gln Thr Ser Arg Met Glu Ile Gln Leu Leu Glu Thr Ser
            20                  25                  30

Leu Ser Thr Asn Lys Leu
        35

<210> SEQ ID NO 96
<211> LENGTH: 38
<212> TYPE: PRT
<213> ORGANISM: Artificial
<220> FEATURE:
<223> OTHER INFORMATION: Synthetic polypeptide

<400> SEQUENCE: 96

Asn Gln Thr Lys Ala Gln Thr His Lys Leu Thr Ala Val Glu Ala Gln
1               5                   10                  15

Val Leu Asn Gln Thr Leu His Met Lys Thr Gln Met Leu Glu Asn Ser
            20                  25                  30

Leu Ser Thr Asn Lys Leu
        35

<210> SEQ ID NO 97
<211> LENGTH: 38
<212> TYPE: PRT
<213> ORGANISM: Artificial
<220> FEATURE:
<223> OTHER INFORMATION: Synthetic polypeptide
```

```
<400> SEQUENCE: 97

Asn Gln Thr Met Ala Gln Thr His Lys Leu Thr Ala Val Glu Ala Gln
1               5                   10                  15

Val Leu Asn His Thr Ser Arg Val Lys Thr Gln Met Leu Glu Ser Ser
            20                  25                  30

Leu Ser Thr Asn Lys Leu
        35

<210> SEQ ID NO 98
<211> LENGTH: 36
<212> TYPE: PRT
<213> ORGANISM: Artificial
<220> FEATURE:
<223> OTHER INFORMATION: Synthetic polypeptide

<400> SEQUENCE: 98

Gln Glu Glu Leu Ala Ser Ile Leu Ser Lys Lys Ala Lys Leu Leu Asn
1               5                   10                  15

Thr Leu Ser Arg Gln Ser Ala Ala Leu Thr Asn Ile Glu Arg Arg Leu
            20                  25                  30

Arg Asp Val Arg
        35

<210> SEQ ID NO 99
<211> LENGTH: 36
<212> TYPE: PRT
<213> ORGANISM: Artificial
<220> FEATURE:
<223> OTHER INFORMATION: Synthetic polypeptide

<400> SEQUENCE: 99

Gln Ala Glu Leu Ala Ser Leu Ser Gly Glu Lys Glu Arg Leu Arg Arg
1               5                   10                  15

Leu Leu Gly Arg Gln Ser Gly Ala Leu Ala Gly Leu Glu Arg Thr Leu
            20                  25                  30

Arg Ala Ala Ser
        35

<210> SEQ ID NO 100
<211> LENGTH: 36
<212> TYPE: PRT
<213> ORGANISM: Artificial
<220> FEATURE:
<223> OTHER INFORMATION: Synthetic polypeptide

<400> SEQUENCE: 100

Gln Ala Glu Leu Ala Ser Leu Arg Gly Glu Lys Glu Arg Leu Arg Arg
1               5                   10                  15

Leu Leu Gly Arg Gln Ser Gly Ala Leu Ala Gly Leu Glu Arg Ser Leu
            20                  25                  30

Arg Ala Ala Ser
        35

<210> SEQ ID NO 101
<211> LENGTH: 36
<212> TYPE: PRT
<213> ORGANISM: Artificial
<220> FEATURE:
<223> OTHER INFORMATION: Synthetic polypeptide
```

```
<400> SEQUENCE: 101

Gln Ala Gln Leu Asn Ser Leu Gln Glu Lys Arg Glu Gln Leu His Ser
1               5                   10                  15

Leu Leu Gly His Gln Thr Gly Thr Leu Ala Asn Leu Lys His Asn Leu
                20                  25                  30

His Ala Leu Ser
        35

<210> SEQ ID NO 102
<211> LENGTH: 36
<212> TYPE: PRT
<213> ORGANISM: Artificial
<220> FEATURE:
<223> OTHER INFORMATION: Synthetic polypeptide

<400> SEQUENCE: 102

Gln Ala Gln Leu Asn Ser Leu Gln Asp Lys Arg Glu Gln Leu Gln Ser
1               5                   10                  15

Leu Leu Gly His Gln Thr Gly Ala Leu Ala Asn Leu Lys His Ser Leu
                20                  25                  30

Arg Ala Leu Ser
        35

<210> SEQ ID NO 103
<211> LENGTH: 32
<212> TYPE: PRT
<213> ORGANISM: Artificial
<220> FEATURE:
<223> OTHER INFORMATION: Synthetic polypeptide

<400> SEQUENCE: 103

Gln Thr Ser Arg Met Glu Ile Gln Leu Leu Glu Thr Ser Leu Ser Thr
1               5                   10                  15

Asn Lys Leu Glu Lys Gln Leu Leu Gln Gly His Glu Leu His Arg
                20                  25                  30

<210> SEQ ID NO 104
<211> LENGTH: 32
<212> TYPE: PRT
<213> ORGANISM: Artificial
<220> FEATURE:
<223> OTHER INFORMATION: Synthetic polypeptide

<400> SEQUENCE: 104

Gln Thr Leu His Met Lys Thr Gln Met Leu Glu Asn Ser Leu Ser Thr
1               5                   10                  15

Asn Lys Leu Glu Arg Gln Met Leu Met Gln Ser Arg Glu Leu Gln Arg
                20                  25                  30

<210> SEQ ID NO 105
<211> LENGTH: 32
<212> TYPE: PRT
<213> ORGANISM: Artificial
<220> FEATURE:
<223> OTHER INFORMATION: Synthetic polypeptide

<400> SEQUENCE: 105

His Thr Ser Arg Val Lys Thr Gln Met Leu Glu Ser Ser Leu Ser Thr
1               5                   10                  15

Asn Lys Leu Glu Arg Gln Met Leu Met Gln Ser Arg Glu Leu Gln Arg
                20                  25                  30
```

```
<210> SEQ ID NO 106
<211> LENGTH: 23
<212> TYPE: PRT
<213> ORGANISM: Artificial
<220> FEATURE:
<223> OTHER INFORMATION: Synthetic polypeptide

<400> SEQUENCE: 106

Gln His Ser Leu Ser Gln Leu Leu Leu Leu Arg Asp Leu Val Gln
1               5                   10                  15

Glu Arg Val Asn Ala Ser Ala
            20

<210> SEQ ID NO 107
<211> LENGTH: 18
<212> TYPE: PRT
<213> ORGANISM: Artificial
<220> FEATURE:
<223> OTHER INFORMATION: Synthetic polypeptide

<400> SEQUENCE: 107

Gln His Gln Leu Leu Glu Ser Val Gln Arg Leu Val Arg Val Met Ala
1               5                   10                  15

Gln Gly

<210> SEQ ID NO 108
<211> LENGTH: 18
<212> TYPE: PRT
<213> ORGANISM: Artificial
<220> FEATURE:
<223> OTHER INFORMATION: Synthetic polypeptide

<400> SEQUENCE: 108

Gln Arg Gln Leu Leu Glu Ser Val Gln Arg Leu Val Arg Val Val Ala
1               5                   10                  15

Gln Gly

<210> SEQ ID NO 109
<211> LENGTH: 18
<212> TYPE: PRT
<213> ORGANISM: Artificial
<220> FEATURE:
<223> OTHER INFORMATION: Synthetic polypeptide

<400> SEQUENCE: 109

Gln Gln Gln Leu Thr Glu Phe Val Gln Arg Leu Val Arg Ile Val Ala
1               5                   10                  15

Gln Asp

<210> SEQ ID NO 110
<211> LENGTH: 18
<212> TYPE: PRT
<213> ORGANISM: Artificial
<220> FEATURE:
<223> OTHER INFORMATION: Synthetic polypeptide

<400> SEQUENCE: 110

Gln Gln Gln Leu Met Glu Leu Val Gln Arg Leu Val Arg Ile Val Ala
1               5                   10                  15

Gln Asp

<210> SEQ ID NO 111
<211> LENGTH: 49
<212> TYPE: PRT
<213> ORGANISM: Artificial
```

```
<220> FEATURE:
<223> OTHER INFORMATION: Synthetic polypeptide

<400> SEQUENCE: 111

Ala Asn Pro Leu Arg Leu Glu Lys Leu Pro Thr Gln Gln Val Lys Arg
1               5                   10                  15

Leu Glu Gln Ala Leu Gln Asn Asn Thr Gln Trp Leu Lys Lys Leu Glu
            20                  25                  30

Arg Ala Ile Lys Met Ile Leu Arg Ser Lys Leu Val Gln Val Gln Gln
        35                  40                  45

Gln

<210> SEQ ID NO 112
<211> LENGTH: 49
<212> TYPE: PRT
<213> ORGANISM: Artificial
<220> FEATURE:
<223> OTHER INFORMATION: Synthetic polypeptide

<400> SEQUENCE: 112

Ala Ala Thr Leu Asn Leu Gly Asp Trp Pro Ser Gln Arg Met Arg Gln
1               5                   10                  15

Leu Glu Lys Met Leu Glu Asn Asn Thr Gln Trp Leu Gln Lys Leu Glu
            20                  25                  30

Arg Tyr Ile Gln Val Asn Leu Arg Leu Glu Leu Ala Gln Ala Gln Gln
        35                  40                  45

His

<210> SEQ ID NO 113
<211> LENGTH: 49
<212> TYPE: PRT
<213> ORGANISM: Artificial
<220> FEATURE:
<223> OTHER INFORMATION: Synthetic polypeptide

<400> SEQUENCE: 113

Ala Ala Pro Leu Asn Leu Gly Asp Trp Pro Thr Gln Arg Val Gln Gln
1               5                   10                  15

Leu Glu Lys Val Leu Glu Asn Asn Thr Gln Trp Leu Gln Lys Leu Glu
            20                  25                  30

Arg Tyr Ile Gln Met Asn Leu Arg Ser Glu Leu Ala Gln Val Gln Gln
        35                  40                  45

His

<210> SEQ ID NO 114
<211> LENGTH: 55
<212> TYPE: PRT
<213> ORGANISM: Artificial
<220> FEATURE:
<223> OTHER INFORMATION: Synthetic polypeptide

<400> SEQUENCE: 114

Ala Ser Arg Leu His Leu Thr Asp Trp Arg Ala Gln Arg Ala Gln Arg
1               5                   10                  15

Ala Gln Arg Val Ser Gln Leu Glu Lys Ile Leu Glu Asn Asn Thr Gln
            20                  25                  30

Trp Leu Leu Lys Leu Glu Gln Ser Ile Lys Val Asn Leu Arg Ser His
        35                  40                  45

Leu Val Gln Ala Gln Gln Asp
    50                  55
```

```
<210> SEQ ID NO 115
<211> LENGTH: 55
<212> TYPE: PRT
<213> ORGANISM: Artificial
<220> FEATURE:
<223> OTHER INFORMATION: Synthetic polypeptide

<400> SEQUENCE: 115

Ala Ala Arg His His Leu Thr Asp Trp Arg Ala Gln Arg Ala Gln Arg
1               5                   10                  15

Ala Gln Arg Val Ser Gln Leu Glu Lys Ile Leu Glu Asn Asn Thr Gln
            20                  25                  30

Trp Leu Leu Lys Leu Glu Gln Ser Ile Gln Met Asn Leu Arg Ser Asp
        35                  40                  45

Leu Ala Gln Ala Gln Gln His
    50                  55

<210> SEQ ID NO 116
<211> LENGTH: 18
<212> TYPE: PRT
<213> ORGANISM: Artificial
<220> FEATURE:
<223> OTHER INFORMATION: Synthetic polypeptide

<400> SEQUENCE: 116

Thr Asp Val Glu Ala Gln Val Leu Asn Gln Thr Ser Arg Met Glu Ile
1               5                   10                  15

Gln Leu

<210> SEQ ID NO 117
<211> LENGTH: 18
<212> TYPE: PRT
<213> ORGANISM: Artificial
<220> FEATURE:
<223> OTHER INFORMATION: Synthetic polypeptide

<400> SEQUENCE: 117

Thr Ala Val Glu Ala Gln Val Leu Asn Gln Thr Leu His Met Lys Thr
1               5                   10                  15

Gln Met

<210> SEQ ID NO 118
<211> LENGTH: 18
<212> TYPE: PRT
<213> ORGANISM: Artificial
<220> FEATURE:
<223> OTHER INFORMATION: Synthetic polypeptide

<400> SEQUENCE: 118

Thr Ala Val Glu Ala Gln Val Leu Asn His Thr Ser Arg Val Lys Thr
1               5                   10                  15

Gln Met

<210> SEQ ID NO 119
<211> LENGTH: 56
<212> TYPE: PRT
<213> ORGANISM: Artificial
<220> FEATURE:
<223> OTHER INFORMATION: Synthetic polypeptide
```

```
<400> SEQUENCE: 119

Lys Arg Leu Gln Ala Leu Glu Thr Lys Gln Gln Glu Leu Ala Ser
1               5                   10                  15

Ile Leu Ser Lys Lys Ala Lys Leu Leu Asn Thr Leu Ser Arg Gln Ser
            20                  25                  30

Ala Ala Leu Thr Asn Ile Glu Arg Arg Leu Arg Asp Val Arg His Asn
        35                  40                  45

Ser Ser Leu Leu Gln Asp Gln Gln
        50                  55

<210> SEQ ID NO 120
<211> LENGTH: 56
<212> TYPE: PRT
<213> ORGANISM: Artificial
<220> FEATURE:
<223> OTHER INFORMATION: Synthetic polypeptide

<400> SEQUENCE: 120

Thr Arg Val Gln Ala Leu Glu Thr Gln Gln Gln Ala Glu Leu Ala Ser
1               5                   10                  15

Leu Ser Gly Glu Lys Glu Arg Leu Arg Arg Leu Leu Gly Arg Gln Ser
            20                  25                  30

Gly Ala Leu Ala Gly Leu Glu Arg Thr Leu Arg Ala Ala Ser Ser Asn
        35                  40                  45

Ser Ser Leu Leu Gln Arg Gln Gln
        50                  55

<210> SEQ ID NO 121
<211> LENGTH: 56
<212> TYPE: PRT
<213> ORGANISM: Artificial
<220> FEATURE:
<223> OTHER INFORMATION: Synthetic polypeptide

<400> SEQUENCE: 121

Thr Arg Val Gln Ala Leu Glu Thr Gln Gln Gln Ala Glu Leu Ala Ser
1               5                   10                  15

Leu Arg Gly Glu Lys Glu Arg Leu Arg Arg Leu Leu Gly Arg Gln Ser
            20                  25                  30

Gly Ala Leu Ala Gly Leu Glu Arg Ser Leu Arg Ala Ala Ser Ser Asn
        35                  40                  45

Ser Ser Leu Leu Gln Arg Gln Gln
        50                  55

<210> SEQ ID NO 122
<211> LENGTH: 56
<212> TYPE: PRT
<213> ORGANISM: Artificial
<220> FEATURE:
<223> OTHER INFORMATION: Synthetic polypeptide

<400> SEQUENCE: 122

Thr Arg Leu Gln Ala Leu Glu Ala Gln His Gln Ala Gln Leu Asn Ser
1               5                   10                  15

Leu Gln Glu Lys Arg Glu Gln Leu His Ser Leu Leu Gly His Gln Thr
            20                  25                  30

Gly Thr Leu Ala Asn Leu Lys His Asn Leu His Ala Leu Ser Ser Asn
        35                  40                  45

Ser Ser Ser Leu Gln Gln Gln Gln
        50                  55
```

<210> SEQ ID NO 123
<211> LENGTH: 56
<212> TYPE: PRT
<213> ORGANISM: Artificial
<220> FEATURE:
<223> OTHER INFORMATION: Synthetic polypeptide

<400> SEQUENCE: 123

Thr Arg Leu Gln Ala Leu Glu Ala Gln His Gln Ala Gln Leu Asn Ser
1               5                   10                  15

Leu Gln Asp Lys Arg Glu Gln Leu Gln Ser Leu Leu Gly His Gln Thr
            20                  25                  30

Gly Ala Leu Ala Asn Leu Lys His Ser Leu Arg Ala Leu Ser Ser Asn
        35                  40                  45

Ser Ser Ser Leu Gln Gln Gln Gln
        50                  55

<210> SEQ ID NO 124
<211> LENGTH: 29
<212> TYPE: PRT
<213> ORGANISM: Artificial
<220> FEATURE:
<223> OTHER INFORMATION: Synthetic polypeptide

<400> SEQUENCE: 124

Thr Gln Gln Val Lys Arg Leu Glu Gln Ala Leu Gln Asn Asn Thr Gln
1               5                   10                  15

Trp Leu Lys Lys Leu Glu Arg Ala Ile Lys Met Ile Leu
            20                  25

<210> SEQ ID NO 125
<211> LENGTH: 29
<212> TYPE: PRT
<213> ORGANISM: Artificial
<220> FEATURE:
<223> OTHER INFORMATION: Synthetic polypeptide

<400> SEQUENCE: 125

Ser Gln Arg Met Arg Gln Leu Glu Lys Met Leu Glu Asn Asn Thr Gln
1               5                   10                  15

Trp Leu Gln Lys Leu Glu Arg Tyr Ile Gln Val Asn Leu
            20                  25

<210> SEQ ID NO 126
<211> LENGTH: 29
<212> TYPE: PRT
<213> ORGANISM: Artificial
<220> FEATURE:
<223> OTHER INFORMATION: Synthetic polypeptide

<400> SEQUENCE: 126

Thr Gln Arg Val Gln Gln Leu Glu Lys Val Leu Glu Asn Asn Thr Gln
1               5                   10                  15

Trp Leu Gln Lys Leu Glu Arg Tyr Ile Gln Met Asn Leu
            20                  25

<210> SEQ ID NO 127
<211> LENGTH: 29
<212> TYPE: PRT
<213> ORGANISM: Artificial
<220> FEATURE:
<223> OTHER INFORMATION: Synthetic polypeptide

```
<400> SEQUENCE: 127

Ala Gln Arg Val Ser Gln Leu Glu Lys Ile Leu Glu Asn Asn Thr Gln
1               5                   10                  15

Trp Leu Leu Lys Leu Glu Gln Ser Ile Lys Val Asn Leu
            20                  25

<210> SEQ ID NO 128
<211> LENGTH: 29
<212> TYPE: PRT
<213> ORGANISM: Artificial
<220> FEATURE:
<223> OTHER INFORMATION: Synthetic polypeptide

<400> SEQUENCE: 128

Ala Gln Arg Val Ser Gln Leu Glu Lys Ile Leu Glu Asn Asn Thr Gln
1               5                   10                  15

Trp Leu Leu Lys Leu Glu Gln Ser Ile Gln Met Asn Leu
            20                  25

<210> SEQ ID NO 129
<211> LENGTH: 43
<212> TYPE: PRT
<213> ORGANISM: Artificial
<220> FEATURE:
<223> OTHER INFORMATION: Synthetic polypeptide

<400> SEQUENCE: 129

Arg His Asn Ser Ser Leu Leu Gln Asp Gln Gln His Ser Leu Ser Gln
1               5                   10                  15

Leu Leu Leu Leu Leu Arg Asp Leu Val Gln Glu Arg Val Asn Ala Ser
            20                  25                  30

Ala Pro Ala Phe Ile Thr Ala Gly Glu Gln Val
        35                  40

<210> SEQ ID NO 130
<211> LENGTH: 38
<212> TYPE: PRT
<213> ORGANISM: Artificial
<220> FEATURE:
<223> OTHER INFORMATION: Synthetic polypeptide

<400> SEQUENCE: 130

Ser Ser Asn Ser Ser Leu Leu Gln Arg Gln Gln His Gln Leu Leu Glu
1               5                   10                  15

Ser Val Gln Arg Leu Val Arg Val Met Ala Gln Gly Pro Ala Ser Met
            20                  25                  30

Arg Ala Ala Asp Gln Leu
        35

<210> SEQ ID NO 131
<211> LENGTH: 38
<212> TYPE: PRT
<213> ORGANISM: Artificial
<220> FEATURE:
<223> OTHER INFORMATION: Synthetic polypeptide

<400> SEQUENCE: 131

Ser Ser Asn Ser Ser Leu Leu Gln Arg Gln Gln Arg Gln Leu Leu Glu
1               5                   10                  15

Ser Val Gln Arg Leu Val Arg Val Val Ala Gln Gly Pro Ala Ser Val
            20                  25                  30

Arg Ala Ala Glu Gln Leu
        35
```

```
<210> SEQ ID NO 132
<211> LENGTH: 40
<212> TYPE: PRT
<213> ORGANISM: Artificial
<220> FEATURE:
<223> OTHER INFORMATION: Synthetic polypeptide

<400> SEQUENCE: 132

Ser Ser Asn Ser Ser Ser Leu Gln Gln Gln Gln Gln Gln Leu Thr Glu
1               5                   10                  15

Phe Val Gln Arg Leu Val Arg Ile Val Ala Gln Asp Gln His Pro Val
            20                  25                  30

Ser Leu Lys Thr Pro Lys Pro Val
        35                  40

<210> SEQ ID NO 133
<211> LENGTH: 40
<212> TYPE: PRT
<213> ORGANISM: Artificial
<220> FEATURE:
<223> OTHER INFORMATION: Synthetic polypeptide

<400> SEQUENCE: 133

Ser Ser Asn Ser Ser Ser Leu Gln Gln Gln Gln Gln Gln Leu Met Glu
1               5                   10                  15

Leu Val Gln Arg Leu Val Arg Ile Val Ala Gln Asp Gln His Pro Val
            20                  25                  30

Ser Leu Lys Thr Pro Lys Pro Leu
        35                  40

<210> SEQ ID NO 134
<211> LENGTH: 12
<212> TYPE: PRT
<213> ORGANISM: Artificial
<220> FEATURE:
<223> OTHER INFORMATION: Synthetic polypeptide

<400> SEQUENCE: 134

Glu Thr Ser Leu Ser Thr Asn Lys Leu Glu Lys Gln
1               5                   10

<210> SEQ ID NO 135
<211> LENGTH: 12
<212> TYPE: PRT
<213> ORGANISM: Artificial
<220> FEATURE:
<223> OTHER INFORMATION: Synthetic polypeptide

<400> SEQUENCE: 135

Glu Asn Ser Leu Ser Thr Asn Lys Leu Glu Arg Gln
1               5                   10

<210> SEQ ID NO 136
<211> LENGTH: 12
<212> TYPE: PRT
<213> ORGANISM: Artificial
<220> FEATURE:
<223> OTHER INFORMATION: Synthetic polypeptide

<400> SEQUENCE: 136

Glu Ser Ser Leu Ser Thr Asn Lys Leu Glu Arg Gln
1               5                   10
```

```
<210> SEQ ID NO 137
<211> LENGTH: 11
<212> TYPE: PRT
<213> ORGANISM: Artificial
<220> FEATURE:
<223> OTHER INFORMATION: Synthetic polypeptide

<400> SEQUENCE: 137

Leu Met Asp Thr Val His Asn Leu Val Ser Leu
1               5                   10

<210> SEQ ID NO 138
<211> LENGTH: 11
<212> TYPE: PRT
<213> ORGANISM: Artificial
<220> FEATURE:
<223> OTHER INFORMATION: Synthetic polypeptide

<400> SEQUENCE: 138

Leu Met Asp Thr Val His Asn Leu Ile Ser Leu
1               5                   10

<210> SEQ ID NO 139
<211> LENGTH: 11
<212> TYPE: PRT
<213> ORGANISM: Artificial
<220> FEATURE:
<223> OTHER INFORMATION: Synthetic polypeptide

<400> SEQUENCE: 139

Leu Met Asp Thr Val His Thr Leu Ile Thr Leu
1               5                   10

<210> SEQ ID NO 140
<211> LENGTH: 11
<212> TYPE: PRT
<213> ORGANISM: Artificial
<220> FEATURE:
<223> OTHER INFORMATION: Synthetic polypeptide

<400> SEQUENCE: 140

Leu Met Asp Thr Val His Asn Leu Val Lys Leu
1               5                   10

<210> SEQ ID NO 141
<211> LENGTH: 50
<212> TYPE: PRT
<213> ORGANISM: Artificial
<220> FEATURE:
<223> OTHER INFORMATION: Synthetic polypeptide

<400> SEQUENCE: 141

Glu Gly Lys His Lys Glu Glu Leu Asp Thr Leu Lys Glu Glu Lys Glu
1               5                   10                  15

Asn Leu Gln Gly Leu Val Thr Arg Gln Thr Phe Ile Ile Gln Glu Leu
            20                  25                  30

Glu Lys Gln Leu Ser Arg Ala Thr Ser Asn Asn Ser Val Leu Gln Lys
        35                  40                  45

Gln Gln
    50

<210> SEQ ID NO 142
<211> LENGTH: 50
<212> TYPE: PRT
<213> ORGANISM: Artificial
<220> FEATURE:
<223> OTHER INFORMATION: Synthetic polypeptide
```

```
<400> SEQUENCE: 142

Glu Gly Lys His Lys Glu Glu Leu Asp Thr Leu Lys Glu Glu Lys Glu
1               5                   10                  15

Asn Leu Gln Gly Leu Val Ser Arg Gln Thr Phe Ile Ile Gln Glu Leu
            20                  25                  30

Glu Lys Gln Leu Ser Arg Ala Thr Asn Asn Ser Ile Leu Gln Lys
        35                  40                  45

Gln Gln
    50

<210> SEQ ID NO 143
<211> LENGTH: 50
<212> TYPE: PRT
<213> ORGANISM: Artificial
<220> FEATURE:
<223> OTHER INFORMATION: Synthetic polypeptide

<400> SEQUENCE: 143

Glu Gly Lys His Lys Glu Glu Leu Asp Thr Leu Lys Glu Glu Lys Glu
1               5                   10                  15

Asn Leu Gln Ser Leu Val Thr Arg Gln Thr Ser Val Ile Gln Glu Leu
            20                  25                  30

Glu Lys Gln Leu Asn Arg Ala Thr Thr Asn Asn Ser Val Leu Gln Lys
        35                  40                  45

Gln Gln
    50

<210> SEQ ID NO 144
<211> LENGTH: 50
<212> TYPE: PRT
<213> ORGANISM: Artificial
<220> FEATURE:
<223> OTHER INFORMATION: Synthetic polypeptide

<400> SEQUENCE: 144

Glu Gly Lys His Lys Glu Glu Trp Asp Thr Leu Lys Glu Glu Arg Glu
1               5                   10                  15

Asn Leu Gln Val Leu Val Thr Arg Gln Thr Tyr Ile Ile Gln Glu Leu
            20                  25                  30

Glu Lys Gln Leu Asn Arg Ala Thr Asn Asn Ser Val Leu Gln Lys
        35                  40                  45

Gln Gln
    50

<210> SEQ ID NO 145
<211> LENGTH: 50
<212> TYPE: PRT
<213> ORGANISM: Artificial
<220> FEATURE:
<223> OTHER INFORMATION: Synthetic polypeptide

<400> SEQUENCE: 145

Glu Glu Arg His Lys Glu Glu Met Asp Thr Leu Lys Glu Glu Lys Glu
1               5                   10                  15

Asn Leu Gln Ser Leu Val Thr Arg Gln Ser Tyr Ile Ile Gln Glu Leu
            20                  25                  30

Glu Lys Gln Leu Asn Lys Ala Thr Thr Asn Asn Ser Val Leu Gln Lys
        35                  40                  45

Gln Gln
    50
```

```
<210> SEQ ID NO 146
<211> LENGTH: 50
<212> TYPE: PRT
<213> ORGANISM: Artificial
<220> FEATURE:
<223> OTHER INFORMATION: Synthetic polypeptide

<400> SEQUENCE: 146

Glu Glu Arg His Lys Asp Glu Leu Asn Thr Leu Lys Thr Glu Lys Glu
1               5                   10                  15

Ser Leu Gln Asn Leu Val Ser Arg Gln Ile Tyr Ile Ile Gln Glu Leu
            20                  25                  30

Glu Lys Gln Leu Asn Lys Ala Thr Ser Asn Asn Ser Ile Leu Gln Lys
        35                  40                  45

Gln Gln
    50

<210> SEQ ID NO 147
<211> LENGTH: 50
<212> TYPE: PRT
<213> ORGANISM: Artificial
<220> FEATURE:
<223> OTHER INFORMATION: Synthetic polypeptide

<400> SEQUENCE: 147

Glu Glu Arg His Lys Glu Glu Leu Asp Thr Leu Lys Glu Glu Lys Glu
1               5                   10                  15

Asn Leu Gln Ser Leu Val Thr Arg Gln Thr Tyr Ile Ile Gln Glu Leu
            20                  25                  30

Glu Lys Gln Leu Asn Arg Ala Thr Ser Asn Asn Ser Val Leu Gln Lys
        35                  40                  45

Gln Gln
    50

<210> SEQ ID NO 148
<211> LENGTH: 50
<212> TYPE: PRT
<213> ORGANISM: Artificial
<220> FEATURE:
<223> OTHER INFORMATION: Synthetic polypeptide

<400> SEQUENCE: 148

Glu Gly Lys His Lys Glu Glu Leu Asp Thr Leu Lys Glu Glu Lys Glu
1               5                   10                  15

Asn Leu Gln Gly Leu Val Thr Arg Gln Thr Tyr Ile Ile Gln Glu Leu
            20                  25                  30

Lys Lys Gln Leu Asn Arg Ala Thr Thr Asn Asn Ser Val Leu Gln Lys
        35                  40                  45

Gln Gln
    50

<210> SEQ ID NO 149
<211> LENGTH: 25
<212> TYPE: PRT
<213> ORGANISM: Artificial
<220> FEATURE:
<223> OTHER INFORMATION: Synthetic polypeptide

<400> SEQUENCE: 149

Asn Glu Ile Leu Lys Ile Gln Glu Lys Asn Ser Leu Leu Glu His Lys
1               5                   10                  15

Ile Leu Glu Met Glu Gly Lys His Lys
            20                  25
```

```
<210> SEQ ID NO 150
<211> LENGTH: 25
<212> TYPE: PRT
<213> ORGANISM: Artificial
<220> FEATURE:
<223> OTHER INFORMATION: Synthetic polypeptide

<400> SEQUENCE: 150

Asn Glu Ile Leu Lys Ile His Glu Lys Asn Ser Ile Leu Glu His Lys
1               5                   10                  15

Ile Leu Glu Met Glu Gly Lys His Lys
            20                  25

<210> SEQ ID NO 151
<211> LENGTH: 25
<212> TYPE: PRT
<213> ORGANISM: Artificial
<220> FEATURE:
<223> OTHER INFORMATION: Synthetic polypeptide

<400> SEQUENCE: 151

Asn Glu Ile Leu Lys Ile His Glu Lys Asn Ser Leu Leu Glu His Lys
1               5                   10                  15

Ile Leu Glu Met Glu Glu Arg His Lys
            20                  25

<210> SEQ ID NO 152
<211> LENGTH: 25
<212> TYPE: PRT
<213> ORGANISM: Artificial
<220> FEATURE:
<223> OTHER INFORMATION: Synthetic polypeptide

<400> SEQUENCE: 152

Asn Glu Ile Val Lys Ile Gln Glu Lys Asn Ser Leu Leu Glu Asn Lys
1               5                   10                  15

Met Val Glu Met Glu Glu Arg His Lys
            20                  25

<210> SEQ ID NO 153
<211> LENGTH: 25
<212> TYPE: PRT
<213> ORGANISM: Artificial
<220> FEATURE:
<223> OTHER INFORMATION: Synthetic polypeptide

<400> SEQUENCE: 153

His Glu Ile Leu Lys Ile His Glu Lys Asn Ser Leu Leu Glu His Lys
1               5                   10                  15

Ile Leu Glu Met Glu Glu Arg His Lys
            20                  25

<210> SEQ ID NO 154
<211> LENGTH: 25
<212> TYPE: PRT
<213> ORGANISM: Artificial
<220> FEATURE:
<223> OTHER INFORMATION: Synthetic polypeptide

<400> SEQUENCE: 154

Asn Glu Ile Leu Lys Ile His Glu Lys Asn Ser Leu Leu Glu His Lys
1               5                   10                  15

Ile Phe Glu Met Glu Gly Lys His Lys
            20                  25
```

```
<210> SEQ ID NO 155
<211> LENGTH: 30
<212> TYPE: PRT
<213> ORGANISM: Artificial
<220> FEATURE:
<223> OTHER INFORMATION: Synthetic polypeptide

<400> SEQUENCE: 155

Asn Ser Val Leu Gln Lys Gln Gln Leu Glu Leu Met Asp Thr Val His
1               5                   10                  15

Asn Leu Val Ser Leu Cys Thr Lys Glu Val Leu Leu Lys Gly
            20                  25                  30

<210> SEQ ID NO 156
<211> LENGTH: 31
<212> TYPE: PRT
<213> ORGANISM: Artificial
<220> FEATURE:
<223> OTHER INFORMATION: Synthetic polypeptide

<400> SEQUENCE: 156

Asn Ser Ile Leu Gln Lys Gln Gln Leu Glu Leu Met Asp Thr Val His
1               5                   10                  15

Asn Leu Ile Ser Leu Cys Thr Lys Glu Gly Val Leu Leu Lys Gly
            20                  25                  30

<210> SEQ ID NO 157
<211> LENGTH: 30
<212> TYPE: PRT
<213> ORGANISM: Artificial
<220> FEATURE:
<223> OTHER INFORMATION: Synthetic polypeptide

<400> SEQUENCE: 157

Asn Ser Val Leu Gln Lys Gln Gln Leu Glu Leu Met Asp Thr Val His
1               5                   10                  15

Asn Leu Val Asn Leu Cys Thr Lys Glu Val Leu Leu Lys Gly
            20                  25                  30

<210> SEQ ID NO 158
<211> LENGTH: 31
<212> TYPE: PRT
<213> ORGANISM: Artificial
<220> FEATURE:
<223> OTHER INFORMATION: Synthetic polypeptide

<400> SEQUENCE: 158

Asn Ser Val Leu Gln Lys Gln Gln Leu Glu Leu Met Asp Thr Val His
1               5                   10                  15

Thr Leu Ile Thr Leu Cys Ser Lys Glu Gly Val Leu Leu Lys Asn
            20                  25                  30

<210> SEQ ID NO 159
<211> LENGTH: 31
<212> TYPE: PRT
<213> ORGANISM: Artificial
<220> FEATURE:
<223> OTHER INFORMATION: Synthetic polypeptide

<400> SEQUENCE: 159

Asn Ser Ile Leu Gln Lys Gln Gln Leu Glu Leu Met Asp Thr Val His
1               5                   10                  15

Asn Leu Val Lys Leu Cys Ser Lys Glu Gly Val Thr Val Lys Asn
            20                  25                  30
```

```
<210> SEQ ID NO 160
<211> LENGTH: 31
<212> TYPE: PRT
<213> ORGANISM: Artificial
<220> FEATURE:
<223> OTHER INFORMATION: Synthetic polypeptide
<220> FEATURE:
<223> OTHER INFORMATION: Synthetic peptide

<400> SEQUENCE: 160

Asn Ser Val Leu Gln Lys Gln Gln Leu Glu Leu Met Asp Thr Val His
1               5                   10                  15

Asn Leu Val Asn Leu Cys Thr Lys Glu Gly Val Leu Leu Lys Ser
            20                  25                  30

<210> SEQ ID NO 161
<211> LENGTH: 11
<212> TYPE: PRT
<213> ORGANISM: Artificial
<220> FEATURE:
<223> OTHER INFORMATION: Synthetic polypeptide

<400> SEQUENCE: 161

Ser Asn Asn Ser Val Leu Gln Lys Gln Gln Leu
1               5                   10

<210> SEQ ID NO 162
<211> LENGTH: 11
<212> TYPE: PRT
<213> ORGANISM: Artificial
<220> FEATURE:
<223> OTHER INFORMATION: Synthetic polypeptide

<400> SEQUENCE: 162

Asn Asn Asn Ser Ile Leu Gln Lys Gln Gln Leu
1               5                   10

<210> SEQ ID NO 163
<211> LENGTH: 11
<212> TYPE: PRT
<213> ORGANISM: Artificial
<220> FEATURE:
<223> OTHER INFORMATION: Synthetic polypeptide

<400> SEQUENCE: 163

Asn Asn Asn Ser Val Leu Gln Lys Gln Gln Leu
1               5                   10

<210> SEQ ID NO 164
<211> LENGTH: 11
<212> TYPE: PRT
<213> ORGANISM: Artificial
<220> FEATURE:
<223> OTHER INFORMATION: Synthetic polypeptide

<400> SEQUENCE: 164

Ser Asn Asn Ser Ile Leu Gln Lys Gln Gln Leu
1               5                   10

<210> SEQ ID NO 165
<211> LENGTH: 30
<212> TYPE: PRT
<213> ORGANISM: Artificial
<220> FEATURE:
<223> OTHER INFORMATION: Synthetic polypeptide
```

```
<400> SEQUENCE: 165

Leu Lys Glu Glu Lys Glu Asn Leu Gln Gly Leu Val Thr Arg Gln Thr
1               5                   10                  15

Phe Ile Ile Gln Glu Leu Glu Lys Gln Leu Ser Arg Ala Thr
            20                  25                  30

<210> SEQ ID NO 166
<211> LENGTH: 30
<212> TYPE: PRT
<213> ORGANISM: Artificial
<220> FEATURE:
<223> OTHER INFORMATION: Synthetic polypeptide

<400> SEQUENCE: 166

Leu Lys Glu Glu Lys Glu Asn Leu Gln Gly Leu Val Ser Arg Gln Thr
1               5                   10                  15

Phe Ile Ile Gln Glu Leu Glu Lys Gln Leu Ser Arg Ala Thr
            20                  25                  30

<210> SEQ ID NO 167
<211> LENGTH: 30
<212> TYPE: PRT
<213> ORGANISM: Artificial
<220> FEATURE:
<223> OTHER INFORMATION: Synthetic polypeptide

<400> SEQUENCE: 167

Leu Lys Glu Glu Lys Glu Asn Leu Gln Ser Leu Val Thr Arg Gln Thr
1               5                   10                  15

Ser Val Ile Gln Glu Leu Glu Lys Gln Leu Asn Arg Ala Thr
            20                  25                  30

<210> SEQ ID NO 168
<211> LENGTH: 30
<212> TYPE: PRT
<213> ORGANISM: Artificial
<220> FEATURE:
<223> OTHER INFORMATION: Synthetic polypeptide

<400> SEQUENCE: 168

Leu Lys Glu Glu Arg Glu Asn Leu Gln Val Leu Val Thr Arg Gln Thr
1               5                   10                  15

Tyr Ile Ile Gln Glu Leu Glu Lys Gln Leu Asn Arg Ala Thr
            20                  25                  30

<210> SEQ ID NO 169
<211> LENGTH: 30
<212> TYPE: PRT
<213> ORGANISM: Artificial
<220> FEATURE:
<223> OTHER INFORMATION: Synthetic polypeptide

<400> SEQUENCE: 169

Leu Lys Glu Glu Lys Glu Asn Leu Gln Ser Leu Val Thr Arg Gln Ser
1               5                   10                  15

Tyr Ile Ile Gln Glu Leu Glu Lys Gln Leu Asn Lys Ala Thr
            20                  25                  30

<210> SEQ ID NO 170
<211> LENGTH: 30
<212> TYPE: PRT
<213> ORGANISM: Artificial
<220> FEATURE:
<223> OTHER INFORMATION: Synthetic polypeptide
```

<400> SEQUENCE: 170

Leu Lys Thr Glu Lys Glu Ser Leu Gln Asn Leu Val Ser Arg Gln Ile
1               5                   10                  15

Tyr Ile Ile Gln Glu Leu Glu Lys Gln Leu Asn Lys Ala Thr
            20                  25                  30

<210> SEQ ID NO 171
<211> LENGTH: 30
<212> TYPE: PRT
<213> ORGANISM: Artificial
<220> FEATURE:
<223> OTHER INFORMATION: Synthetic polypeptide

<400> SEQUENCE: 171

Leu Lys Glu Glu Lys Glu Asn Leu Gln Ser Leu Val Thr Arg Gln Thr
1               5                   10                  15

Tyr Ile Ile Gln Glu Leu Glu Lys Gln Leu Asn Arg Ala Thr
            20                  25                  30

<210> SEQ ID NO 172
<211> LENGTH: 30
<212> TYPE: PRT
<213> ORGANISM: Artificial
<220> FEATURE:
<223> OTHER INFORMATION: Synthetic polypeptide

<400> SEQUENCE: 172

Leu Lys Glu Glu Lys Glu Asn Leu Gln Gly Leu Val Thr Arg Gln Thr
1               5                   10                  15

Tyr Ile Ile Gln Glu Leu Lys Lys Gln Leu Asn Arg Ala Thr
            20                  25                  30

<210> SEQ ID NO 173
<211> LENGTH: 32
<212> TYPE: PRT
<213> ORGANISM: Artificial
<220> FEATURE:
<223> OTHER INFORMATION: Synthetic polypeptide

<400> SEQUENCE: 173

Gln Glu Leu Glu Lys Gln Leu Ser Arg Ala Thr Ser Asn Asn Ser Val
1               5                   10                  15

Leu Gln Lys Gln Gln Leu Glu Leu Met Asp Thr Val His Asn Leu Val
            20                  25                  30

<210> SEQ ID NO 174
<211> LENGTH: 32
<212> TYPE: PRT
<213> ORGANISM: Artificial
<220> FEATURE:
<223> OTHER INFORMATION: Synthetic polypeptide

<400> SEQUENCE: 174

Gln Glu Leu Glu Lys Gln Leu Ser Arg Ala Thr Asn Asn Asn Ser Ile
1               5                   10                  15

Leu Gln Lys Gln Gln Leu Glu Leu Met Asp Thr Val His Asn Leu Ile
            20                  25                  30

<210> SEQ ID NO 175
<211> LENGTH: 32
<212> TYPE: PRT
<213> ORGANISM: Artificial
<220> FEATURE:
<223> OTHER INFORMATION: Synthetic polypeptide

```
<400> SEQUENCE: 175

Gln Glu Leu Glu Lys Gln Leu Asn Arg Ala Thr Asn Asn Ser Val
1               5                   10                  15

Leu Gln Lys Gln Gln Leu Glu Leu Met Asp Thr Val His Asn Leu Val
            20                  25                  30

<210> SEQ ID NO 176
<211> LENGTH: 32
<212> TYPE: PRT
<213> ORGANISM: Artificial
<220> FEATURE:
<223> OTHER INFORMATION: Synthetic polypeptide

<400> SEQUENCE: 176

Gln Glu Leu Glu Lys Gln Leu Asn Lys Ala Thr Thr Asn Asn Ser Val
1               5                   10                  15

Leu Gln Lys Gln Gln Leu Glu Leu Met Asp Thr Val His Thr Leu Ile
            20                  25                  30

<210> SEQ ID NO 177
<211> LENGTH: 32
<212> TYPE: PRT
<213> ORGANISM: Artificial
<220> FEATURE:
<223> OTHER INFORMATION: Synthetic polypeptide

<400> SEQUENCE: 177

Gln Glu Leu Glu Lys Gln Leu Asn Lys Ala Thr Ser Asn Asn Ser Ile
1               5                   10                  15

Leu Gln Lys Gln Gln Leu Glu Leu Met Asp Thr Val His Asn Leu Val
            20                  25                  30

<210> SEQ ID NO 178
<211> LENGTH: 32
<212> TYPE: PRT
<213> ORGANISM: Artificial
<220> FEATURE:
<223> OTHER INFORMATION: Synthetic polypeptide

<400> SEQUENCE: 178

Gln Glu Leu Glu Lys Gln Leu Asn Arg Ala Thr Ser Asn Asn Ser Val
1               5                   10                  15

Leu Gln Lys Gln Gln Leu Glu Leu Met Asp Thr Val His Asn Leu Val
            20                  25                  30

<210> SEQ ID NO 179
<211> LENGTH: 32
<212> TYPE: PRT
<213> ORGANISM: Artificial
<220> FEATURE:
<223> OTHER INFORMATION: Synthetic polypeptide

<400> SEQUENCE: 179

Gln Glu Leu Lys Lys Gln Leu Asn Arg Ala Thr Thr Asn Asn Ser Val
1               5                   10                  15

Leu Gln Lys Gln Gln Leu Glu Leu Met Asp Thr Val His Asn Leu Val
            20                  25                  30

<210> SEQ ID NO 180
<211> LENGTH: 45
<212> TYPE: PRT
<213> ORGANISM: Artificial
<220> FEATURE:
<223> OTHER INFORMATION: Synthetic polypeptide
```

<400> SEQUENCE: 180

Glu Leu Glu Lys Gln Leu Leu Gln Gln Thr Asn Glu Ile Leu Lys Ile
1               5                   10                  15

Gln Glu Lys Asn Ser Leu Leu Glu His Lys Ile Leu Glu Met Glu Gly
            20                  25                  30

Lys His Lys Glu Glu Leu Asp Thr Leu Lys Glu Glu Lys
        35                  40                  45

<210> SEQ ID NO 181
<211> LENGTH: 45
<212> TYPE: PRT
<213> ORGANISM: Artificial
<220> FEATURE:
<223> OTHER INFORMATION: Synthetic polypeptide

<400> SEQUENCE: 181

Lys Leu Glu Lys Gln Leu Leu Gln Gln Thr Asn Glu Ile Leu Lys Ile
1               5                   10                  15

His Glu Lys Asn Ser Ile Leu Glu His Lys Ile Leu Glu Met Glu Gly
            20                  25                  30

Lys His Lys Glu Glu Leu Asp Thr Leu Lys Glu Glu Lys
        35                  40                  45

<210> SEQ ID NO 182
<211> LENGTH: 45
<212> TYPE: PRT
<213> ORGANISM: Artificial
<220> FEATURE:
<223> OTHER INFORMATION: Synthetic polypeptide

<400> SEQUENCE: 182

Lys Leu Glu Lys Gln Leu Leu Gln Gln Thr Asn Glu Ile Leu Lys Ile
1               5                   10                  15

His Glu Lys Asn Ser Leu Leu Glu His Lys Ile Leu Glu Met Glu Gly
            20                  25                  30

Lys His Lys Glu Glu Trp Asp Thr Leu Lys Glu Glu Arg
        35                  40                  45

<210> SEQ ID NO 183
<211> LENGTH: 45
<212> TYPE: PRT
<213> ORGANISM: Artificial
<220> FEATURE:
<223> OTHER INFORMATION: Synthetic polypeptide

<400> SEQUENCE: 183

Lys Leu Glu Lys Gln Leu Leu Gln Gln Thr Asn Glu Ile Leu Lys Ile
1               5                   10                  15

His Glu Lys Asn Ser Leu Leu Glu His Lys Ile Leu Glu Met Glu Glu
            20                  25                  30

Arg His Lys Glu Glu Met Asp Thr Leu Lys Glu Glu Lys
        35                  40                  45

<210> SEQ ID NO 184
<211> LENGTH: 45
<212> TYPE: PRT
<213> ORGANISM: Artificial
<220> FEATURE:
<223> OTHER INFORMATION: Synthetic polypeptide

```
-continued

<400> SEQUENCE: 184

Lys Leu Glu Lys Gln Leu Ile Gln Gln Thr Asn Glu Ile Val Lys Ile
1               5                   10                  15

Gln Glu Lys Asn Ser Leu Leu Glu Asn Lys Met Val Glu Met Glu Glu
            20                  25                  30

Arg His Lys Asp Glu Leu Asn Thr Leu Lys Thr Glu Lys
        35                  40                  45

<210> SEQ ID NO 185
<211> LENGTH: 45
<212> TYPE: PRT
<213> ORGANISM: Artificial
<220> FEATURE:
<223> OTHER INFORMATION: Synthetic polypeptide

<400> SEQUENCE: 185

Lys Leu Glu Lys Gln Leu Leu Gln Gln Thr His Glu Ile Leu Lys Ile
1               5                   10                  15

His Glu Lys Asn Ser Leu Leu Glu His Lys Ile Leu Glu Met Glu Glu
            20                  25                  30

Arg His Lys Glu Glu Leu Asp Thr Leu Lys Glu Glu Lys
        35                  40                  45

<210> SEQ ID NO 186
<211> LENGTH: 45
<212> TYPE: PRT
<213> ORGANISM: Artificial
<220> FEATURE:
<223> OTHER INFORMATION: Synthetic polypeptide

<400> SEQUENCE: 186

Lys Leu Glu Lys Gln Leu Leu Gln Gln Thr Asn Glu Ile Leu Lys Ile
1               5                   10                  15

His Glu Lys Asn Ser Leu Leu Glu His Lys Ile Phe Glu Met Glu Gly
            20                  25                  30

Lys His Lys Glu Glu Leu Asp Thr Leu Lys Glu Glu Lys
        35                  40                  45
```